(12) United States Patent
Khalili et al.

(10) Patent No.: US 12,122,997 B2
(45) Date of Patent: Oct. 22, 2024

(54) EXCISION OF RETROVIRAL NUCLEIC ACID SEQUENCES

(71) Applicant: Temple University—Of The Commonwealth System of Higher Education, Philadelphia, PA (US)

(72) Inventors: Kamel Khalili, Bala Cynwyd, PA (US); Wenhui Hu, Cherry Hill, NJ (US)

(73) Assignee: Temple University—of the Commonwealth System of Higher Education, Philadelphia, PA (US)

(*) Notice: Subject to any disclaimer, the term of this patent is extended or adjusted under 35 U.S.C. 154(b) by 364 days.

(21) Appl. No.: 15/998,558

(22) PCT Filed: Feb. 13, 2017

(86) PCT No.: PCT/US2017/017652
§ 371 (c)(1),
(2) Date: Aug. 15, 2018

(87) PCT Pub. No.: WO2017/142835
PCT Pub. Date: Aug. 24, 2017

(65) Prior Publication Data
US 2019/0225963 A1 Jul. 25, 2019

Related U.S. Application Data

(60) Provisional application No. 62/410,496, filed on Oct. 20, 2016, provisional application No. 62/363,625, filed on Jul. 18, 2016, provisional application No. 62/345,520, filed on Jun. 3, 2016, provisional application No. 62/337,994, filed on May 18, 2016, provisional application No. 62/298,722, filed on Feb. 23, 2016, provisional application No. 62/295,390, filed on Feb. 15, 2016.

(51) Int. Cl.
*C12N 15/11* (2006.01)
*A61K 48/00* (2006.01)
*C12N 9/22* (2006.01)
*C12N 15/113* (2010.01)

(52) U.S. Cl.
CPC .............. *C12N 15/11* (2013.01); *A61K 48/00* (2013.01); *C12N 9/22* (2013.01); *C12N 15/1132* (2013.01); *A01K 2227/105* (2013.01); *A01K 2267/0337* (2013.01); *C07K 2319/09* (2013.01); *C12N 2310/20* (2017.05); *C12N 2750/14143* (2013.01)

(58) Field of Classification Search
CPC ...... C12N 15/11; C12N 9/22; C12N 15/1132; C12N 2310/20; C12N 2750/14143; A61K 48/00; A01K 2227/105; A01K 2267/0337; C07K 2319/09; A61P 31/14; A61P 31/18
See application file for complete search history.

(56) References Cited

U.S. PATENT DOCUMENTS

| | | |
|---|---|---|
| 2011/0159025 A1 | 6/2011 | Littman et al. |
| 2014/0357530 A1 | 12/2014 | Zhang et al. |
| 2015/0020223 A1 | 1/2015 | Zhang et al. |
| 2019/0225963 A1 | 7/2019 | Khalili et al. |

FOREIGN PATENT DOCUMENTS

| | | | |
|---|---|---|---|
| CN | 104726449 A | 6/2015 | |
| WO | WO-95/22618 A1 | 8/1995 | |
| WO | WO-2015031775 A1 * | 3/2015 | ............. A61K 48/00 |
| WO | WO-2017/142835 A1 | 8/2017 | |

OTHER PUBLICATIONS

Boerner et al. AAV Vector-Mediated CRISPR Attacks on Proviral HIV-1 DNA for Purging of Cellular Reservoirs. Molecular Therapy 23 (2015): S25 (Year: 2015).*
Hu et al. "RNA-directed gene editing specifically eradicates latent and prevents new HIV-1 infection." Proceedings of the National Academy of Sciences 111.31 (2014): 11461-11466 (Year: 2014).*
Sternberg et al. "Expanding the biologist's toolkit with CRISPR-Cas9." Molecular cell 58.4 (2015): 568-574 (Year: 2015).*
Freed et al. "HIV-1 gag proteins: diverse functions in the virus life cycle." Virology 251.1 (1998): 1-15 (Year: 1998).*
Xie et al. "sgRNAcas9: a software package for designing CRISPR sgRNA and evaluating potential off-target cleavage sites." PloS one 9.6 (2014): e100448 (Year: 2014).*
Adejumo et al. (2015) "Contemporary Issues on the Epidemiology and Antiretroviral Adherence of HIV-Infected Adolescents in Sub-Saharan Africa: A Narrative Review," Journal of the International AIDS Society, 18:20049.
Allocca et al. (May 2008) "Serotype-Dependent Packaging of Large Genes in Adeno-Associated Viral Vectors Results in Effective Gene Delivery in Mice," Journal of Clinical Investigation, 118(5):1955-1964.
Barisoni et al. (Jul. 2000) "HIV-1 Induces Renal Epithelial Dedifferentiation in a Transgenic Model of HIV—Associated Nephropathy," Kidney International, 58(1):173-181.
Bartel et al. (2011) "Enhancing the Clinical Potential of AAV Vectors by Capsid Engineering to Evade Pre-Existing Immunity," Frontiers in Microbiology, 2:204, 10 pages.
Bennett et al. (Feb. 8, 2012) "AAV2 Gene Therapy Readministration in Three Adults with Congenital Blindness," Science Translational Medicine, 4(120):120ra15.
Boudreau et al. (Mar. 31, 2011) "RNAi Medicine for the Brain: Progresses and Challenges," Human Molecular Genetics, 20(1):R21-R27.
Brandau et al. (Sep. 2000) "Perforin-mediated Lysis of Tumor Cells by *Mycobacterium bovis* Bacillus Calmette-Gue'rin-activated Killer Cells," Clinical Cancer Research, 6:3729-3738.

(Continued)

*Primary Examiner* — Jeremy C Flinders
*Assistant Examiner* — Alexander W Nicol
(74) *Attorney, Agent, or Firm* — Fox Rothschild LLP; Nicholas Zachariades

(57) ABSTRACT

Compositions for the in vivo delivery of a gene editing CRISPR/Cas9 complex was developed to eliminate integrated retroviral DNA sequences from latently infected human cells and animal disease models.

11 Claims, 26 Drawing Sheets

Specification includes a Sequence Listing.

(56) References Cited

OTHER PUBLICATIONS

Browne et al. (Dec. 1999) "Cytosolic Delivery of Granzyme B by Bacterial Toxins: Evidence that Endosomal Disruption, in Addition to Transmembrane Pore Formation, Is an Important Function of Perforin," Molecular and Cellular Biology, 19(12):8604-8615.
Chang et al. (2013) "Genome Editing with RNA-Guided Cas9 Nuclease in Zebrafish Embryos," Cell Research, 23:465-472.
Chen et al. (Jan. 2003) "Expression of ssDNA in Mammalian Cells," Biotechniques, 34(1):167-171.
Cheung et al. (Aug. 2015) "Cardiac Dysfunction in HIV-1 Transgenic Mouse: Role of Stress and BAG3," Clinical and Translational Science, 8(4):305-310.
Christiensen et al. (1998) "A Novel Class of Oligonucleotide Analogues Containing 2'-0,3'-C-Linked [3.2.0] Bicycloarabinonucleoside Monomers: Synthesis, Thermal Affinity Studies, and Molecular Modeling," Journal of the American Chemical Society, 120(22):5458-5463.
Coffin et al. (1995) "HIV Population Dynamics in Vivo: Implications for Genetic Variation, Pathogenesis, and Therapy," Science, 267:483-489.
Cong et al. (Feb. 15, 2013) "Multiplex Genome Engineering Using CRISPR/Cas Systems," Science, 339(6121): 819-823.
Cruz et al. (Nov. 1999) "Lack of MHC Class I Surface Expression on Neoplastic Cells and Poor Activation of the Secretory Pathway of Cytotoxic Cells in Oral Squamous Cell Carcinomas," British Journal of Cancer, 81(5):881-889.
Curiel et al. (Oct. 1991) "Adenovirus Enhancement of Transferrin-Polylysine-Mediated Gene Delivery," PNAS, 88:8850-8854.
Curreli et al. (2013) "B cell Lymphoma in HIV Transgenic Mice," Retrovirology, 10:92:13 pages.
Database Genbank (Aug. 9, 2014) "Expression Vector pCas9, Complete Sequence," Genbank Accession No. KM099231 .1, 4 pages.
Database Genbank (Aug. 9, 2014) "Expression Vector pCas9_eba175 sgRNA, Complete Sequence," Genbank Accession Nos. KM099233.1, 4 pages.
Database Genbank (Aug. 9, 2014) "Expression Vector pCas9_kahrp sgRNA, Complete Sequence," Genbank Accession Nos. KM099232.1, 4 pages.
Davis et al. (Apr. 1993) "Direct Gene Transfer into Skeletal Muscle In Vivo: Factors Affecting Efficiency of Transfer and Stability of Expression," Human Gene Therapy, 4(2):151-159.
De Mesmaeker et al. (1995) "Antisense Oligonucleotides," Accounts of Chemical Research, 28(9):366-374.
Ebina et al. (Aug. 26, 2013) "Harnessing the CRISPR/Cas9 System to Disrupt Latent HIV-1 Provirus," Scientific Reports, 3(2510):07 pages.
Fine et al. (2015) "Trans-Spliced Cas9 Allows Cleavage of HBB and CCR5 Genes in Human Cells Using Compact Expression Cassettes," Scientific Reports, 2015, 5(10777), 9 pages.
Freier et al. (1997) "The Ups and Downs of Nucleic Acid Duplex Stability: Structure-Stability Studies on Chemically-Modified DNA:RNA Duplexes," Nucleic Acids Research, 25(22):4429-4443.
Friedland et al. (2015) "Characterization of *Staphylococcus aureus* Cas9: a Smaller Cas9 for All-in-one Adeno- Associated Virus Delivery and Paired Nickase Applications," Genome Biology, 16: 257, 10 pages.
Gao et al. (Apr. 2014) "Selfprocessing of Ribozymeflanked Rnas Into Guide Rnas in Vitro and in Vivo for Crisprmediated Genome Editing," Journal of Integrative Plant Biology, 56(4):343-349.
Geller et al. (1990) "Infection of Cultured Central Nervous System Neurons with a Defective Herpes Simplex Virus 1 Vector Results in Stable Expression of *Escherichia coli* ß-galactosidase," PNAS, 87(3):1149-1153.
Geller et al. (1993) "Long-Term Increases in Neurotransmitter Release from Neuronal Cells Expressing a Constitutively Active Adenylate Cyclase from a Herpes Simplex Virus Type 1 Vector," PNAS, 90(16):7603-7607.
Geller et al. (Feb. 1995) "An HSV-1 Vector Expressing Tyrosine Hydroxylase Causes Production and Release of L-DOPA from Cultured Rat Striatal Cells," Journal of Neurochemistry, 64(2):487-496.
Gilbert et al. (Jul. 18, 2013) "CRISPR-Mediated Modular RNA-Guided Regulation of Transcription in Eukaryotes," Cell, 154:442-451.
Grieger et al. (Aug. 2005) "Packaging Capacity of Adeno-Associated Virus Serotypes: Impact of Larger Genomes on Infectivity and Postentry Steps," Journal of Virology, 79(15):9933-9944.
Grimm et al. (Jun. 2008) "In Vitro and In Vivo Gene Therapy Vector Evolution via Multispecies Interbreeding and Retargeting of Adeno-Associated Viruses," Journal of Virology, 82(12):5887-5911.
Haque et al. (Feb. 2016) "HIV Promotes NLRP3 Inflammasome Complex Activation in Murine HIV-Associated Nephropathy," The American Journal of Pathology, 186(2):347-358.
Hastie et al. (May 2015) "Adeno-Associated Virus at 50: A Golden Anniversary of Discovery, Research, and Gene Therapy Success—A Personal Perspective," Human Gene Therapy, 26:257- 265.
Holehonnur et al. (2014) "Adeno-Associated Viral Serotypes Produce Differing Titers and Differentially Transduce Neurons Within the Rat Basal and Lateral Amygdala," BMC Neuroscience, 15(28):14 pages.
Horvath et al. (Jan. 8, 2010) "CRISPR/Cas, the Immune System of Bacteria and Archaea," Science, 327 (5962):167-170.
Howes et al. (2015) "Genome Engineering Using Adeno-Associated Virus (AAV)," Methods in Molecular Biology, 1239:75-103.
Hu et al. (Oct. 1, 2013) "RNA-Mediated Excision of the HIV-1 Genome from Latently Infected Cells in Nervous System," Journal of Neuro Virology, 19(Suppl 1):1 page.
Hwang et al. (Jan. 2013) "Efficient Genome Editing in Zebrafish using a CRISPR-Cas System," Nature Biotechnology, 31(3):227-229.
Jinek et al. (2013) "RNA-Programmed Genome Editing in Human Cells," eLife, 2(e00471):1-9.
Jinek et al. (Aug. 17, 2012) "A Programmable Dual-RNA-Guided DNA Endonuclease in Adaptive Bacterial Immunity," Science, 337(6069):816-821.
Kabadi et al. (2014) "Multiplex CRISPR/Cas9-Based Genome Engineering from a Single Lentiviral Vector," Nucleic Acids Research, 42(19):e147.
Kabanov et al. (Jan. 1, 1990) "A New Class of Antivirals: Antisense Oligonucleotides Combined with a Hydrophobic Substituent Effectively Inhibit Influenza Virus Reproduction and Synthesis of Virus-Specific Proteins in MDCK Cells," FEBS Letters, 259(2):327-330.
Kam et al. (Mar. 7, 2000) "Granzymes (Lymphocyte Serine Proteases): Characterization with Natural and Synthetic Substrates and Inhibitors," Biochimica et Biophysica Acta (BBA)—Protein Structure and Molecular Enzymology, 1477 (1-2):307-323.
Kaminski et al. (2016) "Elimination of HIV-1 Genomes from Human T-lymphoid Cells by CRISPR/ Cas9 Gene Editing," Scientific Reports, 6(22555):14 pages.
Kelschenbach et al. (Jun. 2012) "Mice Chronically Infected with Chimeric HIV Resist Peripheral and Brain Superinfection: A Model of Protective Immunity to HIV," Journal of NeuroImmune Pharmacology, 7(2):380-387.
Khalili et al. (Jun. 2015) "Genome Editing Strategies: Potential Tools for Eradicating HIV-1/AIDS," Journal of Neuro Virology, 21(3):310-321.
Kleinstiver et al. (Jan. 2016) "High-Fidelity CRISPR-Cas9 Nucleases With No Detectable Genome-Wide Off-Target Effects," Nature, 529(7587):490-495.
Kopp et al. (Mar. 1992) "Progressive Glomerulosclerosis and Enhanced Renal Accumulation of Basement Membrane Components in Mice Transgenic for Human Immunodeficiency Virus Type 1 Genes," PNAS, 89 (5):1577-1581.
Kulpa et al. (2015) "HIV Persistence in the Setting of Antiretroviral Therapy: When, Where and How Does HIV Hide?," Journal of Virus Eradication, 1:59-66.
Letsinger et al. (1989) "Cholesteryl-Conjugated Oligonucleotides: Synthesis, Properties, and Activity as Inhibitors of Replication of Human Immunodeficiency Virus in Cell Culture," PNAS, Sep. 1, 86(17):6553-6556.

(56) References Cited

OTHER PUBLICATIONS

Liao et al. (2015) "Use of the CRISPR/Cas9 System as an Intracellular Defense against HIV-1 Infection in Human Cells," Nature Communications, 6(6413):10 pages.
Mali et al. (Feb. 15, 2013) "RNA-Guided Human Genome Engineering via Cas9," Science, 339(6121):823-826.
Mao et al. (2016) "Single Point Mutation in Adeno-Associated Viral Vectors—DJ Capsid Leads to Improvement for Gene Delivery in Vivo," BMC Biotechnology, 16(1):8 pages.
Metz et al. (1997) "Role of Macrophage Migration Inhibitory Factor in the Regulation of the Immune Response," Advances in Immunology, 66:197-223.
Michiel et al. (Feb. 1992) "Cytokines as Positive and Negative Regulators of Tumor Promotion and Progression," Seminars in Cancer Biology, 3(1):3-15.
Mingozzi et al. (Jul. 4, 2013) "Immune Responses to AAV Vectors: Overcoming Barriers to Successful Gene Therapy," Blood, 122(1):23-36.
Mittermeyer et al. (Apr. 2012) "Long-Term Evaluation of a Phase 1 Study of AADC Gene Therapy for Parkinson's Disease," Human Gene Therapy, 23:377-381.
Naldini (Oct. 15, 2015) "Gene Therapy Returns to Centre Stage," Nature, 526:351-360.
Nishimasu et al. (Aug. 27, 2015) "Crystal structure of *Staphylococcus aureus* Cas9," Cell, 162(5):1113-1126.
Nissim et al. (May 22, 2014) "Multiplexed and Programmable Regulation of Gene Networks with an Integrated RNA and CRISPR/Cas Toolkit in Human Cells," Molecular Cell, 54(4):698-710.
Oberhauser et al. (Feb. 11, 1992) "Effective Incorporation of 2'-O-Methyl-Oligoribonucleotides into Liposomes and Enhanced Cell Association through Modification with Thiocholesterol," Nucleic Acids Research, 20(3):533-538.
Oppenheim et al. (Dec. 1997) "Prospects for Cytokine and Chemokine Biotherapy," Clinical Cancer Research, 3(12 Pt 2):2682-2686.
Pelascini et al. (Dec. 2013) "Histone Deacetylase Inhibition Rescues Gene Knockout Levels Achieved with Integrase-Defective Lentiviral Vectors Encoding Zinc-Finger Nucleases," Human Gene Therapy Methods, 24:399-411.
Platt et al. (Oct. 9, 2014) "CRISPR-Cas9 Knockin Mice for Genome Editing and Cancer Modeling," Cell, 159 (2):440-455.
Pontes et al. (2014) "Codon Swapping of Zinc Finger Nucleases Confers Expression in Primary Cells and In Vivo from a Single Lentiviral Vector," Current Gene Therapy, 14:365-376.
Potash et al. (Mar. 8, 2005) "A Mouse Model for Study of Systemic HIV-1 Infection, Antiviral Immune Responses, and Neuroinvasiveness," PNAS, 102(10):3760-3765.
Qi et al. (Feb. 28, 2013) "Repurposing CRISPR as an RNA-Guided Platform for Sequence-Specific Control of Gene Expression," Cell, 152:1173-1183.
Quantin et al. (Apr. 1992) "Adenovirus as an Expression Vector in Muscle Cells in Vivo," PNAS, 89:2581-2584.
Rabinovich et al. (Sep. 23, 2008) "Visualizing Fewer than 10 Mouse T Cells with an Enhanced Firefly Luciferase in Immunocompetent Mouse Models of Cancer," PNAS, 105(38):14342-14346.
Ran et al. (Apr. 9, 2015) "In Vivo Genome Editing Using *Staphylococcus aureus* Cas9," Nature, 520:186-191.
Saison-Behmoaras et al. (1991) "Short Modified Antisense Oligonucleotides Directed Against Ha-ras Point Mutation Induce Selective Cleavage of the mRNA and Inhibit T24 Cells Proliferation," EMBO Journal, 10(5):111-118.
Sakuma et al. (2014) "Multiplex Genome Engineering in Human Cells Using All-In-One CRISPR/Cas9 Vector System," Scientific Reports, 4(5400): 6 pages.
Saleh et al. (2007) "CCR7 Ligands CCL19 and CCL21 Increase Permissiveness of Resting Memory CD4+ T Cells to HIV-1 Infection: A Novel Model of HIV-1 Latency," Blood, 110(13):4161-4164.
Schiffer et al. (Sep. 2012) "Targeted DNA Mutagenesis for the Cure of Chronic Viral Infections," Journal of Virology, 86(17):8920-8936.
Shea et al. (Jul. 11, 1990) "Synthesis, Hybridization Properties and Antiviral Activity of Lipid-Oligodeoxynucleotide Conjugates," Nucleic Acids Research, 18(13):3777-3783.
Slaymaker et al. (Jan. 1, 2016) "Rationally Engineered Cas9 Nucleases With Improved Specificity," Science, 351(6268):84-88.
Song et al. (Oct. 2015) "Visualization and Quantification of Simian Immunodeficiency Virus-Infected Cells using Non-Invasive Molecular Imaging," Journal of General Virology, 96:3131-3142.
Stratford-Perricadet (Aug. 1, 1992) "Widespread Long-term Gene Transfer to Mouse Skeletal Muscles and Heart," Journal of Clinical Investigation, 90(2):626-630.
Swiech et al. (Jan. 2015) "In Vivo Interrogation of Gene Function in the Mammalian Brain using CRISPR-Cas9," Nature Biotechnology, 33(1):102-106.
Swiggard et al. (Nov. 2005) "Human Immunodeficiency Virus Type 1 Can Establish Latent Infection in Resting CD4+T Cells in the Absence of Activating Stimuli," Journal of Virology, 79(22):14179-14188.
Taub et al. (Aug. 1994) "Chemokines, Inflammation and the Immune System," Therapeutic Immunology, 1 (4):229-246.
Ter Brake et al. (Dec. 2006) "Silencing of HIV-1 with RNA Interference: a Multiple shRNA Approach," Molecular Therapy, 14(6):883-892.
Ter Brake et al. (Mar. 2008) "Lentiviral Vector Design for Multiple shRNA Expression and Durable HIV-1 Inhibition," Molecular Therapy, 16(3):557-564.
Terns et al. (Jun. 2011) "CRISPR-Based Adaptive Immune Systems," Current Opinion in Microbiology, 14(3): 321-327.
Von Eije et al. (Jun. 2009) "Stringent Testing Identifies Highly Potent and Escape-Proof Anti-HIV Short Hairpin RNAs," The Journal of Gene Medicine, 11(6):459-467.
Wang et al. (Mar. 2016) "CRISPR-Cas9 can Inhibit HIV-1 Replication but NHEJ Repair Facilitates Virus Escape," Molecular Therapy, 24(3):522-526.
Wang et al. (May 2, 2013) "One-Step Generation of Mice Carrying Reporter and Conditional Alleles by CRISPR/Cas-Mediated Genome Engineering," Cell, 153(4):910-918.
Wright et al. (Mar. 10, 2015) "Rational Design of a Split-Cas9 Enzyme Complex," PNAS, 112(10):2984-2989.
Wu et al. (Jan. 2010) "Effect of Genome Size on AAV Vector Packaging," Molecular Therapy, 18(1):80-86.
Xiao et al. (2013) "Chromosomal Deletions and Inversions Mediated by Talens and CRISPR/Cas in Zebrafish," Nucleic Acids Research, 41(14):1-11.
Yang et al. (Apr. 1995) "Cellular and Humoral Immune Responses to Viral Antigens Create Barriers to Lung-Directed Gene Therapy with Recombinant Adenoviruses," Journal of Virology, 69(4):2004-2015.
Yang et al. (Sep. 12, 2013) "One-Step Generation of Mice Carrying Reporter and Conditional Alleles by CRISPR/Cas Mediated Genome Engineering," Cell, 154(6):1370-1379.
Yin et al. (May 15, 2016) "Functional Screening of Guide RNAs Targeting the Regulatory and Structural HIV-1 Viral Genome for a Cure of AIDS," AIDS, 30(8):1163-1174.
Zetche et al. (Feb. 2015) "A Split Cas9 Architecture for Inducible Genome Editing and Transcription Modulation," Nature Biotechnology, 33(2):139-142.
Zhang et al. (Oct. 5, 2015) "CRISPR/gRNA-Directed Synergistic Activation Mediator (SAM) Induces Specific, Persistent and Robust Reactivation of the HIV-1 Latent Reservoirs," Scientific Reports, 5:1-14.
Zhu et al. (2015) "The CRISPR/Cas9 System Inactivates Latent HIV-1 Proviral DNA," Retrovirology, 12(22):7 pages.
Xie et al., "sgRNAcas9: a software package for designing CRISPR sgRNA and evaluating potential off-target cleavage sites," PloS one 9.6 (2014): e100448 (2014).

* cited by examiner

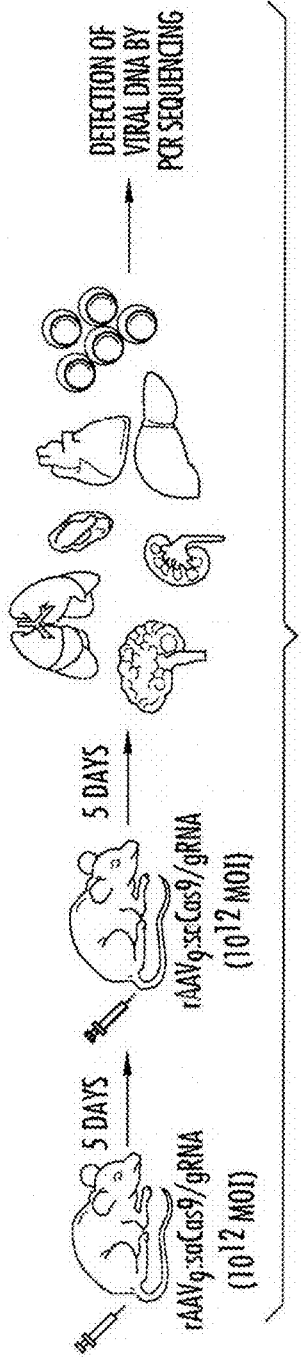
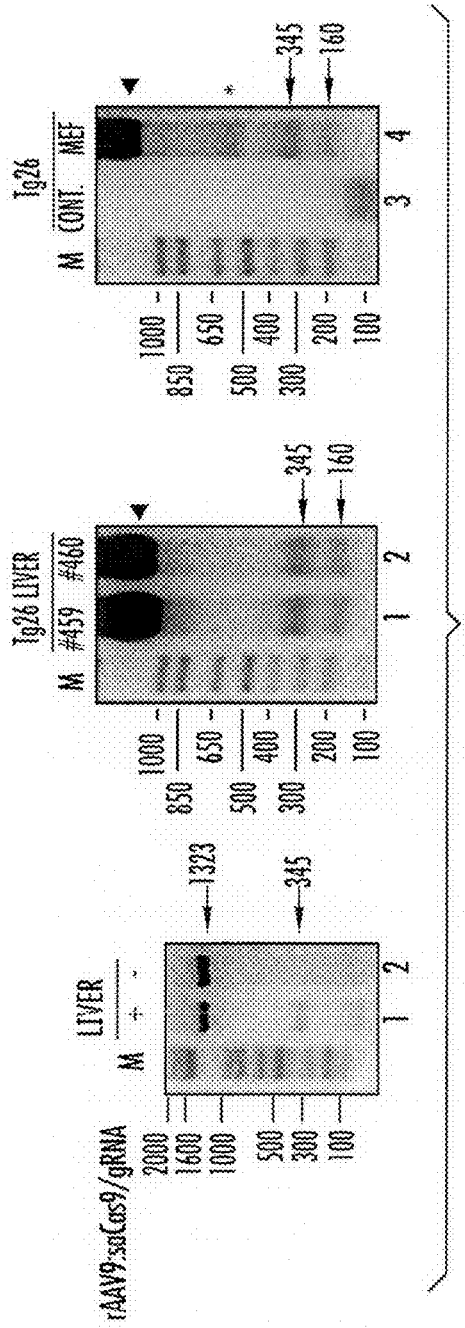
FIG. 2A
FIG. 2B

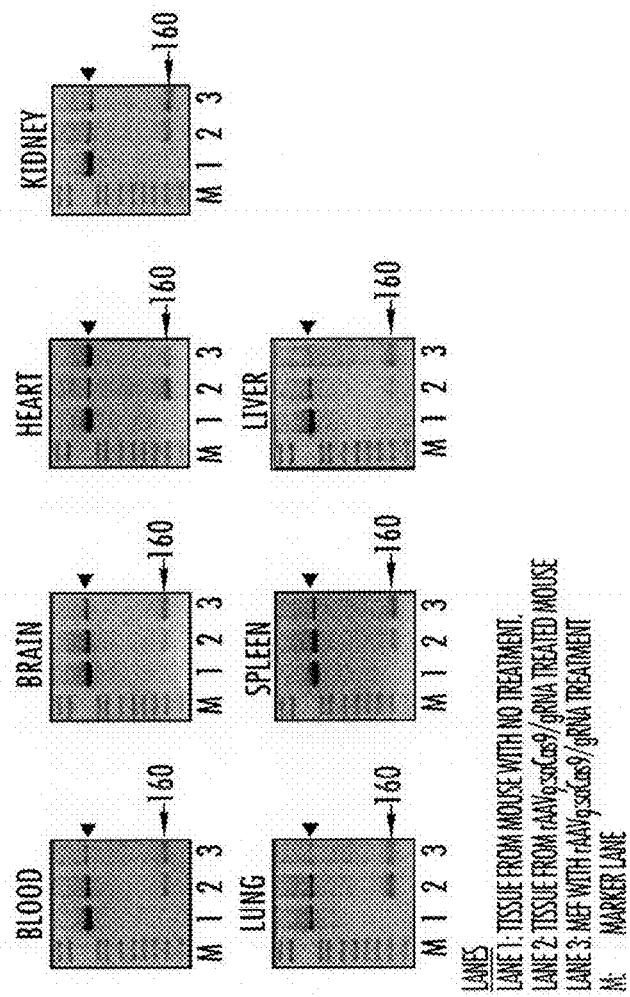

FIG. 3A

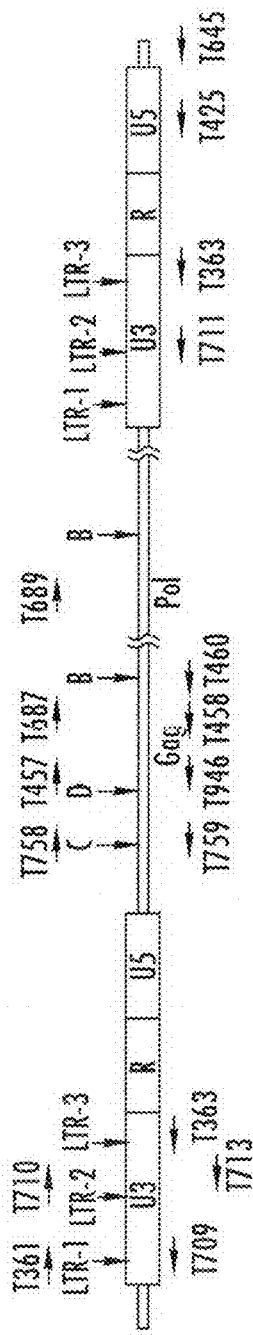
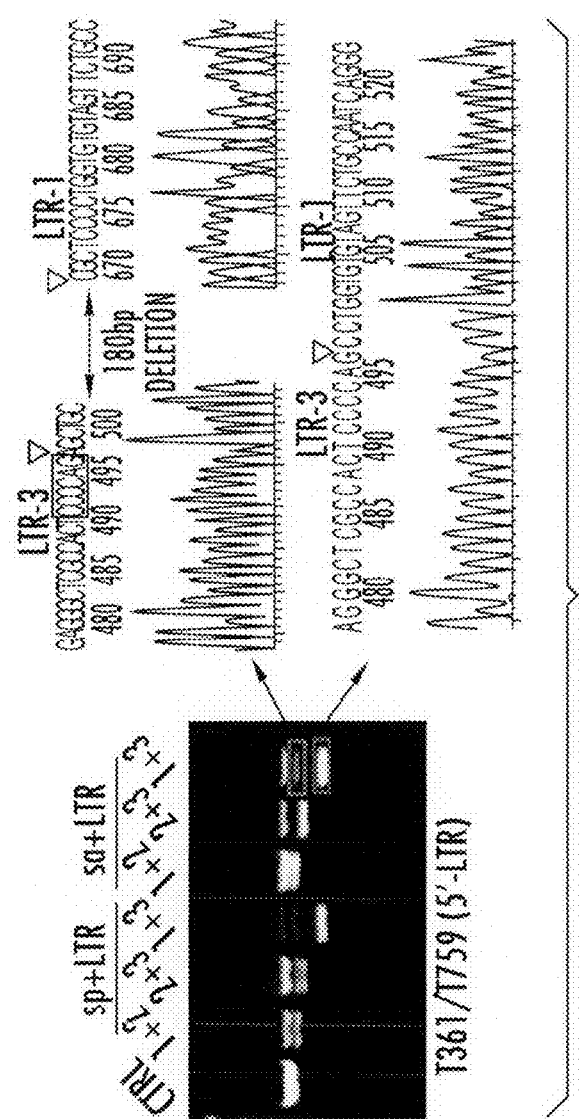
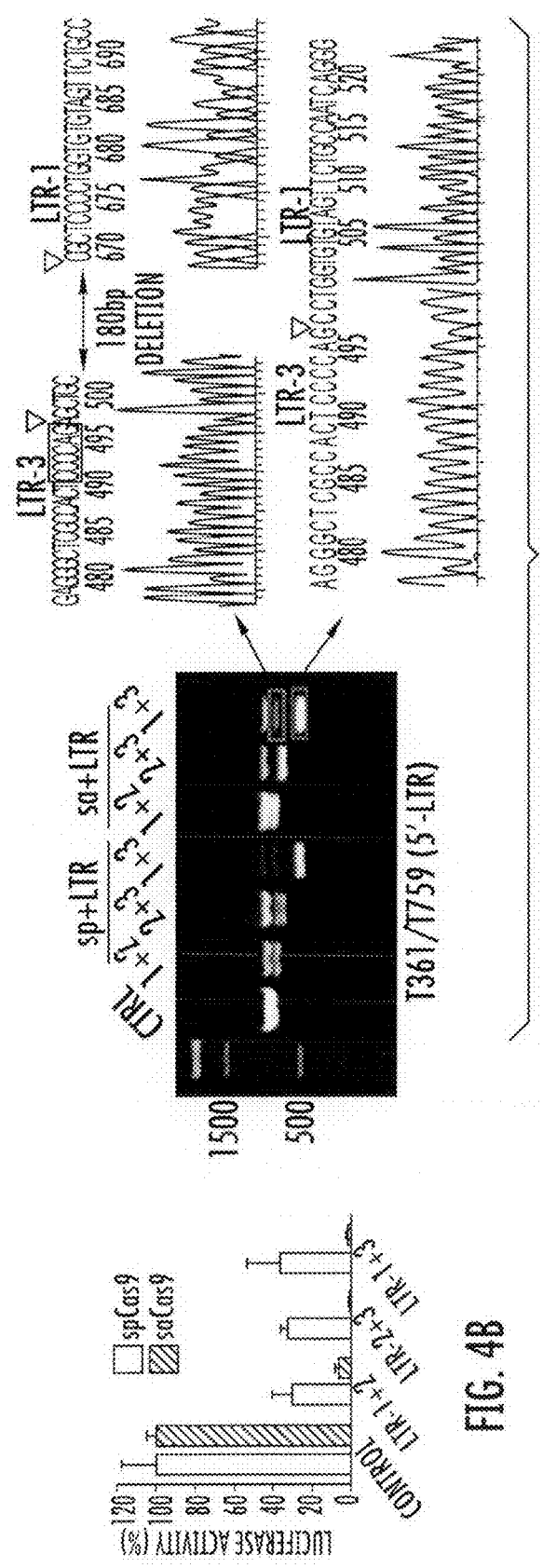
FIG. 4A
FIG. 4B
FIG. 4C

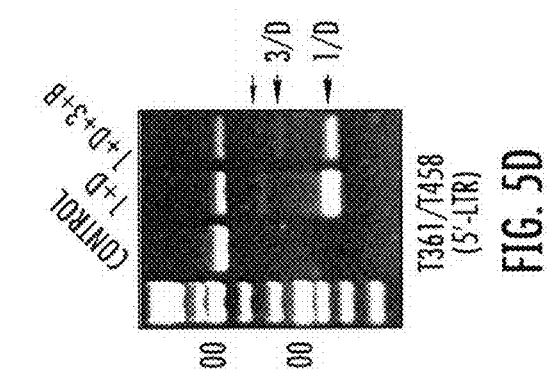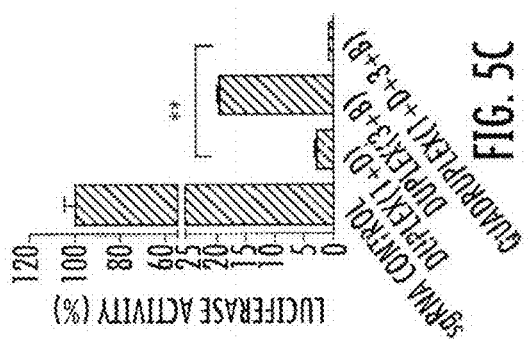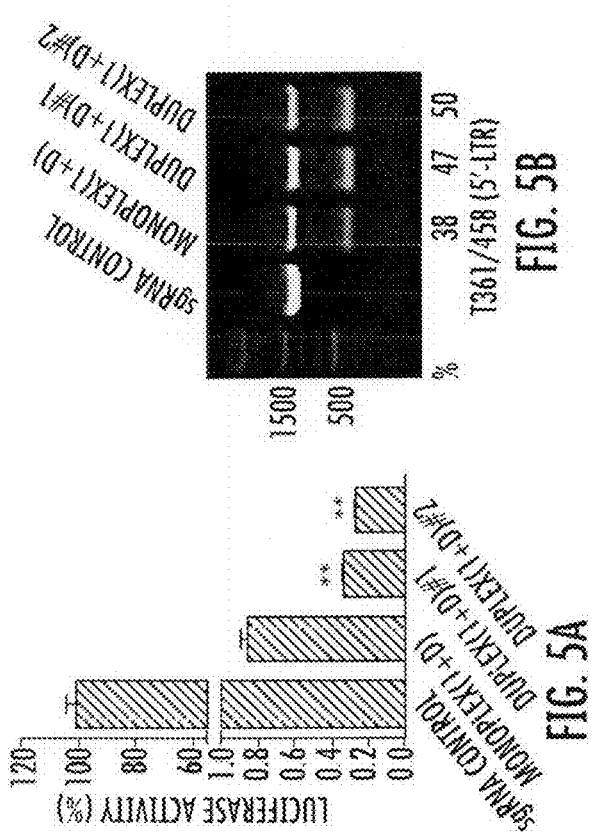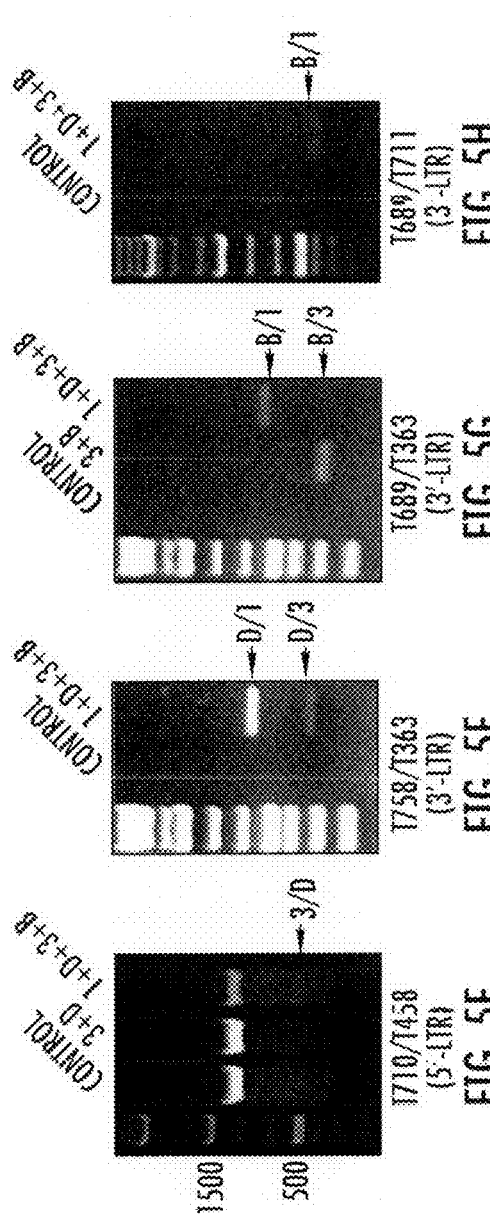
FIG. 5A FIG. 5B FIG. 5C FIG. 5D FIG. 5E FIG. 5F FIG. 5G FIG. 5H FIG. 5I

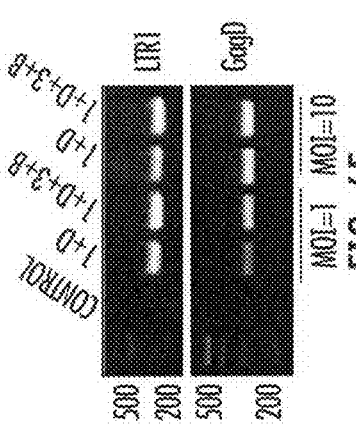
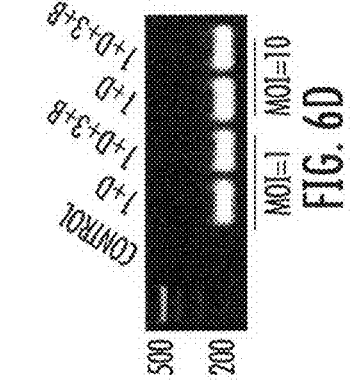
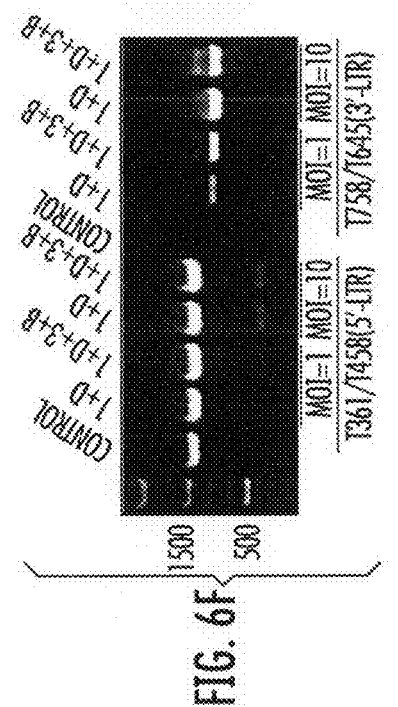
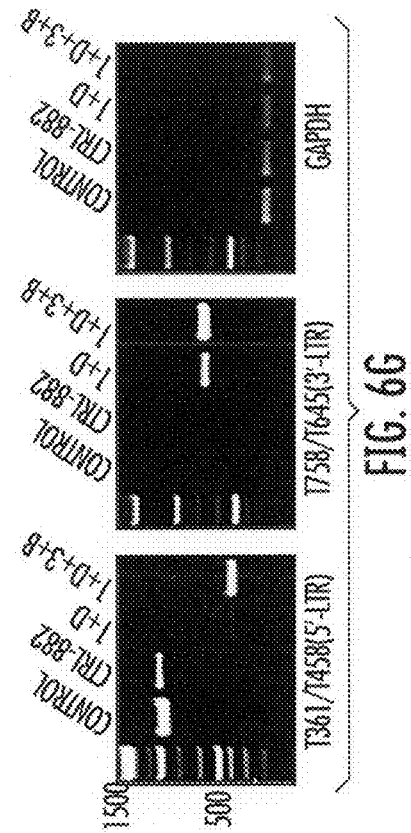
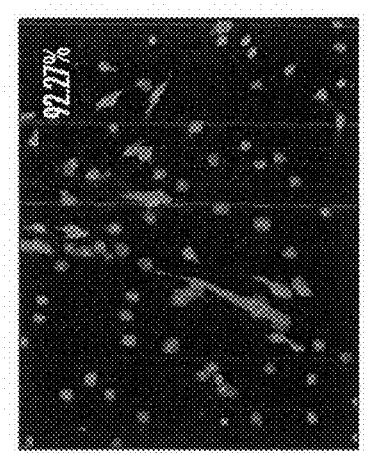
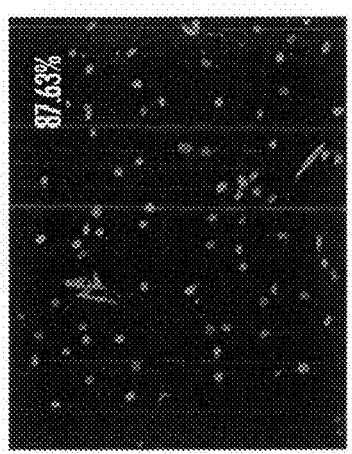
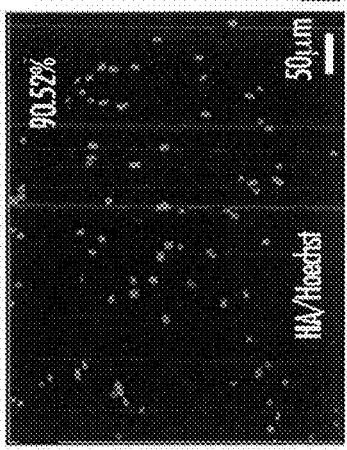

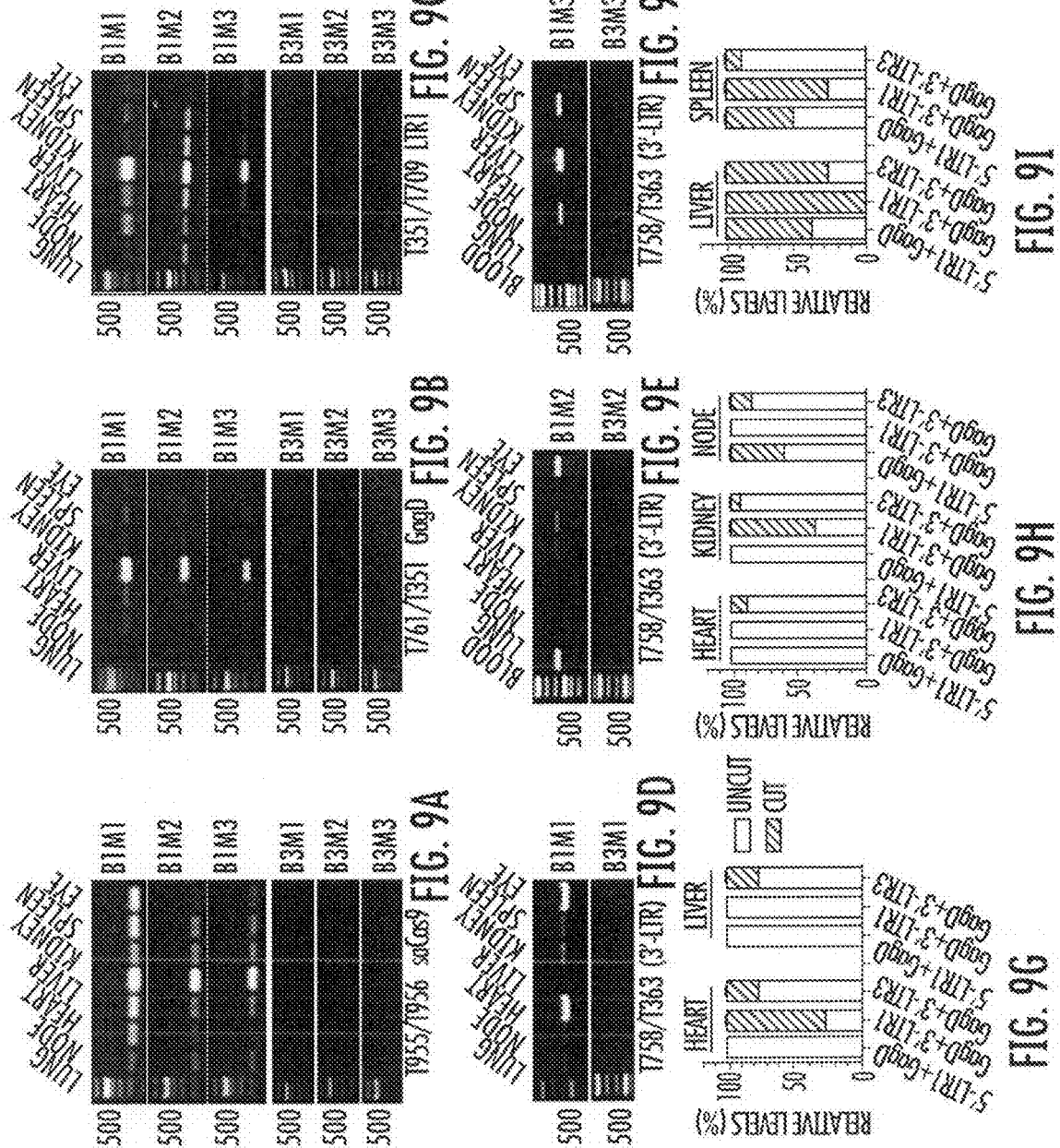

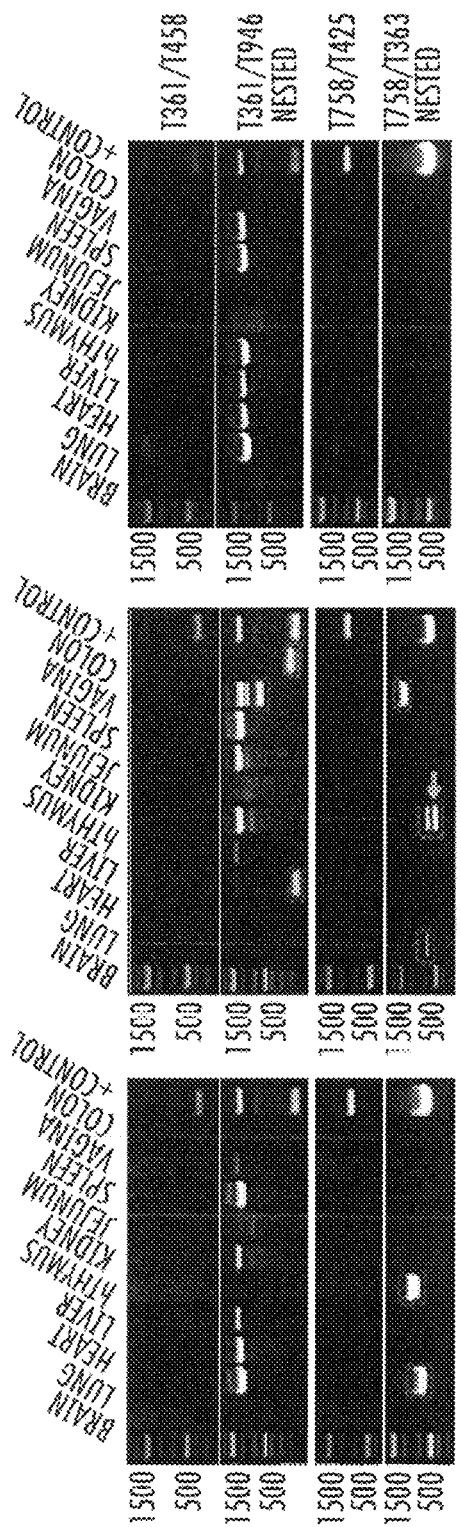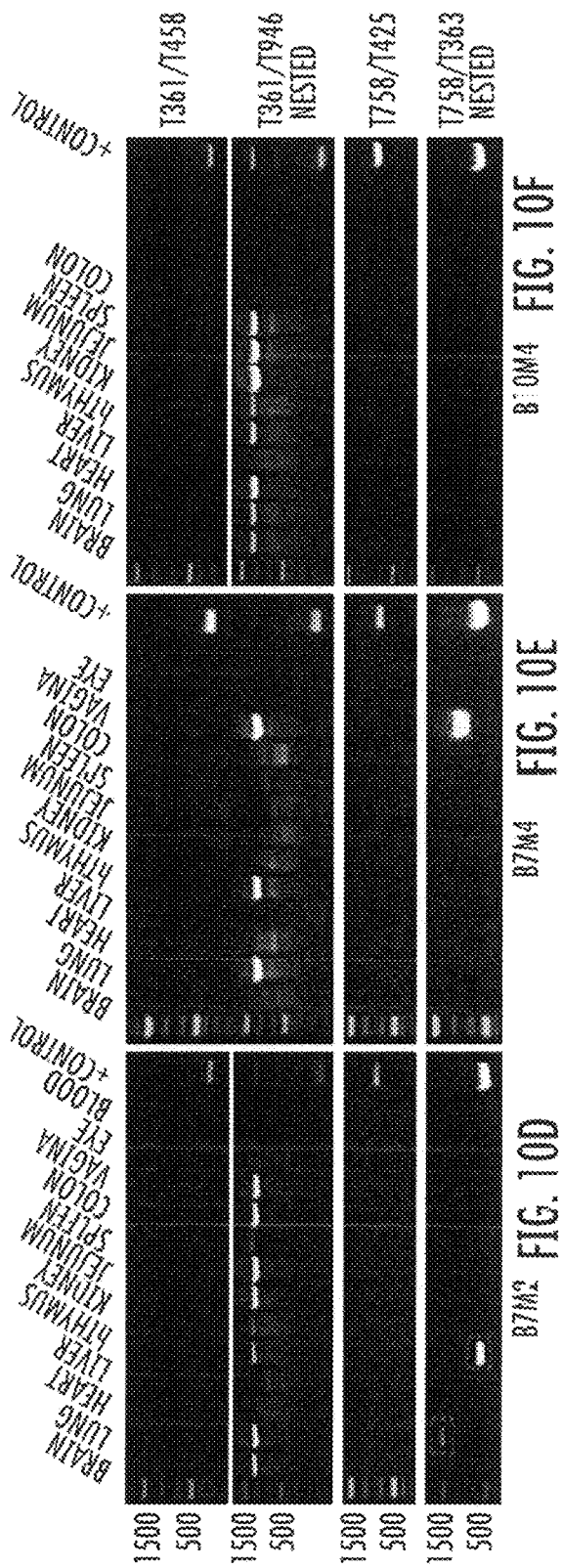
FIG. 10A B5M2
FIG. 10B B5M3
FIG. 10C B6M3
FIG. 10D B7M2
FIG. 10E B7M4
FIG. 10F B10M4

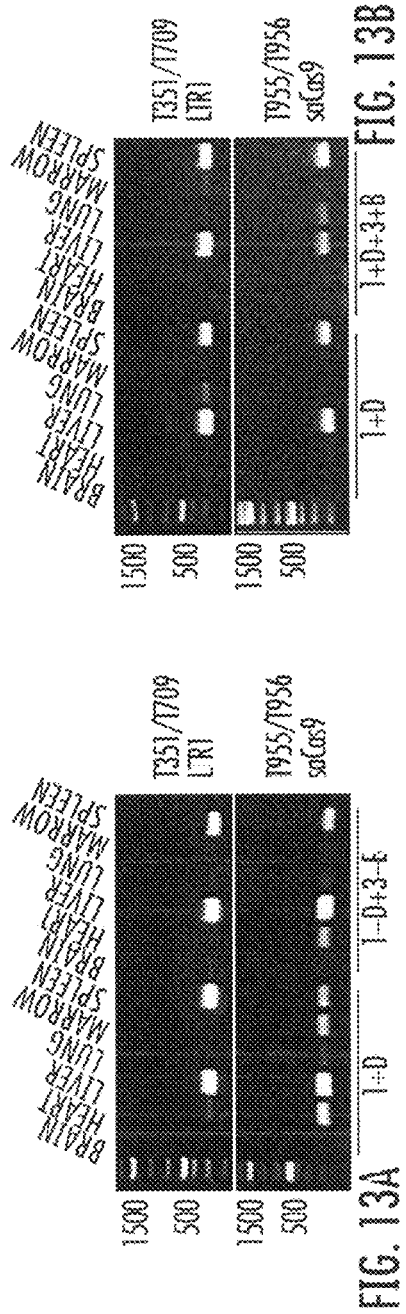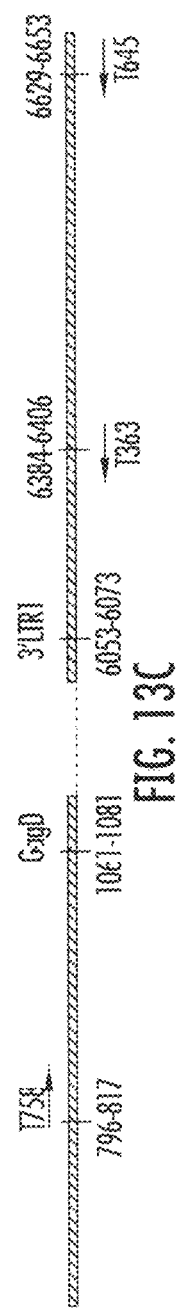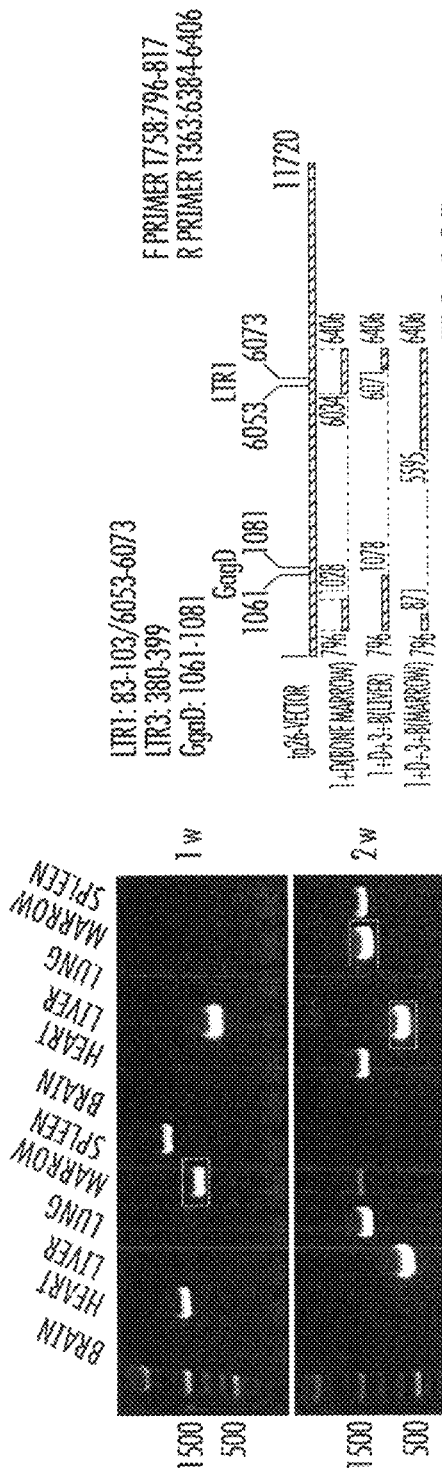

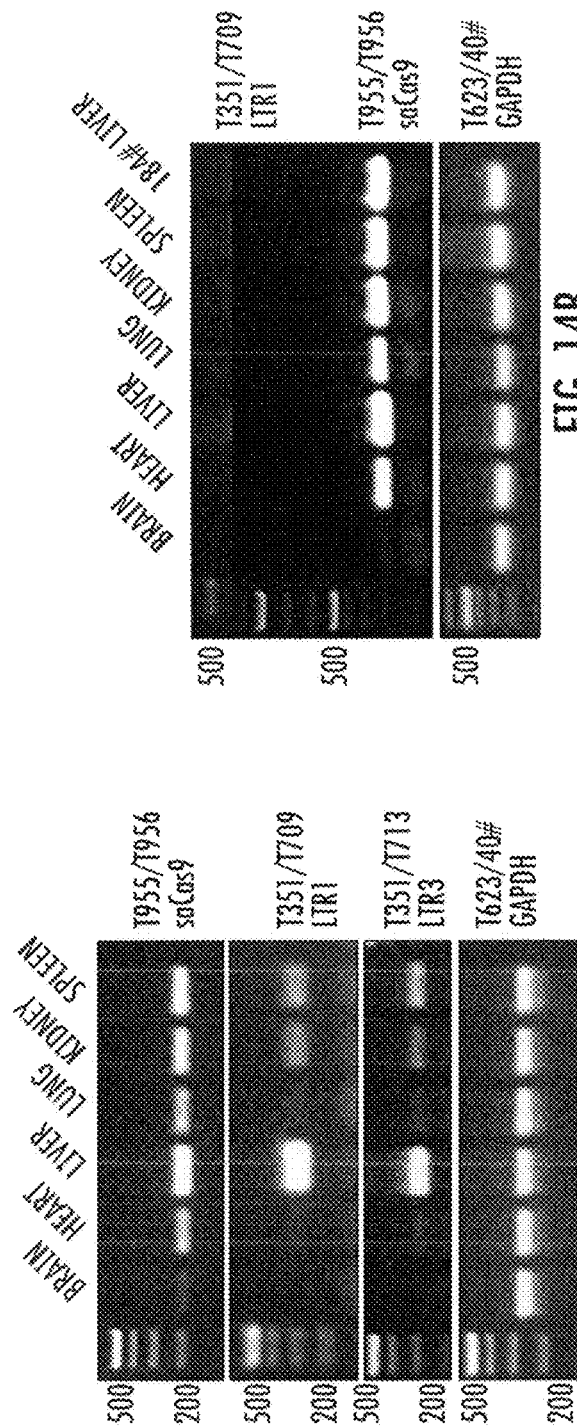
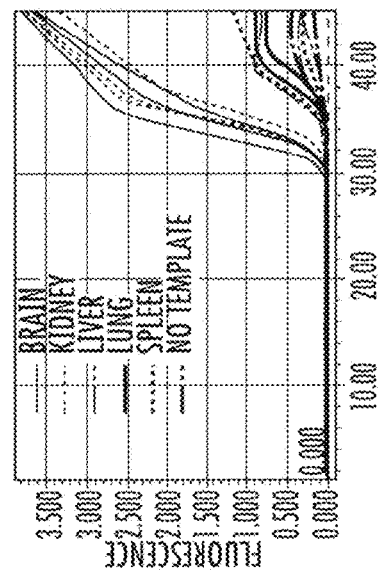
FIG. 14A
FIG. 14B
FIG. 14C

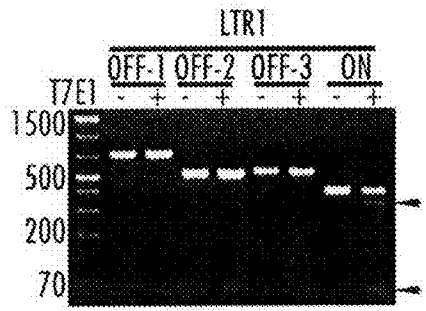

FIG. 17A

LTR1-OFF-1 (100% MATCH TO NUCLEOTIDE 7-23)

TCAGCCATGAGGAAGAACTTGGACAGCAGTGTGGCCCCTAAGGGAGAGAAAGGAGATCCA
AATCAGAGAGCCCTGTCCAAGTACAGTTTGGGTAGGGGCATTGCACAGCTTTGAGTGA
TATTCCACTGCTGCTGACATGATACCCTCATGACTCTGAGATTCGTTTCTCTCTCGTC
ATACTAAAGGCCCTATAGAGATAGAATATTCCAGAACAAACAGCCAGTGCTGAGCGTCCA
GCCGCATAGAGCTCAGCTCACAGCTCACAAACAGCTTGGTAAACATCTGTTGGTGTCCCC
AGGATGGTGTCTCCCGAGCCATTCTTGTGGCTGTAAGGCCCAGACAGCATGCTCTCT
GTACACACCAGGGCAGGAAAAGATCCAGCCCGCACTGGGCTTCCAGCATAGCTAGCTAA
GCTGGGACAGAGAAAGCCAGACTTAGGACTTCCCTTTGTTGTTTTTCTCAATGCCTCAAC
CAAAACACACAAAGGGAAGGTGTCTTTACACAGGCAGGAGGAAGCAGGCCCCTACTCTTGA
CACCCACTTAACAGTAGGGCTGGCAATGCCAGCCCAGAGCTTGTGTCTCCTCACAGCAGAA
GACAGCAAAAGGCTTCTGCAATCCAGCTCACTGGGGACCAGGGAAGGGTGACTTTGGGTTA
AAGAAGACCCTGACTCTCAGGCCTGGCTTGACCTTGCCAGCACTCTGGAGA

FIG. 17B

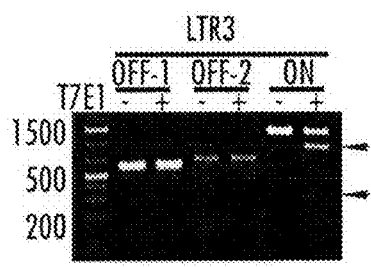

FIG. 17C

LTR3-OFF-1 (100% MATCH TO NUCLEOTIDE 8-23)

AGCCACACTCTGGCACTGAGACAAGTTGCCGGTAATTACCCCGAGTCCCACTCCTCTCT
GGGGCAGAGCACATCCACCACAGCTTCCTCCTGGGAAAGCGAGAGACAGCCTCCTGCGG
TTCCTCAAACCAAAGTCTGCCCTGAGATGCCAACCTTTAACTCAAAATCGAACATCCA
CTTTAATCTTTGGGGTTCTTTAGAATGGGAGAAGCCCTTTCTACTCTCCCATCTCCTAC
CCCCACCCAGTCCCGCCCAGATGCCTGGTTCTGCCTCCTGTTGATACCTTGAGCCTCA
CCAATCAGCACCTGGGCCTTCTGGGCTCCCACTGGGACCATGCCTCCTGCCCATCCCA
CAACTGTTTCTTGCATAACTGTATCACTCCCATTTCACAGGACTGGGAGGTAAAGAG
AATCTACACTAGATGATAAAAGGCTTTTGCTCTCGTTGTGGTGTGGGAATCAAATCCAAG
GCCTCTTACAAGCCAGGAAAAGAGGGCCTGTTTCTTTGCTTTTTTTGGAGACATGGTT
TCACTATGCAGACCTTTAACTCATAGAGATCCCCTGCCCTCTCCATACCTATGCTTACT

FIG. 17D

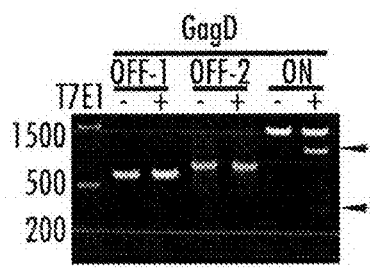

FIG. 17E

GagD-OFF-1 (100% MATCH TO NUCLEOTIDE 6-23)

TTGAAGCAGAGTTAAGGAATCTTGGGCTTCTCTCTGGCCCCTTTGTGCAATGATCTAGCG
TTAATCCACTCCTTCAGGGACTTACAACTGTTATAAAATGGTCAACATTCAAATAGAACC
TGTACAAAGGAAGCCTAAGGAAGAAATTGGAGGGGCAAGGGGCCCTAGGACCCTATAAAT
ATCCCTCCCGGCCAGGTCAGAGAACCACCCTTGGAGTCCCTGTCATTCCATTGGTGGGAG
CTCATTGTCTCTTCTAATGGTTTCTCATTTTCATTCATTTTCCCCATTTCAATCTGTAAC
TTACTGTCAGGGTCAGGCCTATAAGTGTTACTACTAGTAAAAGACACCAGGGTCTCTG
AATGAACTCTGCAATTATCTGTCACATTGTCTCTGACTCACGTCAGTAACTGTTATTGTT
TGGGATCTCCATGATCTAAACTACTTTATTGTCATCGGATGATCCTTCATGCCCTAT
ATCTCAGTTTAGATCCTGTTATTTCCTTAACTTGCCCTCCAATTCATACTTTAATTTCTT
CTTTGAGTGGTTCTTTACACCCTTCTTTCTATGATTACAGAAGGAACATGGCA

EXCISION OF RETROVIRAL NUCLEIC ACID SEQUENCES

CROSS-REFERENCE TO RELATED APPLICATIONS

This application is a National Phase application filed under 35 U.S.C. 371 of PCT International Application No. PCT/US2017/017652 with an International Filing Date of Feb. 13, 2017, which claims the benefit of priority to U.S. Provisional Application No. 62/410,496, filed Oct. 20, 2016, which claims the benefit of priority to U.S. Provisional Application No. 62/363,625, filed Jul. 18, 2018, which claims the benefit of priority to U.S. Provisional Application No. 62/345,520, filed Jun. 3, 2016, which claims the benefit of priority to U.S. Provisional Application No. 62/337,994, filed May 18, 2016, which claims the benefit of priority to U.S. Provisional Application No. 62/298,722, filed Feb. 23, 2016, which claims the benefit of priority to U.S. Provisional Application No. 62/295,390, filed Feb. 15, 2016, the entire contents of each of which are incorporated herein by reference.

STATEMENT REGARDING FEDERALLY SPONSORED RESEARCH

This invention was made with government support under P30 MH092177, P01 DA037830, RO1 NS087971, and RO1 MH092371 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 16, 2022, is named 348382_02601_SL.txt and is 58,730 bytes in size.

FIELD OF THE INVENTION

Embodiments of the invention are directed to gene-editing complexes and in vivo delivery vehicles for the prevention or treatment of infections by retroviruses. In particular, the gene-editing complexes comprise Clustered Regularly Interspaced Short Palindromic Repeat (CRISPR)-associated endonucleases encoded by a recombinant viral vector.

BACKGROUND

HIV/AIDS remains a major public health problem, as over 40 million people worldwide are infected and new infections continue at greater than two million/year (Adejumo O A, et al. *J Int AIDS Soc* 2015; 18:20049). Combination antiretroviral therapy (cART) effectively controls ongoing viral replication and can restore lost numbers of CD4+ T-cells. However, treatment fails to eliminate virus from latently infected cells (Kulpa D A, Chomont N. *J Virus Erad* 2015; 1:59-66). In subsets of resting CD4+ memory T-cells, integrated proviral DNA persists and can be reactivated to produce replication-competent virus. This can result in rapid viral rebound when cART ceases (Coffin J M. *Science* 1995; 267:483-489; Coffin J M. *AIDS* 1996; 10 (Suppl 3):575-84). Therefore, infected people must maintain life-long treatment due to viral persistence in cell reservoirs. Elimination of latent proviral DNA remains enigmatic. During latency, HIV-1-infected cells produce little or no viral proteins, thereby avoiding host antiviral immune clearance or direct viral cytopathicity. Eradication of virus requires its clearance and prevention of re-infection of latently infected cell CD4+ T effector memory cells (Saleh S., et al. *Blood* 2007; 110:4161-4164; Swiggard W J., et al., *J Virol* 2005; 79:141799-14188) amongst other infected lymphocytes and monocyte-macrophages present in spleen, lymph nodes, brain, genitourinary tract and gut to achieve a disease "cure" (Lusic M, Giacca M. *J Mol Biol* 2015; 427:688-694).

SUMMARY

Embodiments of the invention are directed to compositions comprising gene editing complexes, specific for retroviral nucleic acid sequences, and administration of these gene editing complexes to subjects in need of such treatment.

In one embodiment, a composition comprises a viral vector encoding a gene editing agent and at least one guide RNA (gRNA) wherein the gRNA is complementary to a target nucleic acid sequence of a retrovirus gene sequence, a target nucleic acid sequence encoding a retrovirus group specific antigen, a coding region, non-coding region or combinations thereof.

In another embodiment, a viral vector comprises an adenovirus vector, an adeno-associated viral vector (AAV), or derivatives thereof. Preferably, the adeno-associated viral vector comprises AAV serotypes 1, 2, 3, 4, 5, 6, 7, 8, 9, 10, 11, DJ or DJ/8. In one embodiment, the AAV vector is AAV serotype 9. ($AAV_9$).

In another embodiment, the gene editing agent is a Clustered Regularly Interspaced Short Palindromic Repeated (CRISPR)-associated endonuclease, or homologues or orthologs thereof. In one embodiment, the CRISPR-associated endonuclease is Cas9 or homologues or orthologs thereof.

In another embodiment, the gRNA is complementary to a long terminal repeat (LTR), a group-specific antigen or combinations thereof of the retrovirus gene sequence. In one aspect of the invention, the target sequence comprises a sequence within the long terminal repeat (LTR) of the human immunodeficiency virus. Preferably, the sequence within the long terminal repeat of the human immunodeficiency virus comprises a sequence within the U3, R, or U5 regions.

In some embodiments, the group specific antigen comprises human immunodeficiency virus coding and/or non-coding nucleic acid sequences. In one embodiment, the group specific antigen comprises at least one human immunodeficiency virus nucleic acid sequence comprising: gag, pol, env, tat, rev, nef vpr, vif vpu, tev or fragments thereof.

In one embodiment, the composition further comprises a sequence encoding a transactivating small RNA (tracrRNA). In one aspect of the invention, the transactivating small RNA (tracrRNA) sequence is fused to the sequence encoding the guide RNA. In another aspect, the composition comprises a sequence encoding a nuclear localization signal.

In yet another embodiment, an expression vector comprising an isolated nucleic acid encoding a gene editing agent and at least one guide RNA (gRNA) wherein the gRNA is complementary to a target nucleic acid sequence of a retrovirus gene sequence, a target nucleic acid sequence of a group specific antigen or combinations thereof.

In yet another embodiment, an isolated nucleic acid sequence comprises a Clustered Regularly Interspaced Short Palindromic Repeat (CRISPR)-associated endonuclease; a first guide RNA (gRNA) having a first spacer sequence that is complementary to a first target protospacer sequence in a proviral DNA; a second gRNA having a second spacer sequence that is complementary to a second target protospacer sequence in the proviral DNA, wherein the first target protospacer sequence and the second target protospacer sequence are situated in a long terminal repeat (LTR) of the proviral DNA. In some embodiments the isolated nucleic acid sequence targets multiple target sequences and excises intervening viral sequences between the two or more target sequences.

In yet another embodiment, an expression vector encoding an isolated nucleic acid sequence comprises a Clustered Regularly Interspaced Short Palindromic Repeat (CRISPR)-associated endonuclease; an isolated nucleic acid sequence encoding a first guide RNA (gRNA) having a first spacer sequence that is complementary to a first target protospacer sequence in a proviral DNA; and an isolated nucleic acid sequence encoding a second gRNA having a second spacer sequence that is complementary to a second target protospacer sequence in the proviral DNA, wherein the first target protospacer sequence and said second target protospacer sequence are situated in a long terminal repeat (LTR) of the proviral DNA.

In yet another embodiment, a method of method of inactivating a retrovirus in a subject comprising administering to the subject a composition comprising an expression vector encoding a Clustered Regularly Interspaced Short Palindromic Repeated (CRISPR)-associated endonuclease, or homologues thereof and one or more guide RNAs, wherein the guide RNA is complementary to a target nucleic acid sequence in the retrovirus.

In yet another embodiment, a method of treating a subject having a human immunodeficiency virus infection or reducing the risk of a human immunodeficiency virus infection in a subject at risk for a human immunodeficiency virus infection, the method comprising administering to the subject a therapeutically effective amount of a composition comprising an expression vector encoding a Clustered Regularly Interspaced Short Palindromic Repeated (CRISPR)-associated endonuclease, or homologues thereof and one or more guide RNAs, wherein the guide RNA is complementary to a target nucleic acid sequence in the retrovirus.

Other aspects of the invention are described infra.

BRIEF DESCRIPTION OF THE FIGURES

FIG. 1A is a schematic illustration of HIV-1 highlighting the position between the Gag and Pol genes (3100 bp) that was removed to create a transgene for developing Tg26 animals. The positions of gRNAs LTR 1 and Gag D, and their nucleotide compositions are shown. Red letters indicate the PAM sequence. The top left of the diagram shows the positions of the primers used for PCR (P1 and P2) and nested PCR (P1' and P2') with the expected amplicons before and after excision. FIG. 1A discloses SEQ ID NOS 91-92, respectively, in order of appearance. FIG. 1B is a depiction of MEFs derived from Tg26 and results from gel analysis of PCR amplification of HIV-1 DNA after treatment with increasing amounts of rAAV9:Cas9/gRNAs. The position of full-length (1323 bp) and the truncated (345 bp) PCR products are shown.

FIGS. 2A-2D depict the in vivo excision of HIV-1 DNA by rAAV9:saCas9/gRNA in various tissues of Tg26 mice. FIG. 2A is a schematic illustration of the procedure used for the inoculation of rAAV9:Cas9/gRNAs and the organs used for the analysis. FIG. 2B shows the results from PCR of DNA obtained from lines of Tg26 mice with and without rAAV9 shows the positions of 1323 bp and the truncated 345 bp in the rAAV9 treated samples (left). Gel analysis of PCR products using two pairs of primers; P1/P2 for detection of 345 bp fragment and the nested primers P1'/P2' for detection of the 160 bp fragment. The full-length PCR product is shown by an arrowhead (middle). Results from double primer PCR amplification of the MEF DNA again showing the expected two truncated HIV-1 DNA fragments. The position of the full-length amplicon (arrowhead) and a non-specific band (asterisk) are shown. Control (Cont.) illustrates PCR reaction in the absence of primers (right). FIG. 2C shows the results from sequencing of the 160 bp DNA fragment shown in Panel B (middle and right panels). The positions of the primers as well as gRNAs LTR 1 and Gag D are shown. FIG. 2C discloses SEQ ID NOS 93-104, respectively, in order of appearance. FIG. 2D shows the results from PCR amplification of DNA from various tissues (lanes 1 and 2) and MEFs (lane 3) demonstrating the absence of the 160 bp truncated DNA fragment in animals with no inoculation of rAAV9:saCas9/gRNAs and the detection of this band in the animals and cells that received rAAV9:saCas9/gRNAs.

FIGS. 3A, 3B show the elimination of segments of the integrated HIV-1 DNA from rat blood cells after inoculation with rAAV9:saCas9/gRNA and expression of viral RNAs. (FIG. 3A) Total DNA from circulating lymphocytes of the control (untreated) and experimental (treated with rAAV9:saCas9/gRNA) rats was prepared and used for PCR amplification using a set of primers derived from the 5'-LTR and Gag gene (shown in Materials and methods). After gel electrophoresis, a short DNA fragment of ~198 bp was detected in the treated, but not the control samples, which were then purified and cloned in a TA vector. Several clones were selected for DNA sequencing. Four representative DNA sequences (C1-C4) obtained from each animal were aligned to the reference LTR-Gag region of the HIV-1 pNL4-1 sequence. The positions and nucleotide composition of LTR 1 and Gag D target sequences are highlighted in green, PAM in red and LTR specific primers using PCR are highlighted in blue. FIG. 3A discloses SEQ ID NOS 105-131, respectively, in order of appearance. (FIG. 3B) Total RNA prepared from circulating lymphocytes and lymph nodes of transgenic rats, control (untreated) and treated with rAAV9:saCas9/gRNA for 10 days were prepared and used for quantitative RT-PCR for detection of Gag RNA and Env RNA. Expression of β-actin in each assay was determined and the values were used as reference for quantification of viral RNA expression.

FIGS. 4A-4E show that the saCas9/sgRNA efficiently excises HIV-1 genome and suppresses HIV-1 luciferase reporter expression. FIG. 4A: Location of sgRNA target sites (red arrows) and PCR primers (black arrows). FIGS. 4B, 4C: Efficiency comparison between saCas9/sgRNA and spCas9/sgRNA system using EcoHIV-eLuc reporter assay (FIG. 4B) and direct PCR genotyping (FIG. 4C). Arrows pointed the representative fragmental deletion between LTR1 and LTR3 target sites and additional insertion, which were validated by TA-cloning and Sanger sequencing (FIG. 4C). FIG. 4C discloses SEQ ID NOS 132-134, respectively, in order of appearance. FIGS. 4D, 4E: Three LTR sgRNAs paired with viral structural sgRNAs induced robust inhibition of EcoHIV-eLuc activity by ONE-GLO Luciferase Assay (FIG. 4D) and fragmental deletion/insertion by direct PCR genotyping with indicated primers (FIG. 4E). The representative fragmental deletion in red box was corroborated with Sanger sequencing. HEK293T cells in 6 wells of the 96-well plate were cotransfected with pNL4-3-EcoHIV-firefly luciferase reporter (10 ng/well), pCMV-*renilla* luciferase reporter (2 ng/well) and indicated Cas9/sgRNA expressing vectors: for spCas9 system (FIG. 4B), pLV-EF1a-spCas9-T2A-RFP (80 ng/well) and indicated sgRNA expression vectors (60 ng/well each for paired gRNAs); for saCas9 system (FIGS. 4B, 4D), pX601-saCas9/LTR sgRNA expression vectors (100 ng/well each for indicted pairs). After 48 h, the firefly-luciferase activity in the cell lysates was measured with ONE-GLO™ Luciferase Assay System and the *renilla*-luciferase activity was measured with *Renilla* Luciferase Assay System. Data represent mean±SD of 4 independent transfections with percentage changes in firefly luciferase after *renilla*-luciferase normalization as compared with the corresponding empty pX601 vector. Additional 2 wells of the transfected cells were used for direct-PCR genotyping (FIGS. 4C, 4E). Similar experiments were repeated 2-3 times.

FIGS. 5A-5I show the efficacy of multiplex sgRNAs in all-in-one AAV vector. FIGS. 5A, 5B: Duplex sgRNAs/saCas9 exhibited stronger inhibition of EcoHIV-eLuc activity (FIG. 5A) and excision of HIV-1 genome (FIG. 5B). The ratio indicates the density of the fragmental deletion band over the wild-type band (FIG. 5B). FIGS. 5C-5I: Quadruplex sgRNAs/saCas9 exhibited stronger inhibition of Eco-HIV-eLuc activity (FIG. 5C) and higher excision efficiency at both 5'-LTR1/LTR3 with GagD (FIGS. 5D, 5E) or GagD/PolB with 3'-LTR (FIGS. 5F-5I). The primer T361/T458 (FIG. 5D) detected fragmental deletions between 5'-LTR1/LTR3 and GagD (black arrows) and additional insertion was observed in both duplex and quadruplex groups (red arrow). T710/T458 detected the deletion between 5'-LTR3 and GagD (FIG. 5E). Deletions between GagD or PolB and 3'-LTR1/LTR3 were detected by the primer T758/T363 (FIG. 5F) and T689/T363 (FIG. 5G) respectively. The primer pair T689/T711 detected the deletion between PolB and 3'-LTR1 (FIG. 5H). The genomic DNA was normalized with saCas9 and β-actin. HEK293T cells in 96-well plate were cotransfected with EcoHIV-eLuc reporter plus two individual monoplex sgRNA expressing vectors (100 ng each), one duplex sgRNA expressing vector (100 ng) with an empty pX601 vector (100 ng) for equal amount to the sgRNA control group (200 ng, FIGS. 5A, 5B), or one duplex/quadruplex sgRNA expressing vector and the sgRNA control (100 ng each, FIGS. 5C-5I). After 48 h, ONE-Glo Luciferase Assay (FIGS. 5A, 5C) was performed as described in FIGS. 4A-4E, and direct PCR genotyping (FIGS. 5B, 5D-5I) was performed using indicated primer pairs.

FIGS. 6A-6G show that AAV-DJ-mediated delivery of multiplex sgRNAs/saCas9-expressing vector effectively excises HIV-1 integrated genome in neural stem cells (NSCs) from Tg26 transgenic mice. Similar infection efficiency of monoplex (FIG. 6A), duplex (FIG. 6B) and quadruplex (FIG. 6C) in NSCs at 20 d postinfection with a 10 functional MOI (fMOI). The infected cells were determined by immunofluorescent cytochemistry with anti-HA tag antibody. FIGS. 6D-6F: Direct PCR analysis validated dose-dependent delivery of transgene saCas9 (FIG. 6D) and LTR1/GagD (FIG. 6E) and excision of 5'-LTR/GagD and GagD/3'-LTR (FIG. 6F) at 2 d postinfection. (FIG. 6G) Quadruplex sgRNAs/saCas9 showed stronger cleavage efficacy than the duplex sgRNAs/saCas9 at 20 d postinfection with 10 fMOI. The primers T361/T458 detected the deletions between 5'-LTR1/LTR3 and GagD, and the primers T758/T645 detected the deletions between GagD and 3'-LTR1/LTR3 (FIGS. 6F, 6G). GAPDH was used for normalization of genomic DNA. Control-882 AAV-DJ virus was used as a nonfunctional control.

FIGS. 7A, 7B: Tg26 mice were injected via the tail vein with purified AAV-DJ/8 virus ($1.535 \times 10^{12}$ GC/mouse). Two weeks after injection, mice were euthanized and their tissues were collected for genomic DNA extraction and PCR genotyping. The positive control represented the excision of EcoHIV-eLuc reporter in HEK293T cells transfected with AAV-saCas9/sgRNA (LTR1+GagD) vector. The negative control represented the mice injected with mock AAV virus. FIG. 7C: Additional injection of AAV-DJ/8 at 2 weeks after first injection was given and 2 weeks later tissue samples were harvested for PCR genotyping with indicated primers. The representative deletion fragments (red box) were verified with TA-cloning and Sanger sequencing (see FIGS. 16A, 16B). FIG. 7D: Diagram showing the location of RT-qPCR primer pairs for HIV transcripts. FIGS. 7E-7G: RT-qPCR analysis showing robust decrease (p<0.001) in the levels of HIV-1 RNA transcripts in sgRNAs/saCas9 treated mice as compared with the control mice injected with mock AAV virus. Data represents mean SD of triplicate experiments after normalization with house-keeping gene Ppia.

FIG. 8A: AAV-DJ/8 was administered via retro orbital injection into the blood sinus of the right eye of each mouse (n=3) right after EcoHIV-eLuc inoculation via the same injection route. Representative bioluminescence imaging of one mouse on days 6, 9, 12 and 19 post EcoHIV inoculation was shown. All the images were measured for radiance (photon/second/Sr2) and pseudocolored with the same rainbow scale for fair comparison. FIG. 8B: Total flux of bioluminescence (total photons/second, P/S) measured from the entire body of each group (n=3/group until Day 19 (n=2)) on each indicated day post EcoHIV-eLuc inoculation. FIG. 8C: Bioluminescence output from EcoHIV-eLuc infected cells in each mouse was measured from the region of interest (ROI) defined on the right eye for comparison. Data represents mean±standard deviation with statistical significance indicated by "*" in each comparison (P<0.05, Student's one-sided t test). FIG. 8D: The bioluminescence output from the neck lymph node of each mouse (n=3 until Day 19 (n=2)) was used for comparison of the efficacy of saCas9/gRNA treatment longitudinally on HIV excision (P-values are two-sided using linear-mixed effects model).

FIGS. 9A-9I show that PCR genotyping and qPCR analysis validated the gene transduction and excision efficiency of EcoHIV-eLuc by quadruplex sgRNAs/saCas9 AAV-DJ/8 in various organs/tissues of mice. FIGS. 9A-9C: Various extent of gene transduction in indicated tissues/organs for saCas9 (FIG. 9A), GagD (FIG. 9B) and LTR-1 (FIG. 9C) at 19 days after infection with quadruplex sgRNAs/saCas9 AAV-DJ/8 (upper panel) or empty control AAV-Cre-DJ/8 (lower panel). FIGS. 9D-9F: Conventional PCR genotyping showing various extents of EcoHIV DNA excision between GagD and 3'-LTR in each indicated tissues/organs (upper panel) compared with the negative control (lower panel). FIG. 9G-9I: Quantitative PCR analysis of three indicated fragmental excision types in different tissues/organs selected from B1M1 (FIG. 9G), B1M2 (FIG. 9H) and B1M3 (FIG. 9I). Data represent mean±SD of triplicate reactions and expressed as relative levels over the internal uncut (non-targeting) region of EcoHIV DNA in the same tissues/organs. The BxMx indicates the box and mouse number.

FIGS. 10A-10F show the excision of HIV proviral DNA by quadruplex sgRNAs/saCas9 AAV-DJ/8 in humanized BLT mice inoculated with HIV$_{NL-BaL}$-eLuc at 2 (FIGS. 10A-10C), 3 (FIG. 10D) and 4 weeks (FIGS. 10E, 10F) after AAV treatment. Conventional PCR (35 cycles) using primer pair T361/T458 (for amplifying 5'-LTR/Gag) was used to detect the presence of HIV proviral DNA, which showed a weak wild-type band (1.4 kb) in the lung tissue of the B6M3 negative control without saCas9/sgRNA treatment (FIG. 10C). Nested PCR (35 cycles) using primer pair T361/T946 (for 5'-LTR/Gag) with the template from the first round PCR (22 cycles with the primer pair T361/T458) identified the wild-type DNA fragment (1.13 kb) of HIV-1 proviral DNA in most, if not all, organs/tissues of each BLT mouse (FIGS. 10A-10F) and the PCR product of fragmental deletions resulted from HIV-1 excision in heart, colon and vagina of HIV-infected BLT mice treated with saCas9/sgRNA (FIG. 10A). Nested PCR with the primer pair T758/T363 (for Gag/3'-LTR) using the template from the first round PCR (25 cycle, T758/T425) identified the fragmental deletion bands in organs/tissues of saCas9/sgRNA-treated BLT mice (FIGS. 10A, 10B, 10D, 10E) but not the untreated BLT mice (FIGS. 10C, 10F). The fragmental deletion bands resulted from saCas9 editing were framed in red followed by TA-cloning and Sanger sequencing for validation (see FIGS. 20A, 20B, 21A, 21B). The BxMx indicates the box and mouse number. The positive control represented the excision of EcoHIV-eLuc reporter in HEK293T cells transfected with AAV-saCas9/sgRNA (LTR1+GagD) vector.

FIG. 11A: Schematics of the sgRNA target sites and PCR primer locations. FIG. 11B: Comparative analysis of 984 nucleotide deletion after precise cleavage at the third nucleotide from PAM (red text) in LTR1 and GagD. FIG. 11B discloses SEQ ID NOS 135-141, respectively, in order of appearance. FIG. 11C: Representative Sanger sequence tracing showing the editing/re-ligation site between LTR1 and GagD. FIG. 11C discloses SEQ ID NO: 142.

FIG. 12A: Summary of genomic and functional titer for monoplex (plasmid 822), duplex (plasmid 924 and 938) and quadraplex (plasmid 962) sgRNAs/saCas9 AAV-DJ. FIG. 12B: Representative images of immunofluorescent staining with anti-HA antibody at 2 days after 0.1 µl AAV-DJ virus infection in HEK293T cells plating on 96-well plate. The positive cells were counted in each of three wells and the functional titer was calculated as transduction units (TU) per ml. The genomic titer was determined by the viral genome copy number in 1 ml virus sample (GC/ml) by quantitative PCR analysis using the copy number of standard samples.

FIGS. 13A-13E show similar efficiency of transgene expression and HIV-1 genome excision in different organs/tissues of Tg26 transgenic mice infected with duplex and quadruplex sgRNAs/saCas9 AAV-DJ. FIGS. 13A, 13B: High efficiency of AAV delivery for saCas9 and representative sgRNA LTR-1 expression cassette in the liver and spleen of Tg26 mice intravenously injected with AAV-DJ virus (total 4.15-4.20×10$^{12}$ GC in 100 µl PBS/mouse) via tail vein at 1 week after infection (FIG. 13A) and one additional injection at 1 week after the first injection. Tissue samples were collected at 1 (FIG. 13A) and 2 weeks (FIG. 13B) after first injection. FIGS. 13C, 13D: Nested PCR analysis identified fragmental deletion in liver, heart, bone marrow and spleen. The representative deletion fragments (red box) were verified with TA-cloning and Sanger sequencing (FIG. 13E).

FIGS. 14A-14C show that quadruplex sgRNAs/saCas9 AAV-DJ/8 induced efficient transgene transduction (FIGS. 14A, 14B) and RT-qPCR analysis validated Tat transcription in various organs/tissues of HIV Tg26 transgenic mice. Tg26 mice were injected via the tail vein with purified AAV-DJ/8 virus (1.535×10$^{12}$ GC/mouse) for once (FIG. 14A) or twice (FIG. 14B) separated by two weeks. Two weeks after last injection, mice were euthanized and their tissues were collected for genomic DNA extraction and PCR genotyping for the cDNA encoding sgRNAs and saCas9 as indicated. FIG. 14C: Representative amplification curves showing relative Ct values for Tat transcription.

FIG. 16A discloses SEQ ID NOS 143-160, respectively, in order of appearance. FIG. 16B discloses SEQ ID NOS 161-187, respectively, in order of appearance.

FIGS. 17A-17F are results from a T7E1 mismatch cleavage assay showing no off-target effects in the liver tissue of Tg26 mice receiving a single intravenous injection of quadruplex sgRNAs/saCas9 AAV-DJ8. Representatives of the most potential off-target sites predicted for LTR1 (FIG. 17A, 17B), LTR3 (FIGS. 17C, 17D) and GagD (FIGS. 17E, 17F) were examined by T7E1 mismatch cleavage assay using the PCR product amplified from the genomic DNA extracted from the liver tissue of Tg26 mice at 4 weeks after sgRNAs/saCas9 treatment. The on-target PCR products were used as positive controls. Arrows indicated the InDel mutation patterns for the positive control PCR products generated with primer pairs T361/T363 for LTR1 (FIG. 17A), T361/T458 for LTR3 (FIG. 17C) and GagD (FIG. 17E). FIGS. 17B, 17D, 17F: A representative sequence of PCR product encompassing the predicted potential off-target sites in mouse genomic DNA. The PAM sequence is highlighted in red and the PCR primers are highlighted in green. FIG. 17B discloses SEQ ID NO: 188. FIG. 17D discloses SEQ ID NO: 189. FIG. 17F discloses SEQ ID NO: 190.

FIG. 18A: PCR genotyping with primers T758/T363 amplified the expected fragment with a deletion between GagD and 3'-LTR1. The deletion fragments in heart and lung indicated by red color frame were extracted from the gel for TA-cloning and Sanger sequencing. FIGS. 18B, 18C: Representative Sanger sequence showing the expected cleaving/re-ligation site (red arrows) between GagD and 3'-LTR1. The deletion occurred exactly at the third nucleotides from the PAM (highlighted red) in heart (FIG. 18B) and lung (FIG. 18C). FIG. 18B discloses SEQ ID NOS 191-198, respectively, in order of appearance. FIG. 18C discloses SEQ ID NOS 199-206, respectively, in order of appearance.

FIG. 20A: Schematics of the junction sequence and unexpected sequence inserted in between the predicted cleavage sites. Nested PCR products using primer T361/T946 (the template from the first round PCR with the primer T361/T458) were extracted from the gel for TA cloning and 2-5 clones were sequenced from each sample. The precise cleavage site at the third nucleotide from the PAM (highlighted red) is indicated by the scissors. The predicted deletion between the 5'-LTR1 and GagD as well as various additional insertions (green) or deletions (black dot line) were identified. The blue and pink solid bar indicate the cleaved residual sequence. The numbers above the fragments indicated the start and the end of the nucleotide sites. TA clones with stars are selected to show detail sequence and tracing. FIG. 20B: Representative Sanger sequencing tracing of clone B5M3-heart-1 shows the cleaving/relegation site (indicated by an arrowhead) between 5'-LTR1 and GagD. The conjunctive sequence between the 5'-LTR1 and GagD is highlighted with orange and green, respectively. The primer T361 and T946 sequence is highlighted with blue and yellow, respectively. FIG. 20A discloses SEQ ID NOS 207-211, respectively, in order of appearance. FIG. 20B discloses SEQ ID NOS 212-222, respectively, in order of appearance.

FIGS. 21A and 21B show the validation of the fragmental deletion of HIV-1 genome between GagD and 3'-LTR1 sites in the organs/tissues of humanized BLT mice after genome-editing. FIG. 21A: Nested PCR product using primer T758/T363 after the first round PCR amplified with the primer T758/T458. PAM sequence is highlighted in red. The scissors indicate the precise cleavage site at the third nucleotide from the PAM. The predicted deletion between GagD and 3'-LTR1 is displayed along with the additional deletions or the unexpected insertions highlighted in green. The black dot line indicates the deleted portion. The blue and pink solid bar indicate the locations of the cleavage sites. The numbers above the fragments indicated the start and the end of the nucleotide sites. TA clones with stars are selected to show detail sequence. The lower fragment from hThymus tissue of mouse B5M3 indicated with green arrow in FIG. 10B was identified nonspecific by sequencing while the upper band was the cleaved residual sequence. FIG. 21B: Representative Sanger sequence tracing of clone B5M3-hThymus-1 showing the cleaving/relegation site indicated by arrowheads between the GagD and 3'-LTR1. The cleaved sequence of GagD and 3'-LTR1 which were then joined together after deletion. The cleavage sites are highlighted with purple and blue respectively. The primer T758 and T363 sequence is highlighted with red and yellow respectively. FIG. 21A discloses SEQ ID NOS 223-225, respectively, in order of appearance. FIG. 21B discloses SEQ ID NOS 226-236, respectively, in order of appearance.

FIG. 22A: To retain the expression of intact HIV-1 Nef for pathogenesis and early HIV infection, a P2A peptide, a self-cleaving peptide which can cleave between genes upstream and downstream, and a portion of 5'Nef were cloned at the 3' end of each reporter in frame. The cleavage site of 2A peptide is precise and well defined, in such case, only one additional amino acid at the N-terminus of Nef was expected.

FIG. 22B: In EcoHIV-eLuc, the HIV gp120 is replaced with gp80 from ecotropic murine leukemia virus to infect only mouse cells rather than human cells.

DETAILED DESCRIPTION

Figures 1A, 1B:
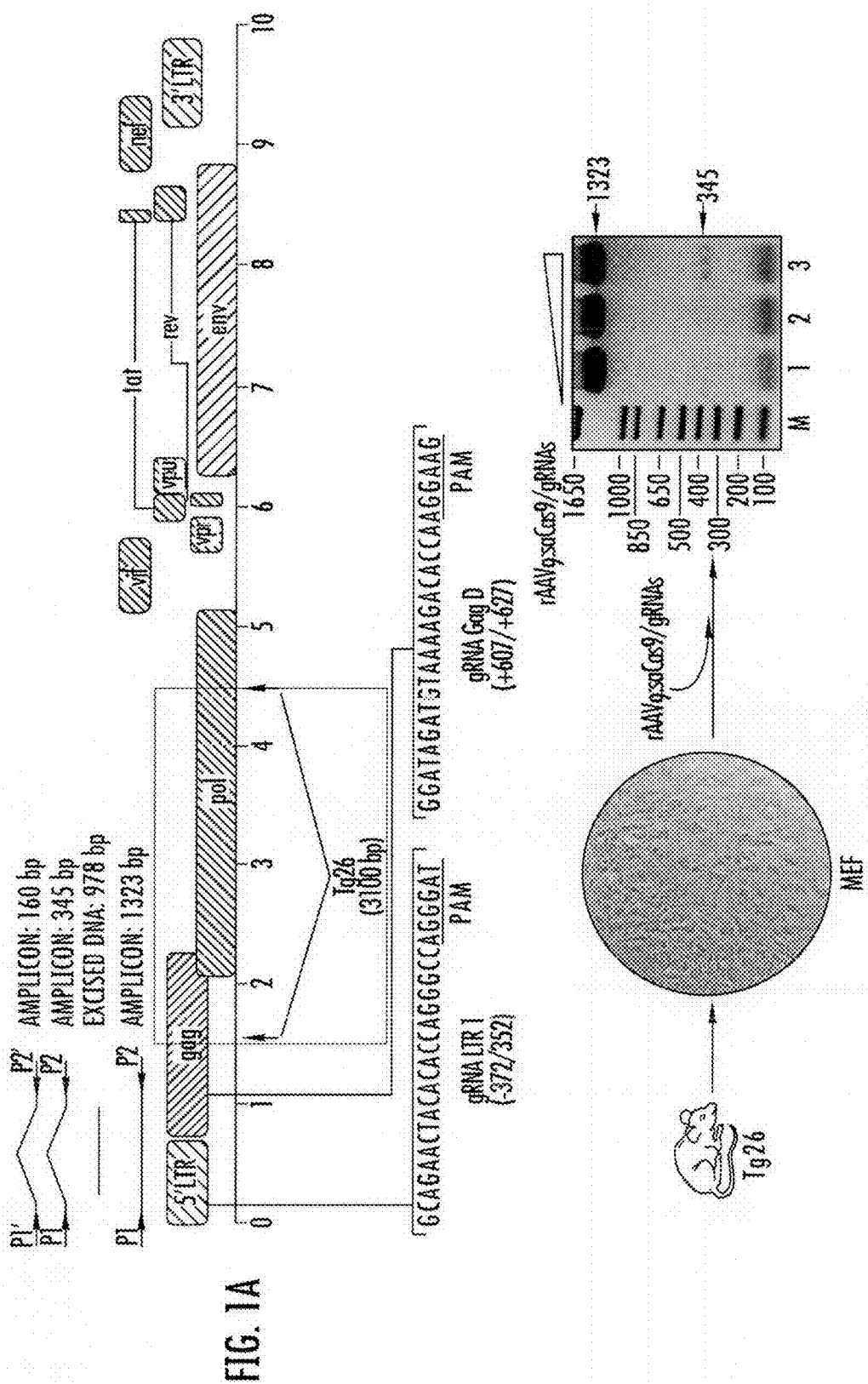
FIGS. 1A and 1B depict the excision of HIV-1 DNA by rAAV9:saCas9/gRNA Tg26 MEF.

Gene editing techniques were developed and based on RNA-guided Cas9 (known as CRISPR/Cas9) to specifically target the HIV-1 genome and eliminate integrated copies of the proviral DNA. Several specific sequences within the U3 region of the HIV-1 long term repeat (LTR) were identified that serve as targets for the creation of specific guide RNAs (gRNAs) to edit their target sequences by single and multiplex Cas9/gRNAs complexes. This strategy can lead to complete elimination of viral replication in latently infected $CD4^+$ T-cells and mononuclear phagocytes (monocyte, macrophages, microglia and dendritic cells) (Hu W, et al. *Proc Natl Acad Sci USA* 2014; 111:11461-11466; Khalili K, et al. *J Neurovirol* 2015; 21:310-321; incorporated herein by reference). The CRISPR/Cas9 had no genotoxic effects or off-target editing of the host genome, yet, for the first time, showed the ability of this technology to precisely excise a 9709 bp DNA fragment of the integrated proviral genome that spans between the 5' and 3' HIV-1 LTRs. The presence of multiplex gRNAs and Cas9 also protects against subsequent HIV-1 infection and was used successfully in cell models of human disease (Ebina H, et al. *Sci Rep* 2013; 3:2510; Liao H K, et al. *Nat Commun* 2015; 6:6413; Zhu W, et al. *Retrovirology* 2015; 12:22).

However, an important challenge relates to the in vivo delivery of functional CRISPR/Cas9 to tissues and cells that harbor viral DNA. In recent years, Adeno-Associated Virus Vectors (AAV) has captured much attention as a gene delivery system for treating human disease caused by a gene loss or mutation (Mittermeyer G, et al. *Hum Gene Ther* 2012; 23:377-381). The advantages of the AAV delivery scheme include its low toxicity and sustained gene expression which can extend to twelve months after a single administration (Boudreau R L, et al. *Hum Mol Genet* 2011; 20:R21-R27; Naldini L. *Nature* 2015; 526:351-360). The most common diseases targeted by AAV delivery systems include cancer, heart failure, neurodegenerative diseases, arthritis, muscular dystrophy, cystic fibrosis and Canavan's disease amongst others (Bennett J, et al. *Sci Transl Med.* 2012; 4:120ra15; Janson C, et al. *Hum Gene Ther* 2002; 13:1391-1412).

The present invention provides, for the first time, compositions and methods that produce the excision of portions of integrated HIV genomes in an in vivo murine model. Specifically, compositions according to the present invention include an AAV-based CAs9/gRNA gene editing delivery system.

Accordingly, embodiments of the invention are directed to compositions for the efficient in vivo intracellular delivery of CRISPR/Cas9 gene editing system developed to eliminate integrated retroviral DNA sequences, e.g. human immunodeficiency virus (HIV), from latently infected human cells and animal disease models. Methods for editing of integrated proviral DNA and eliminating the virus comprise administering a composition of the CRISPR/Cas9 system(s).

All genes, gene names, and gene products disclosed herein are intended to correspond to homologs from any species for which the compositions and methods disclosed herein are applicable. It is understood that when a gene or gene product from a particular species is disclosed, this disclosure is intended to be exemplary only, and is not to be interpreted as a limitation unless the context in which it appears clearly indicates. Thus, the genes or gene products disclosed herein, are intended to encompass homologous and/or orthologous genes and gene products from other species.

The following description of the preferred embodiments is merely exemplary in nature and is in no way intended to limit the invention, its application or uses. Embodiments of the invention may be practiced without the theoretical aspects presented. Moreover, the theoretical aspects are presented with the understanding that Applicants do not seek to be bound by the theory presented.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, natural or synthetic compounds and the like. An agent can be assayed in accordance with the methods of the invention at any stage during clinical trials, during pre-trial testing, or following FDA-approval.

The term "anti-viral agent" as used herein, refers to any molecule that is used for the treatment of a virus and include agents which alleviate any symptoms associated with the virus, for example, anti-pyretic agents, anti-inflammatory agents, chemotherapeutic agents, and the like. An antiviral agent includes, without limitation: antibodies, aptamers, adjuvants, anti-sense oligonucleotides, chemokines, cytokines, immune stimulating agents, immune modulating agents, B-cell modulators, T-cell modulators, NK cell modulators, antigen presenting cell modulators, enzymes, siRNA's, ribavirin, ribozymes, protease inhibitors, helicase inhibitors, polymerase inhibitors, helicase inhibitors, neuraminidase inhibitors, nucleoside reverse transcriptase inhibitors, non-nucleoside reverse transcriptase inhibitors, purine nucleosides, chemokine receptor antagonists, interleukins, or combinations thereof.

"Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, *Nucl. Acid. Res.*, 1997, 25(22), 4429-4443, Toulmé, J. J., *Nature Biotechnology* 19:17-18 (2001); Manoharan M., *Biochemica et Biophysica Acta* 1489:117-139(1999); Freier S. M., Nucleic Acid Research, 25:4429-4443 (1997), Uhlman, E., *Drug Discovery & Development*, 3: 203-213 (2000), Herdewin P., *Antisense & Nucleic Acid Drug Dev.*, 10:297-310 (2000)); 2-O, 3'-C-linked [3.2.0] bicycloarabinonucleosides (see e.g. N. K. Christiensen., et al., *J. Am. Chem. Soc.,* 120: 5458-5463 (1998). Such analogs include synthetic nucleosides designed to enhance binding properties, e.g., duplex or triplex stability, specificity, or the like.

The term "antibody" as used herein comprises one or more virus specific binding domains which bind to and aid in the immune mediated-destruction and clearance of the virus, e.g. HIV virus. The antibody or fragments thereof, comprise IgA, IgM, IgG, IgE, IgD or combinations thereof.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

An "effective amount" as used herein, means an amount which provides a therapeutic or prophylactic benefit. As defined herein, an "effective" amount of a compound or agent (i.e., an effective dosage) means an amount sufficient to produce a (e.g., clinically) desirable result.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. A "nucleotide sequence encoding" an amino acid sequence includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "eradication" of the retrovirus, e.g. HIV virus, as used herein, means that that virus is unable to replicate, the genome is deleted, fragmented, degraded, genetically inactivated, or any other physical, biological, chemical or structural manifestation, that prevents the virus from being transmissible or infecting any other cell or subject resulting in the clearance of the virus in vivo. In some cases, fragments of the viral genome may be detectable, however, the virus is incapable of replication, or infection etc.

The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "immunoregulatory" or "immune cell modulator" is meant a compound, composition or substance that is immunogenic (i.e. stimulates or increases an immune response) or immunosuppressive (i.e. reduces or suppresses an immune response). "Cells of the immune system" or "immune cells", is meant to include any cells of the immune system that may be assayed or involved in mounting an immune response, including, but not limited to, B lymphocytes, also called B cells, T lymphocytes, also called T cells, natural killer (NK) cells, natural killer T (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types. The functions or responses to an antigen can be measured by any type of assay, e.g. RIA, ELISA, FACS, Western blotting, etc.

The term "induces or enhances an immune response" is meant causing a statistically measurable induction or increase in an immune response over a control sample to which the peptide, polypeptide or protein has not been administered. Conversely, "suppression" of an immune response is a measurable decrease in an immune response over a control sample to which the peptide, polypeptide or protein has been administered, for example, as in the case of suppression of an immune response in an auto-immune scenario. Preferably the induction or enhancement of the immune response results in a prophylactic or therapeutic response in a subject. Examples of immune responses are increased production of type I IFN, increased resistance to viral and other types of infection by alternate pathogens. The enhancement of immune responses to viruses (anti-virus responses), or the development of vaccines to prevent virus infections or eliminate existing viruses.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes: a recombinant DNA which is part of a hybrid gene encoding additional polypeptide sequence, complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like.

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

As used herein, a "nucleic acid", "isolated nucleic acid sequence" or "nucleic acid sequence" or "cDNA" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs, and refers to nucleic acid sequences in which one or more introns have been removed. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequences.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C_3$-$C_6$)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

As used herein, the terms "nucleic acid sequence", "polynucleotide," and "gene" are used interchangeably throughout the specification and include complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like.

The nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992).

"Optional" or "optionally" means that the subsequently described event or circumstance can or cannot occur, and that the description includes instances where the event or circumstance occurs and instances where it does not.

"Parenteral" administration of an immunogenic composition includes, e.g., subcutaneous (s.c.), intravenous (i.v.), intramuscular (i.m.), or intrasternal injection, or infusion techniques.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

As used herein, unless otherwise indicated, the terms "peptide", "polypeptide" or "protein" are used interchangeably herein, and refer to a polymer of amino acids of varying sizes. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or be naturally occurring. This term also includes polypeptides that have been modified or derivatized, such as by glycosylation, acetylation, phosphorylation, and the like.

The term "polynucleotide" is a chain of nucleotides, also known as a "nucleic acid". As used herein polynucleotides include, but are not limited to, all nucleic acid sequences which are obtained by any means available in the art, and include both naturally occurring and synthetic nucleic acids.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

The term "target nucleic acid" refers to a nucleic acid sequence from a retrovirus, to which the oligonucleotide or guide nucleic acid sequence e.g. gRNA, is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding oligonucleotide directed to the target. The term target nucleic acid may refer to the specific subsequence of a larger nucleic acid to which the oligonucleotide is directed or to the overall sequence (e.g., gene or mRNA).

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof, or (3) relieving the disease, i.e., causing regression of the state, disorder or condition or at least one of its clinical or subclinical symptoms. The benefit to an individual to be treated is either statistically significant or at least perceptible to the patient or to the physician.

As defined herein, a "therapeutically effective" amount of a compound or agent (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

As used herein, the term "kit" refers to any delivery system for delivering materials. Inclusive of the term "kits" are kits for both research and clinical applications. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides or liposomes. The term "fragmented kit" is intended to encompass kits containing Analyte specific reagents (ASR's) regulated under section 520 (e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "percent sequence identity" or having "a sequence identity" refers to the degree of identity between any given query sequence and a subject sequence.

The terms "pharmaceutically acceptable" (or "pharmacologically acceptable") refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Where any amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

General Techniques

For further elaboration of general techniques useful in the practice of this invention, the practitioner can refer to standard textbooks and reviews in cell biology, tissue culture, embryology, and physiology.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Compositions

Embodiments of the invention are directed to compositions for the excision and/or eradication of retroviral nucleic acid sequences from infected cells in vitro or in vivo. Methods of treatment or prevention of an infection comprise the use of the compositions embodied herein.

Briefly, Cas9 endonucleases with guide RNAs (gRNAs) recognizing the viral long terminal repeat (LTR) and the group-specific antigen (Gag) were delivered through a recombinant adeno associated virus 9 (rAAV9) vector to Tg26 transgenic mice. The murine cells harbored multiple copies of HIV-1 integrated into chromosome 8. rAAV9 expressing saCas9/gRNAs treatment of Tg26 embryonic murine fibroblasts verified the ability and efficacy of editing integrated copies of HIV-1 DNA. rAAV9:saCas9/gRNA resulted in the cleavage of the integrated HIV-1 DNA. Excision of a 940 bp DNA fragment spanning between the HIV-1 LTR and Gag gene in spleen, liver, heart, lung, kidney, brain and circulating lymphocytes was detected. These results demonstrated the capacity of rAAV9 to effectively deliver functionally active CRISPR/saCas9 to virus containing tissues.

Accordingly, the invention features compositions comprising a nucleic acid encoding a CRISPR-associated endonuclease and a guide RNA that is complementary to a target sequence in a retrovirus, e.g., HIV, as well as pharmaceutical formulations comprising a nucleic acid encoding a CRISPR-associated endonuclease and a guide RNA that is complementary to a target sequence in HIV. Also featured are compositions comprising a CRISPR-associated endonuclease polypeptide and a guide RNA that is complementary to a target sequence in HIV, as well as pharmaceutical formulations comprising a CRISPR-associated endonuclease polypeptide and a guide RNA that is complementary to a target sequence in HIV.

Also featured are methods of administering the compositions to treat a retroviral infection, e.g., HIV infection, methods of eliminating viral replication, and methods of preventing HIV infection. The therapeutic methods described herein can be carried out in connection with other antiretroviral therapies (e.g., HAART).

Methods of the invention may be used to remove viral or other foreign genetic material from a host organism, without interfering with the integrity of the host's genetic material. A nuclease may be used to target viral nucleic acid, thereby interfering with viral replication or transcription or even excising the viral genetic material from the host genome. The nuclease may be specifically targeted to remove only the viral nucleic acid without acting on host material either when the viral nucleic acid exists as a particle within the cell or when it is integrated into the host genome. Targeting the viral nucleic acid can be done using a sequence-specific moiety such as a guide RNA that targets viral genomic material for destruction by the nuclease and does not target the host cell genome. In some embodiments, a CRISPR/Cas nuclease and guide RNA (gRNA) that together target and selectively edit or destroy viral genomic material is used. The CRISPR (clustered regularly interspaced short palindromic repeats) is a naturally-occurring element of the bacterial immune system that protects bacteria from phage infection. The guide RNA localizes the CRISPR/Cas complex to a viral target sequence. Binding of the complex localizes the Cas endonuclease to the viral genomic target sequence causing breaks in the viral genome. Other nuclease systems can be used including, for example, zinc finger nucleases, transcription activator-like effector nucleases (TALENs), meganucleases, or any other system that can be used to degrade or interfere with viral nucleic acid without interfering with the regular function of the host's genetic material.

The compositions may be used to target viral nucleic acid in any form or at any stage in the viral life cycle. The targeted viral nucleic acid may be present in the host cell as independent particles. In a preferred embodiment, the viral infection is latent and the viral nucleic acid is integrated into the host genome. Any suitable viral nucleic acid may be targeted for cleavage and digestion.

In embodiments, the compositions of the invention include nucleic acids encoding gene editing agents and at least one guide RNA (gRNA) that is complementary to a target sequence in a retrovirus. In embodiments, the gene editing agents comprise: Cre recombinases, CRISPR/Cas molecules, TALE transcriptional activators, Cas9 nucleases, nickases, transcriptional regulators, homologues, orthologs or combinations thereof.

In one embodiment, a composition comprises a viral vector encoding a gene editing agent and at least one guide RNA (gRNA) wherein the gRNA is complementary to a target nucleic acid sequence of a retrovirus gene sequence, comprising: a target nucleic acid sequence of a coding and/or non-coding retrovirus gene sequence, a target nucleic acid sequence of a retrovirus group specific antigen or combinations thereof. The gRNA is complementary to a long terminal repeat (LTR), a group-specific antigen or combinations thereof of the retrovirus. In this embodiment, the gene editing agent is a Clustered Regularly Interspaced Short Palindromic Repeated (CRISPR)-associated endonuclease, or homologues thereof. An example of a CRISPR-associated endonuclease is Cas9 or homologues or orthologs thereof.

In another embodiment, an expression vector comprises an isolated nucleic acid encoding a gene editing agent and at least one guide RNA (gRNA) wherein the gRNA is complementary to a target nucleic acid sequence of a retrovirus gene sequence, a target nucleic acid sequence of a group specific antigen or combinations thereof. In embodiments, the gene editing agents comprise: Cre recombinases, CRISPR/Cas molecules, TALE transcriptional activators, Cas9 nucleases, nickases, transcriptional regulators, homologues, orthologs or combinations thereof. In one embodiment, the gene editing agent is a Clustered Regularly Interspaced Short Palindromic Repeated (CRISPR)-associated endonuclease, or homologues or orthologs thereof. In another embodiment, the CRISPR-associated endonuclease is Cas9 or homologues or orthologs, thereof. In one embodiment, the gRNA is complementary to a long terminal repeat (LTR), a group-specific antigen or combinations thereof of the retrovirus gene sequence.

In some embodiments, the retrovirus is a lentivirus wherein the lentivirus comprises: a human immunodeficiency virus; a simian immunodeficiency virus; a feline immunodeficiency virus; a bovine immunodeficiency virus or Human T-cell leukemia virus. Accordingly, in one embodiment, a target sequence comprises a sequence within the long terminal repeat (LTR) of the human immunodeficiency virus. An example of a sequence within the long terminal repeat of the human immunodeficiency virus comprises a sequence within the U3, R, or U5 regions.

In embodiments, a viral vector comprises an adenovirus vector, an adeno-associated viral vector (AAV), or derivatives thereof. The viral vector is in some embodiments an adeno-associated viral vector comprising AAV serotypes 1, 2, 3, 4, 5, 6, 7, 8, 9, 10, 11, DJ or DJ/8. In one embodiment, the AAV vector is AAV serotype 9. ($AAV_9$).

In some embodiments, the expression vector encodes a transactivating small RNA (tracrRNA) wherein the transactivating small RNA (tracrRNA) sequence is fused to the sequence encoding the guide RNA.

In another embodiment, the expression vector further comprises a sequence encoding a nuclear localization signal.

Gene Editing Agents: Compositions of the invention include at least one gene editing agent, comprising CRISPR-associated nucleases such as Cas9 and Cpf1 gRNAs, Argonaute family of endonucleases, clustered regularly interspaced short palindromic repeat (CRISPR) nucleases, zinc-finger nucleases (ZFNs), transcription activator-like effector nucleases (TALENs), meganucleases, other endo- or exonucleases, or combinations thereof. See Schiffer, 2012, *J Virol* 88(17):8920-8936, incorporated by reference.

The composition can also include C2c2—the first naturally-occurring CRISPR system that targets only RNA. The Class 2 type VI-A CRISPR-Cas effector "C2c2" demonstrates an RNA-guided RNase function. C2c2 from the bacterium *Leptotrichia shahii* provides interference against RNA phage. In vitro biochemical analysis show that C2c2 is guided by a single crRNA and can be programmed to cleave ssRNA targets carrying complementary protospacers. In bacteria, C2c2 can be programmed to knock down specific mRNAs. Cleavage is mediated by catalytic residues in the two conserved HEPN domains, mutations in which generate catalytically inactive RNA-binding proteins. These results demonstrate the capability of C2c2 as a new RNA-targeting tools.

C2c2 can be programmed to cleave particular RNA sequences in bacterial cells. The RNA-focused action of C2c2 complements the CRISPR-Cas9 system, which targets DNA, the genomic blueprint for cellular identity and function. The ability to target only RNA, which helps carry out the genomic instructions, offers the ability to specifically manipulate RNA in a high-throughput manner- and manipulate gene function more broadly.

CRISPR/Cpf1 is a DNA-editing technology analogous to the CRISPR/Cas9 system, characterized in 2015 by Feng Zhang's group from the Broad Institute and MIT. Cpf1 is an RNA-guided endonuclease of a class II CRISPR/Cas system. This acquired immune mechanism is found in *Prevotella* and *Francisella* bacteria. It prevents genetic damage from viruses. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. CRISPR/Cpf1 could have multiple applications, including treatment of genetic illnesses and degenerative conditions. As referenced above, Argonaute is another potential gene editing system.

CRISPR-Associated Endonucleases: In an embodiment, a composition comprises a CRISPR-associated endonuclease, e.g., Cas9, or homologues thereof and a guide RNA that is complementary to a target sequence in a retrovirus, e.g., HIV.

CRISPR (Clustered Regularly Interspaced Short Palindromic Repeats) is found in bacteria and is believed to protect the bacteria from phage infection. It has recently been used as a means to alter gene expression in eukaryotic DNA, but has not been proposed as an anti-viral therapy or more broadly as a way to disrupt genomic material. Rather, it has been used to introduce insertions or deletions as a way of increasing or decreasing transcription in the DNA of a targeted cell or population of cells. See for example, Horvath et al., *Science* (2010) 327:167-170; Terns et al., *Current Opinion in Microbiology* (2011) 14:321-327; Bhaya et al., *Annu Rev Genet* (2011) 45:273-297; Wiedenheft et al., *Nature* (2012) 482:331-338); Jinek M et al., *Science* (2012) 337:816-821; Cong L et al., *Science* (2013) 339:819-823; Jinek M et al., (2013) *eLife* 2:e00471; Mali P et al. (2013) *Science* 339:823-826; Qi L S et al. (2013) *Cell* 152:1173-1183; Gilbert L A et al. (2013) *Cell* 154:442-451; Yang H et al. (2013) *Cell* 154:1370-1379; and Wang H et al. (2013) *Cell* 153:910-918).

CRISPR methodologies employ a nuclease, CRISPR-associated (Cas), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas and guide RNA (gRNA) may be synthesized by known methods. Cas/guide-RNA (gRNA) uses a non-specific DNA cleavage protein Cas, and an RNA oligonucleotide to hybridize to target and recruit the Cas/gRNA complex. See Chang et al., 2013, *Cell Res.* 23:465-472; Hwang et al., 2013, *Nat. Biotechnol.* 31:227-229; Xiao et al., 2013, *Nucl. Acids Res.* 1-11.

In general, the CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNase domains, protein-protein interaction domains, dimerization domains, as well as other domains. The mechanism through which CRISPR/Cas9-induced mutations inactivate the provirus can vary. For example, the mutation can affect proviral replication, and viral gene expression. The mutation can comprise one or more deletions. The size of the deletion can vary from a single nucleotide base pair to about 10,000 base pairs. In some embodiments, the deletion can include all or substantially all of the proviral sequence. In some embodiments the deletion can eradicate the provirus. The mutation can also comprise one or more insertions, that is, the addition of one or more nucleotide base pairs to the proviral sequence. The size of the inserted sequence also may vary, for example from about one base pair to about 300 nucleotide base pairs. The mutation can comprise one or more point mutations, that is, the replacement of a single nucleotide with another nucleotide. Useful point mutations are those that have functional consequences, for example, mutations that result in the conversion of an amino acid codon into a termination codon, or that result in the production of a nonfunctional protein.

In embodiments. the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

In some embodiments, the CRISPR/Cas-like protein can be derived from a wild type Cas9 protein or fragment thereof. In other embodiments, the CRISPR/Cas-like protein can be derived from modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

Three types (I-III) of CRISPR systems have been identified. CRISPR clusters contain spacers, the sequences complementary to antecedent mobile elements. CRISPR clusters are transcribed and processed into mature CRISPR RNA (crRNA). In embodiments, the CRISPR/Cas system can be a type I, a type II, or a type III system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

In one embodiment, the RNA-guided endonuclease is derived from a type II CRISPR/Cas system. The CRISPR-associated endonuclease, Cas9, belongs to the type II CRISPR/Cas system and has strong endonuclease activity to cut target DNA. Cas9 is guided by a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM). The crRNA and tracrRNA can be expressed separately or engineered into an artificial fusion small guide RNA (sgRNA) via a synthetic stem loop (AGAAAU) to mimic the natural crRNA/tracrRNA duplex. Such sgRNA, like shRNA, can be synthesized or in vitro transcribed for direct RNA transfection or expressed from U6 or H1-promoted RNA expression vector, although cleavage efficiencies of the artificial sgRNA are lower than those for systems with the crRNA and tracrRNA expressed separately.

The CRISPR-associated endonuclease Cas9 nuclease can have a nucleotide sequence identical to the wild type *Streptococcus pyogenes* sequence. The CRISPR-associated endonuclease may be a sequence from other species, for example other *Streptococcus* species, such as thermophiles. The Cas9 nuclease sequence can be derived from other species including, but not limited to: *Nocardiopsis dassonvillei, Streptomyces pristinaespiralis, Streptomyces viridochromogenes, Streptomyces roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina,* Burkholderiales bacterium, *Polaromonas naphthalenivorans, Polaromonas* sp., Crocosphaera *watsonii,* Cyanothece sp., *Microcystis aeruginosa, Synechococcus* sp., *Acetohalobium arabaticum,* Ammonfex *degensii,* Caldicelulosiruptor becscii, *Candidatus* desulforudis, *Clostridium botulinum, Clostridium difficle, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or Acaryochloris *marina. Pseudomonas aeruginosa, Escherichia coli,* or other sequenced bacteria genomes and archaea, or other prokaryotic microorganisms may also be a source of the Cas9 sequence utilized in the embodiments disclosed herein.

The wild type *Streptococcus pyogenes* Cas9 sequence can be modified. The nucleic acid sequence can be codon optimized for efficient expression in mammalian cells, i.e., "humanized." sequence can be for example, the Cas9 nuclease sequence encoded by any of the expression vectors listed in Genbank accession numbers KM099231.1 GI:669193757; KM099232.1 GI:669193761; or KM099233.1 GI:669193765. Alternatively, the Cas9 nuclease sequence can be for example, the sequence contained within a commercially available vector such as PX330 or PX260 from Addgene (Cambridge, MA). In some embodiments, the Cas9 endonuclease can have an amino acid sequence that is a variant or a fragment of any of the Cas9 endonuclease sequences of Genbank accession numbers KM099231.1 GI:669193757; KM099232.1 GI:669193761; or KM099233.1 GI:669193765 or Cas9 amino acid sequence of PX330 or PX260 (Addgene, Cambridge, MA). The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9 polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cas9 polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the Cas9 amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and L-cyclopentyl glycine (S)-2-amino-2-cyclopentyl acetic acid. For other examples, one can consult textbooks or the worldwide web (a site currently maintained by the California Institute of Technology displays structures of non-natural amino acids that have been successfully incorporated into functional proteins).

The Cas9 nuclease sequence can be a mutated sequence. For example, the Cas9 nuclease can be mutated in the conserved HNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks.

The Cas9 can be an orthologous. Six smaller Cas9 orthologues have been used and reports have shown that Cas9 from *Staphylococcus aureus* (SaCas9) can edit the genome with efficiencies similar to those of SpCas9, while being more than 1 kilobase shorter.

In addition to the wild type and variant Cas9 endonucleases described, embodiments of the invention also encompass CRISPR systems including newly developed "enhanced-specificity" *S. pyogenes* Cas9 variants (eSpCas9), which dramatically reduce off target cleavage. These variants are engineered with alanine substitutions to neutralize positively charged sites in a groove that interacts with the non-target strand of DNA. This aim of this modification is to reduce interaction of Cas9 with the non-target strand, thereby encouraging re-hybridization between target and non-target strands. The effect of this modification is a requirement for more stringent Watson-Crick pairing between the gRNA and the target DNA strand, which limits off-target cleavage (Slaymaker, I. M. et al. (2015) DOI: 10.1126/science.aad5227).

In certain embodiments, three variants found to have the best cleavage efficiency and fewest off-target effects: SpCas9(K855A), SpCas9(K810A/K1003A/R1060A) (a.k.a. eSpCas9 1.0), and SpCas9(K848A/K1003A/R1060A) (a.k.a. eSPCas9 1.1) are employed in the compositions. The invention is by no means limited to these variants, and also encompasses all Cas9 variants (Slaymaker, I. M. et al. (2015)).

The present invention also includes another type of enhanced specificity Cas9 variant, "high fidelity" spCas9 variants (HF-Cas9) (Kleinstiver, B. P. et al., 2016, Nature. DOI: 10.1038/nature16526).

As used herein, the term "Cas" is meant to include all Cas molecules comprising variants, mutants, orthologues, high-fidelity variants and the like.

Guide Nucleic Acid Sequences: Guide RNA sequences according to the present invention can be sense or anti-sense sequences. The specific sequence of the gRNA may vary, but, regardless of the sequence, useful guide RNA sequences will be those that minimize off-target effects while achieving high efficiency and complete ablation of the virus. The guide RNA sequence generally includes a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. Other Cas9 orthologues may have different PAM specificities. For example, Cas9 from *S. thermophilus* requires 5'-NNAGAA for CRISPR1 and 5'-NGGNG for CRISPR3 and *Neisseria meningitidis* requires 5'-NNNN-GATT. The specific sequence of the guide RNA may vary, but, regardless of the sequence, useful guide RNA sequences will be those that minimize off-target effects while achieving high efficiency and complete ablation of the retrovirus, for example, the HIV virus. The length of the guide RNA sequence can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides.

The guide RNA sequence can be configured as a single sequence or as a combination of one or more different sequences, e.g., a multiplex configuration. Multiplex configurations can include combinations of two, three, four, five, six, seven, eight, nine, ten, or more different guide RNAs. In certain embodiments, the composition comprises multiple different gRNA molecules, each targeted to a different target sequence. In certain embodiments, this multiplexed strategy provides for increased efficacy. These multiplex gRNAs can be expressed separately in different vectors or expressed in one single vector.

The compositions of the invention include sequence encoding a guide RNA (gRNA) comprising a sequence that is complementary to a target sequence in a retrovirus. The retrovirus can be a lentivirus, for example, a human immunodeficiency virus; a simian immunodeficiency virus; a feline immunodeficiency virus; a bovine immunodeficiency virus or Human T-cell leukemia virus. The human immunodeficiency virus can be HIV-1 or HIV-2. The target sequence can include a sequence from any HIV, for example, HIV-1 and HIV-2, and any circulating recombinant form thereof. The genetic variability of HIV is reflected in the multiple groups and subtypes that have been described. A collection of HIV sequences is compiled in the Los Alamos HIV databases and compendiums. The methods and compositions of the invention can be applied to HIV from any of those various groups, subtypes, and circulating recombinant forms. These include for example, the HIV-1 major group (often referred to as Group M) and the minor groups, Groups N, O, and P, as well as but not limited to, any of the following subtypes, A, B, C, D, F, G, H, J and K. or group (for example, but not limited to any of the following Groups, N, O and P) of HIV. The methods and compositions can also be applied to HIV-2 and any of the A, B, C, F or G clades (also referred to as "subtypes" or "groups"), as well as any circulating recombinant form of HIV-2.

The guide RNA can be a sequence complimentary to a coding or a non-coding sequence. For example, the guide RNA can be complementary to an HIV sequence, such as a long terminal repeat (LTR) sequence, a protein coding sequence, or a regulatory sequence. In some embodiments, the guide RNA comprises a sequence that is complementary to an HIV long terminal repeat (LTR) region. The HIV-1 LTR is approximately 640 bp in length. HIV-1 long terminal repeats (LTRs) are divided into U3, R and U5 regions. LTRs contain all of the required signals for gene expression and are involved in the integration of a provirus into the genome of a host cell. For example, the basal or core promoter, a core enhancer and a modulatory region is found within U3 while the transactivation response element is found within R. In HIV-1, the U5 region includes several sub-regions, for example, TAR or trans-acting responsive element, which is involved in transcriptional activation; Poly A, which is involved in dimerization and genome packaging; PBS or primer binding site; Psi or the packaging signal; DIS or dimer initiation site.

Useful guide sequences are complementary to the U3, R, or U5 region of the LTR. A guide RNA sequence can comprise, for example, a sequence complementary to the target protospacer sequence of: sequence or consensus sequence. The invention is not so limiting however, and the guide RNA sequences can be selected to target any variant or mutant HIV sequence. In some embodiments, more than one guide RNA sequence is employed, for example a first guide RNA sequence and a second guide RNA sequence, with the first and second guide RNA sequences being complimentary to target sequences in any of the above mentioned retroviral regions. In some embodiments, the guide RNA can include a variant sequence or quasi-species sequence. In some embodiments, the guide RNA can be a sequence corresponding to a sequence in the genome of the virus harbored by the subject undergoing treatment. Thus for example, the sequence of the particular U3, R, or U5 region in the HIV virus harbored by the subject can be obtained and guide RNAs complementary to the patient's particular sequences can be used.

In some embodiments, the guide RNA can be a sequence complimentary to a protein coding sequence, for example, a sequence encoding one or more viral structural proteins, (e.g., gag, pol, env and tat). Thus, the sequence can be complementary to sequence within the gag polyprotein, e.g., MA (matrix protein, p17); CA (capsid protein, p24); SP1 (spacer peptide 1, p2); NC (nucleocapsid protein, p7); SP2 (spacer peptide 2, p1) and P6 protein; pol, e.g., reverse transcriptase (RT) and RNase H, integrase (IN), and HIV protease (PR); env, e.g., gp160, or a cleavage product of gp160, e.g., gp120 or SU, and gp41 or TM; or tat, e.g., the 72-amino acid one-exon Tat or the 86-101 amino-acid two-exon Tat. In some embodiments, the guide RNA can be a sequence complementary to a sequence encoding an accessory protein, including, for example, vif, nef (negative factor) vpu (Virus protein U) and tev.

In some embodiments, the sequence can be a sequence complementary to a structural or regulatory element, for example, an LTR, as described above; TAR (Target sequence for viral transactivation), the binding site for Tat protein and for cellular proteins, consists of approximately the first 45 nucleotides of the viral mRNAs in HIV-1 (or the first 100 nucleotides in HIV-2) forms a hairpin stem-loop structure; RRE (Rev responsive element) an RNA element encoded within the env region of HIV-1, consisting of approximately 200 nucleotides (positions 7710 to 8061 from the start of transcription in HIV-1, spanning the border of gp120 and gp41); PE (Psi element), a set of 4 stem-loop structures preceding and overlapping the Gag start codon; SLIP, a TTTTTT "slippery site", followed by a stem-loop structure; CRS (Cis-acting repressive sequences); INS Inhibitory/Instability RNA sequences) found for example, at nucleotides 414 to 631 in the gag region of HIV-1.

The guide RNA sequence can be a sense or anti-sense sequence. The guide RNA sequence generally includes a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. Other Cas9 orthologs may have different PAM specificities. For example, Cas9 from *S. thermophilus* requires 5'-NNAGAA for CRISPR1 and 5'-NGGNG for CRISPR3) and *Neisseria meningitidis* requires 5'-NNNNGATT). The specific sequence of the guide RNA may vary, but, regardless of the sequence, useful guide RNA sequences will be those that minimize off-target effects while achieving high efficiency and complete ablation of the genomically integrated HIV-1 provirus. The length of the guide RNA sequence can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides. Useful selection methods identify regions having extremely low homology between the foreign viral genome and host cellular genome including endogenous retroviral DNA, include bioinformatic screening using 12-bp+NGG target-selection criteria to exclude off-target human transcriptome or (even rarely) untranslated-genomic sites; avoiding transcription factor binding sites within the HIV-1 LTR promoter (potentially conserved in the host genome); selection of LTR-A- and -B-directed, 30-bp gRNAs and also pre-crRNA system reflecting the original bacterial immune mechanism to enhance specificity/efficiency vs. 20-bp gRNA-, chimeric crRNA-tracRNA-based system and WGS, Sanger sequencing and SURVEYOR assay, to identify and exclude potential off-target effects.

The guide RNA sequence can be configured as a single sequence or as a combination of one or more different sequences, e.g., a multiplex configuration. Multiplex configurations can include combinations of two, three, four, five, six, seven, eight, nine, ten, or more different guide RNAs, for example any combination of sequences in U3, R, or U5. In some embodiments, combinations of LTR A, LTR B, LTR C and LTR D can be used. When the compositions are administered in an expression vector, the guide RNAs can be encoded by a single vector. Alternatively, multiple vectors can be engineered to each include two or more different guide RNAs. Useful configurations will result in the excision of viral sequences between cleavage sites resulting in the ablation of HIV genome or HIV protein expression. Thus, the use of two or more different guide RNAs promotes excision of the viral sequences between the cleavage sites recognized by the CRISPR endonuclease. The excised region can vary in size from a single nucleotide to several thousand nucleotides. Exemplary excised regions are described in the examples.

In some embodiments, a gRNA comprises a sequence having at least a 60% sequence identity to any one of SEQ ID NOS: 1 to 76. In some embodiments, a gRNA comprises any one of SEQ ID NOS: 1 to 76.

When the compositions are administered as a nucleic acid or are contained within an expression vector, the CRISPR endonuclease can be encoded by the same nucleic acid or vector as the guide RNA sequences. Alternatively, or in addition, the CRISPR endonuclease can be encoded in a physically separate nucleic acid from the guide RNA sequences or in a separate vector.

In some embodiments, the RNA molecules e.g. crRNA, tracrRNA, gRNA are engineered to comprise one or more modified nucleobases. For example, known modifications of RNA molecules can be found, for example, in Genes VI, Chapter 9 ("Interpreting the Genetic Code"), Lewis, ed. (1997, Oxford University Press, New York), and Modification and Editing of RNA, Grosjean and Benne, eds. (1998, ASM Press, Washington D.C.). Modified RNA components include the following: 2'-O-methylcytidine; $N^4$-methylcytidine; $N^4$-2'-O-dimethylcytidine; $N^4$-acetylcytidine; 5-methylcytidine; 5,2'-O-di methylcytidine; 5-hydroxymethylcytidine; 5-formylcytidine; 2'-O-methyl-5-formylcytidine; 3-methylcytidine; 2-thiocytidine; lysidine; 2'-O-methyluridine; 2-thiouridine; 2-thio-2'-O-methyluridine; 3,2'-O-dimethyluridine; 3-(3-amino-3-carboxypropyl)uridine; 4-thiouridine; ribosylthymine; 5,2'-O-dimethyluridine; 5-methyl-2-thiouridine; 5-hydroxyuridine; 5-methoxyuridine; uridine 5-oxyacetic acid; uridine 5-oxyacetic acid methyl ester; 5-carboxymethyluridine; 5-methoxycarbonylmethyluridine; 5-methoxycarbonylmethyl-2'-O-methyluridine; 5-methoxycarbonylmethyl-2'-thiouridine; 5-carbamoylmethyluridine; 5-carbamoylmethyl-2'-O-methyluridine; 5-(carboxyhydroxymethyl)uridine; 5-(carboxyhydroxymethyl) uridinemethyl ester; 5-aminomethyl-2-thiouridine; 5-methylaminomethyluridine; 5-methylaminomethyl-2-thiouridine; 5-methylaminomethyl-2-selenouridine; 5-carboxymethylaminomethyluridine; 5-carboxymethylaminomethyl-2'-O-methyl-uridine; 5-carboxymethylaminomethyl-2-thiouridine; dihydrouridine; dihydroribosylthymine; 2'-methyladenosine; 2-methyladenosine; $N^6N$-methyladenosine; $N^6,N^6$-dimethyladenosine; $N^6,2'$-O-trimethyladenosine; 2-methylthio-$N^6N$-isopentenyladenosine; $N^6$-(cis-hydroxyisopentenyl)-adenosine; 2-methylthio-$N^6$-(cis-hydroxyisopentenyl)-adenosine; $N^6$-glycinylcarbamoyl) adenosine; $N^6$-threonylcarbamoyl adenosine; $N^6$-methyl-$N^6$-threonylcarbamoyl adenosine; 2-methylthio-$N^6$-methyl-$N^6$-threonylcarbamoyl adenosine; $N^6$-hydroxynorvalylcarbamoyl adenosine; 2-methylthio-$N^6$-hydroxnorvalylcarbamoyl adenosine; 2'-O-ribosyladenosine (phosphate); inosine; 2'O-methyl inosine; 1-methyl inosine; 1;2'-O-dimethyl inosine; 2'-O-methyl guanosine; 1-methyl guanosine; $N^2$-methyl guanosine; $N^2,N^2$-dimethyl guanosine; $N^2,2'$-O-dimethyl guanosine; $N^2,N^2,2'$-0-trimethyl guanosine; 2'-O-ribosyl guanosine (phosphate); 7-methyl guanosine; $N^2;7$-dimethyl guanosine; $N^2$; $N^2;7$-trimethyl guanosine; wyosine; methylwyosine; under-modified hydroxywybutosine; wybutosine; hydroxywybutosine; peroxywybutosine; queuosine; epoxyqueuosine; galactosylqueuosine; mannosyl-queuosine; 7-cyano-7-deazaguanosine; archaeosine [also called 7-formamido-7-deazaguanosine]; and 7-aminomethyl-7-deazaguanosine.

Modified or Mutated Nucleic Acid Sequences: In some embodiments, any of the nucleic acid sequences may be modified or derived from a native nucleic acid sequence, for example, by introduction of mutations, deletions, substitutions, modification of nucleobases, backbones and the like. The nucleic acid sequences include the vectors, gene-editing agents, gRNAs, tracrRNA etc. Examples of some modified nucleic acid sequences envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N ($CH_3$)—N ($CH_3$)—$CH_2$ and O—N($CH_3$)—$CH_2$—$CH_2$ backbones, wherein the native phosphodiester backbone is represented as O—P—O—$CH_2$). The amide backbones disclosed by De Mesmaeker et al. *Acc. Chem. Res.* 1995, 28:366-374) are also embodied herein. In some embodiments, the nucleic acid sequences having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). The nucleic acid sequences may also comprise one or more substituted sugar moieties. The nucleic acid sequences may also have sugar mimetics such as cyclobutyls in place of the pentofuranosyl group.

The nucleic acid sequences may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentiobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, $N^6$ (6-aminohexyl)adenine and 2,6-diaminopurine. Kornberg, A., DNA Replication, W. H. Freeman & Co., San Francisco, 1980, pp 75-77; Gebeyehu, G., et al. *Nucl. Acids Res.* 1987, 15:4513). A "universal" base known in the art, e.g., inosine may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278).

Another modification of the nucleic acid sequences of the invention involves chemically linking to the nucleic acid sequences one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. EMBO J. 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651).

It is not necessary for all positions in a given nucleic acid sequence to be uniformly modified, and in fact more than one of the aforementioned modifications may be incorporated in a single nucleic acid sequence or even at within a single nucleoside within a nucleic acid sequence.

Modified Proteins or Peptides: Hybrid proteins comprising a polypeptide or fragment thereof may be linked to other types of polypeptides. These additional polypeptides may be any amino acid sequence useful for the purification, identification, overall charge of the protein or peptide, and/or therapeutic or prophylactic application of the peptide. In addition, the additional polypeptide can be a signal peptide, or targeting peptide, etc.

In some embodiments, compositions of the invention can include a CRISPR-associated endonuclease polypeptide encoded by any of the nucleic acid sequences described above. The terms "peptide," "polypeptide," and "protein" are used interchangeably herein, although typically they refer to peptide sequences of varying sizes. It may be referred herein, to the amino acid-based compositions of the invention as "polypeptides" to convey that they are linear polymers of amino acid residues, and to help distinguish them from full-length proteins. A polypeptide of the invention can "constitute" or "include" a fragment of a CRISPR-associated endonuclease, and the invention encompasses polypeptides that constitute or include biologically active variants of a CRISPR-associated endonuclease. It will be understood that the polypeptides can therefore include only a fragment of a CRISPR-associated endonuclease (or a biologically active variant thereof) but may include additional residues as well. Biologically active variants will retain sufficient activity to cleave target DNA.

In some cases, the CRISPR-associated endonuclease polypeptide can include additions, substitutions or deletions may increase the stability (including but not limited to, resistance to proteolytic degradation) of the polypeptide or increase affinity of the polypeptide for its binding proteins. In some cases, the additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which do not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The bonds between the amino acid residues can be conventional peptide bonds or another covalent bond (such as an ester or ether bond), and the polypeptides can be modified by amidation, phosphorylation or glycosylation. A modification can affect the polypeptide backbone and/or one or more side chains. Chemical modifications can be naturally occurring modifications made in vivo following translation of an mRNA encoding the polypeptide (e.g., glycosylation in a bacterial host) or synthetic modifications made in vitro. A biologically active variant of a CRISPR-associated endonuclease can include one or more structural modifications resulting from any combination of naturally occurring (i.e., made naturally in vivo) and synthetic modifications (i.e., naturally occurring or non-naturally occurring modifications made in vitro). Examples of modifications include, but are not limited to, amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

As discussed above, one or more of the amino acid residues in a biologically active variant may be a non-naturally occurring amino acid residue. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins).

Alternatively, or in addition, one or more of the amino acid residues in a biologically active variant can be a naturally occurring residue that differs from the naturally occurring residue found in the corresponding position in a wildtype sequence. In other words, biologically active variants can include one or more amino acid substitutions. We may refer to a substitution, addition, or deletion of amino acid residues as a mutation of the wildtype sequence. As noted, the substitution can replace a naturally occurring amino acid residue with a non-naturally occurring residue or just a different naturally occurring residue. Further the substitution can constitute a conservative or non-conservative substitution. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The polypeptides that are biologically active variants of a CRISPR-associated endonuclease can be characterized in terms of the extent to which their sequence is similar to or identical to the corresponding wild-type polypeptide. For example, the sequence of a biologically active variant can be at least or about 80% identical to corresponding residues in the wild-type polypeptide. For example, a biologically active variant of a CRISPR-associated endonuclease can have an amino acid sequence with at least or about 80% sequence identity (e.g., at least or about 85%, 90%, 95%, 97%, 98%, or 99% sequence identity) to a CRISPR-associated endonuclease or to a homolog or ortholog thereof.

A biologically active variant of a CRISPR-associated endonuclease polypeptide will retain sufficient biological activity to be useful in the present methods. The biologically active variants will retain sufficient activity to function in targeted DNA cleavage. The biological activity can be assessed in ways known to one of ordinary skill in the art and includes, without limitation, in vitro cleavage assays or functional assays.

Delivery Vehicles

Delivery vehicles as used herein, include any types of molecules for delivery of the compositions embodied herein, both for in vitro or in vivo delivery. Examples, include, without limitation: expression vectors, nanoparticles, colloidal compositions, lipids, liposomes, nanosomes, carbohydrates, organic or inorganic compositions and the like.

In some embodiments, a delivery vehicle is an expression vector, wherein the expression vector comprises an isolated nucleic acid sequence encoding a Clustered Regularly Interspaced Short Palindromic Repeat (CRISPR)-associated endonuclease and at least one guide RNA (gRNA), the gRNA being complementary to a target nucleic acid sequence in a retrovirus genome.

Recombinant constructs are also provided herein and can be used to transform cells in order to express Cas9 and/or a guide RNA complementary to a target sequence in HIV. A recombinant nucleic acid construct comprises a nucleic acid encoding a Cas9 and/or a guide RNA complementary to a target sequence in HIV as described herein, operably linked to a regulatory region suitable for expressing the Cas9 and/or a guide RNA complementary to a target sequence in HIV in the cell. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for Cas9 can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

In one embodiment, the viral vector is an adenovirus vector, an adeno-associated viral vector (AAV), or derivatives thereof. The adeno-associated viral vector comprises AAV serotypes 1, 2, 3, 4, 5, 6, 7, 8, 9, 10, 11, DJ or DJ/8. In one embodiment, the AAV vector is AAV serotype 9. (AAV$_9$).

Additional expression vectors also can include, for example, segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2 μplasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences.

Yeast expression systems can also be used. For example, the non-fusion pYES2 vector (XbaI, SphI, ShoI, NotI, GstXI, EcoRI, BstXI, BamH1, SacI, Kpn1, and HindIII cloning sites; Invitrogen) or the fusion pYESHisA, B, C (XbaI, SphI, ShoI, NotI, BstXI, EcoRI, BamH1, SacI, KpnI, and HindIII cloning sites, N-terminal peptide purified with ProBond resin and cleaved with enterokinase; Invitrogen), to mention just two, can be employed according to the invention. A yeast two-hybrid expression system can also be prepared in accordance with the invention.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Replication-defective recombinant adenoviral vectors, can be produced in accordance with known techniques. See, Quantin, et al., *Proc. Natl. Acad. Sci. USA,* 89:2581-2584 (1992); Stratford-Perricadet, et al., *J. Clin. Invest.,* 90:626-630 (1992); and Rosenfeld, et al., *Cell,* 68:143-155 (1992).

In embodiments, a viral vector comprises an adenovirus vector, an adeno-associated viral vector (AAV), or derivatives thereof. The viral vector is in some embodiments an adeno-associated viral vector comprising AAV serotypes 1, 2, 3, 4, 5, 6, 7, 8, 9, 10, 11, DJ or DJ/8. In one embodiment, the AAV vector is AAV serotype 9. (AAV$_9$).

Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *Bio Techniques,* 34: 167-171 (2003). A large variety of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function (s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. *PNAS* 88: 8850-8854, 1991).

Suitable nucleic acid delivery systems include recombinant viral vector, typically sequence from at least one of an adenovirus, adenovirus-associated virus (AAV), helper-dependent adenovirus, retrovirus, or hemagglutinating virus of Japan-liposome (HVJ) complex. In such cases, the viral vector comprises a strong eukaryotic promoter operably linked to the polynucleotide e.g., a cytomegalovirus (CMV) promoter. The recombinant viral vector can include one or more of the polynucleotides therein, preferably about one polynucleotide. In some embodiments, the viral vector used in the invention methods has a pfu (plague forming units) of from about 10' to about $5 \times 10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Additional vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus.

DNA viral vectors include pox vectors such as orthopox or avipox vectors, herpesvirus vectors such as a herpes simplex I virus (HSV) vector [Geller, A. I. et al., *J. Neurochem*, 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.: U.S.A.*:90 7603 (1993); Geller, A. I., et al., *Proc Natl. Acad. Sci USA:* 87:1149 (1990)], Adenovirus Vectors [LeGal LaSalle et al., *Science*, 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated. The selection of appropriate promoters can readily be accomplished. An example of a suitable promoter is the 763-base-pair cytomegalovirus (CMV) promoter. Other suitable promoters which may be used for gene expression include, but are not limited to, the Rous sarcoma virus (RSV) (Davis, et al., *Hum Gene Ther* 4:151 (1993)), the SV40 early promoter region, the herpes thymidine kinase promoter, the regulatory sequences of the metallothionein (MMT) gene, prokaryotic expression vectors such as the β-lactamase promoter, the tac promoter, promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques*, 6:682 (1988). See also, Feigner and Holm, Bethesda Res. Lab. Focus, 11(2):21 (1989) and Maurer, R. A., Bethesda Res. Lab. Focus, 11(2):25 (1989).

Another delivery method is to use single stranded DNA producing vectors which can produce the expressed products intracellularly. See for example, Chen et al, *Bio Techniques*, 34: 167-171 (2003), which is incorporated herein, by reference, in its entirety.

Another delivery method is to use single stranded DNA producing vectors which can produce the expressed products intracellularly. See for example, Chen et al, *BioTechniques*, 34: 167-171 (2003), which is incorporated herein, by reference, in its entirety.

The nucleic acid sequences of the invention can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm). Another way to achieve uptake of the nucleic acid is using liposomes, prepared by standard methods. The nucleic acids can be incorporated alone into these delivery vehicles or co-incorporated with tissue-specific antibodies, for example antibodies that target cell types that are commonly latently infected reservoirs of HIV infection, for example, brain macrophages, microglia, astrocytes, and gut-associated lymphoid cells. Alternatively, one can prepare a molecular complex composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding an isolated nucleic acid sequence comprising a sequence encoding a CRISPR-associated endonuclease and a guide RNA complementary to a target sequence of a Retrovirus, as described above.

In some embodiments, the compositions of the invention can be formulated as a nanoparticle, for example, nanoparticles comprised of a core of high molecular weight linear polyethylenimine (LPEI) complexed with DNA and surrounded by a shell of polyethyleneglycol modified (PEGylated) low molecular weight LPEI.

In some embodiments, the compositions may be formulated as a topical gel for blocking sexual transmission of, for example the HIV virus. The topical gel can be applied directly to the skin or mucous membranes of the male or female genital region prior to sexual activity. Alternatively, or in addition the topical gel can be applied to the surface or contained within a male or female condom or diaphragm.

In some embodiments, the compositions can be formulated as a nanoparticle encapsulating the compositions embodied herein.

Regardless of whether compositions are administered as nucleic acids or polypeptides, they are formulated in such a way as to promote uptake by the mammalian cell. Useful vector systems and formulations are described above. In some embodiments the vector can deliver the compositions to a specific cell type. The invention is not so limited however, and other methods of DNA delivery such as chemical transfection, using, for example calcium phosphate, DEAE dextran, liposomes, lipoplexes, surfactants, and perfluoro chemical liquids are also contemplated, as are physical delivery methods, such as electroporation, micro injection, ballistic particles, and "gene gun" systems.

In other embodiments, the compositions comprise a cell which has been transformed or transfected with one or more Cas/gRNA vectors. In some embodiments, the methods of the invention can be applied ex vivo. That is, a subject's cells can be removed from the body and treated with the compositions in culture to excise, for example, HIV virus sequences and the treated cells returned to the subject's body. The cell can be the subject's cells or they can be haplotype matched or a cell line. The cells can be irradiated to prevent replication. In some embodiments, the cells are human leukocyte antigen (HLA)-matched, autologous, cell lines, or combinations thereof. In other embodiments the cells can be a stem cell. For example, an embryonic stem cell or an artificial pluripotent stem cell (induced pluripotent stem cell (iPS cell)). Embryonic stem cells (ES cells) and artificial pluripotent stem cells (induced pluripotent stem cell, iPS cells) have been established from many animal species, including humans. These types of pluripotent stem cells would be the most useful source of cells for regenerative medicine because these cells are capable of differentiation into almost all of the organs by appropriate induction of their differentiation, with retaining their ability of actively dividing while maintaining their pluripotency. iPS cells, in particular, can be established from self-derived somatic cells, and therefore are not likely to cause ethical and social issues, in comparison with ES cells which are produced by destruction of embryos. Further, iPS cells, which are self-derived cell, make it possible to avoid rejection reactions, which are the biggest obstacle to regenerative medicine or transplantation therapy.

The isolated nucleic acids can be easily delivered to a subject by methods known in the art, for example, methods which deliver siRNA. In some aspects, the Cas may be a fragment wherein the active domains of the Cas molecule are included, thereby cutting down on the size of the molecule. Thus, the, Cas9/gRNA molecules can be used clinically, similar to the approaches taken by current gene therapy. In particular, a Cas9/multiplex gRNA stable expression stem cell or iPS cells for cell transplantation therapy as well as vaccination can be developed for use in subjects.

Transduced cells are prepared for reinfusion according to established methods. After a period of about 2-4 weeks in culture, the cells may number between $1 \times 10^6$ and $1 \times 10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent. For administration, cells of the present invention can be administered at a rate determined by the $LD_{50}$ of the cell type, and the side effects of the cell type at various concentrations, as applied to the mass and overall health of the patient. Administration can be accomplished via single or divided doses. Adult stem cells may also be mobilized using exogenously administered factors that stimulate their production and egress from tissues or spaces that may include, but are not restricted to, bone marrow or adipose tissues.

Combination Therapies

In certain embodiments, a composition for eradicating a retrovirus in vitro or in vivo, comprises a therapeutically effective amount of: an isolated nucleic acid sequence encoding a Clustered Regularly Interspaced Short Palindromic Repeat (CRISPR)-associated endonuclease; at least one guide RNA (gRNA), the gRNA being complementary to a target nucleic acid sequence in a Retrovirus genome; an anti-viral agent or combinations thereof. In addition, one or more agents which alleviate any other symptoms that may be associated with the virus infection, e.g. fever, chills, headaches, secondary infections, can be administered in concert with, or as part of the pharmaceutical composition or at separate times. These agents comprise, without limitation, an anti-pyretic agent, anti-inflammatory agent, chemotherapeutic agent, or combinations thereof.

In certain embodiments, the anti-viral agent comprises therapeutically effective amounts of: antibodies, aptamers, adjuvants, anti-sense oligonucleotides, chemokines, cytokines, immune stimulating agents, immune modulating molecules, B-cell modulators, T-cell modulators, NK cell modulators, antigen presenting cell modulators, enzymes, siRNA's, interferon, ribavirin, ribozymes, protease inhibitors, anti-sense oligonucleotides, helicase inhibitors, polymerase inhibitors, helicase inhibitors, neuraminidase inhibitors, nucleoside reverse transcriptase inhibitors, non-nucleoside reverse transcriptase inhibitors, purine nucleosides, chemokine receptor antagonists, interleukins, vaccines or combinations thereof.

The immune-modulating molecules comprise, but are not limited to cytokines, lymphokines, T cell co-stimulatory ligands, etc. An immune-modulating molecule positively and/or negatively influences the humoral and/or cellular immune system, particularly its cellular and/or non-cellular components, its functions, and/or its interactions with other physiological systems. The immune-modulating molecule may be selected from the group comprising cytokines, chemokines, macrophage migration inhibitory factor (MIF; as described, inter alia, in Bernhagen (1998), *Mol Med* 76(3-4); 151-61 or Metz (1997), *Adv Immunol* 66, 197-223), T-cell receptors or soluble MHC molecules. Such immune-modulating effector molecules are well known in the art and are described, inter alia, in Paul, "Fundamental immunology", Raven Press, New York (1989). In particular, known cytokines and chemokines are described in Meager, "The Molecular Biology of Cytokines" (1998), John Wiley & Sons, Ltd., Chichester, West Sussex, England; (Bacon (1998). Cytokine Growth Factor Rev 9(2):167-73; Oppenheim (1997). *Clin Cancer Res* 12, 2682-6; Taub, (1994) *Ther. Immunol.* 1(4), 229-46 or Michiel, (1992). *Semin Cancer Biol* 3(1), 3-15).

Immune cell activity that may be measured include, but is not limited to, (1) cell proliferation by measuring the DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

Also of interest are enzymes present in the lytic package that cytotoxic T lymphocytes or LAK cells deliver to their targets. Perforin, a pore-forming protein, and Fas ligand are major cytolytic molecules in these cells (Brandau et al., *Clin. Cancer Res.* 6:3729, 2000; Cruz et al., *Br. J. Cancer* 81:881, 1999). CTLs also express a family of at least 11 serine proteases termed granzymes, which have four primary substrate specificities (Kam et al., *Biochim. Biophys. Acta* 1477:307, 2000). Low concentrations of streptolysin O and pneumolysin facilitate granzyme B-dependent apoptosis (Browne et al., *Mol. Cell Biol.* 19:8604, 1999).

Other suitable effectors encode polypeptides having activity that is not itself toxic to a cell, but renders the cell sensitive to an otherwise nontoxic compound—either by metabolically altering the cell, or by changing a non-toxic prodrug into a lethal drug. Exemplary is thymidine kinase (tk), such as may be derived from a herpes simplex virus, and catalytically equivalent variants. The HSV tk converts the anti-herpetic agent ganciclovir (GCV) to a toxic product that interferes with DNA replication in proliferating cells.

In certain embodiments, the antiviral agent comprises natural or recombinant interferon-alpha (IFNα), interferon-beta (IFNβ), interferon-gamma (IFNγ), interferon tau (IFNτ), interferon omega (IFNω), or combinations thereof. In some embodiments, the interferon is IFNγ. Any of these interferons can be stabilized or otherwise modified to improve the tolerance and biological stability or other biological properties. One common modification is pegylation (modification with polyethylene glycol).

Pharmaceutical Compositions

As described above, the compositions of the present invention can be prepared in a variety of ways known to one of ordinary skill in the art. Regardless of their original source or the manner in which they are obtained, the compositions of the invention can be formulated in accordance with their use. For example, the nucleic acids and vectors described above can be formulated within compositions for application to cells in tissue culture or for administration to a patient or subject. Any of the pharmaceutical compositions of the invention can be formulated for use in the preparation of a medicament, and particular uses are indicated below in the context of treatment, e.g., the treatment of a subject having an HIV infection or at risk for contracting and HIV infection. When employed as pharmaceuticals, any of the nucleic acids and vectors can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intra-arterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, nucleic acids and vectors described herein in combination with one or more pharmaceutically acceptable carriers. The term pharmaceutically acceptable carrier, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid.

The nucleic acid sequences of the invention can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm). Another way to achieve uptake of the nucleic acid is using liposomes, prepared by standard methods. The nucleic acids can be incorporated alone into these delivery vehicles or co-incorporated with tissue-specific antibodies, for example antibodies that target cell types that are commonly latently infected reservoirs of HIV infection, for example, brain macrophages, microglia, astrocytes, and gut-associated lymphoid cells. Alternatively, one can prepare a molecular complex composed of a plasmid or other vector attached to poly-L-lysine by electrostatic or covalent forces. Poly-L-lysine binds to a ligand that can bind to a receptor on target cells. Delivery of naked DNA (i.e., without a delivery vehicle) to an intramuscular, intradermal, or subcutaneous site, is another means to achieve in vivo expression. In the relevant polynucleotides (e.g., expression vectors) the nucleic acid sequence encoding an isolated nucleic acid sequence comprising a sequence encoding a CRISPR-associated endonuclease and a guide RNA is operatively linked to a promoter or enhancer-promoter combination. Promoters and enhancers are described above.

The nucleic acids and vectors may also be applied to a surface of a device (e.g., a catheter) or contained within a pump, patch, or other drug delivery device. The nucleic acids and vectors of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

In some embodiments, the compositions may be formulated as a topical gel for blocking sexual transmission of HIV. The topical gel can be applied directly to the skin or mucous membranes of the male or female genital region prior to sexual activity. Alternatively, or in addition the topical gel can be applied to the surface or contained within a male or female condom or diaphragm.

In some embodiments, the compositions can be formulated as a nanoparticle encapsulating a nucleic acid encoding Cas9 or a variant Cas9 and a guide RNA sequence complementary to a target HIV or vector comprising a nucleic acid encoding Cas9 and a guide RNA sequence complementary to a target HIV. Alternatively, the compositions can be formulated as a nanoparticle encapsulating a CRISPR-associated endonuclease polypeptide, e.g., Cas9 or a variant Cas9 and a guide RNA sequence complementary to a target.

The present formulations can encompass a vector encoding Cas9 and a guide RNA sequence complementary to a target HIV. The guide RNA sequence can include a sequence complementary to a single region, e.g. LTR A, B, C, or D or it can include any combination of sequences complementary to LTR A, B, C, and D. Alternatively the sequence encoding Cas9 and the sequence encoding the guide RNA sequence can be on separate vectors.

Methods of Treatment

The compositions disclosed herein are generally and variously useful for treatment of a subject having a retroviral infection, e.g., an HIV infection. The methods are useful for targeting any HIV, for example, HIV-1, HIV-2, and any circulating recombinant form thereof. A subject is effectively treated whenever a clinically beneficial result ensues. This may mean, for example, a complete resolution of the symptoms of a disease, a decrease in the severity of the symptoms of the disease, or a slowing of the disease's progression. These methods can further include the steps of a) identifying a subject (e.g., a patient and, more specifically, a human patient) who has an HIV infection; and b) providing to the subject a composition comprising a nucleic acid encoding a CRISPR-associated nuclease, e.g., Cas9, and a guide RNA complementary to an HIV target sequence, e.g. an HIV LTR. A subject can be identified using standard clinical tests, for example, immunoassays to detect the presence of HIV antibodies or the HIV polypeptide p24 in the subject's serum, or through HIV nucleic acid amplification assays. An amount of such a composition provided to the subject that results in a complete resolution of the symptoms of the infection, a decrease in the severity of the symptoms of the infection, or a slowing of the infection's progression is considered a therapeutically effective amount. The present methods may also include a monitoring step to help optimize dosing and scheduling as well as predict outcome. In some methods of the present invention, one can first determine whether a patient has a latent HIV-1 infection, and then make a determination as to whether or not to treat the patient with one or more of the compositions described herein. Monitoring can also be used to detect the onset of drug resistance and to rapidly distinguish responsive patients from nonresponsive patients. In some embodiments, the methods can further include the step of determining the nucleic acid sequence of the particular HIV harbored by the patient and then designing the guide RNA to be complementary to those particular sequences. For example, one can determine the nucleic acid sequence of a subject's LTR U3, R or U5 region and then design one or more guide RNAs to be precisely complementary to the patient's sequences.

The compositions are also useful for the treatment, for example, as a prophylactic treatment, of a subject at risk for having a retroviral infection, e.g., an HIV infection. These methods can further include the steps of a) identifying a subject at risk for having an HIV infection; b) providing to the subject a composition comprising a nucleic acid encoding a CRISPR-associated nuclease, e.g., Cas9, and a guide RNA complementary to an HIV target sequence, e.g. an HIV LTR. A subject at risk for having an HIV infection can be, for example, any sexually active individual engaging in unprotected sex, i.e., engaging in sexual activity without the use of a condom; a sexually active individual having another sexually transmitted infection; an intravenous drug user; or an uncircumcised man. A subject at risk for having an HIV infection can be, for example, an individual whose occupation may bring him or her into contact with HIV-infected populations, e.g., healthcare workers or first responders. A subject at risk for having an HIV infection can be, for example, an inmate in a correctional setting or a sex worker, that is, an individual who uses sexual activity for income employment or nonmonetary items such as food, drugs, or shelter.

The compositions can also be administered to a pregnant or lactating woman having an HIV infection in order to reduce the likelihood of transmission of HIV from the mother to her offspring. A pregnant woman infected with HIV can pass the virus to her offspring transplacentally in utero, at the time of delivery through the birth canal or following delivery, through breast milk. The compositions disclosed herein can be administered to the HIV infected mother either prenatally, perinatally or postnatally during the breast-feeding period, or any combination of prenatal, perinatal, and postnatal administration. Compositions can be administered to the mother along with standard antiretroviral therapies as described below. In some embodiments, the compositions of the invention are also administered to the infant immediately following delivery and, in some embodiments, at intervals thereafter. The infant also can receive standard antiretroviral therapy.

The methods and compositions disclosed herein are useful for the treatment of retroviral infections. Exemplary retroviruses include human immunodeficiency viruses, e.g. HIV-1, HIV-2; simian immunodeficiency virus (SIV); feline immunodeficiency virus (FIV); bovine immunodeficiency virus (BIV); equine infectious anemia virus (EIAV); and caprine arthritis/encephalitis virus (CAEV). The methods disclosed herein can be applied to a wide range of species, e.g., humans, non-human primates (e.g., monkeys), horses or other livestock, dogs, cats, ferrets or other mammals kept as pets, rats, mice, or other laboratory animals.

The methods of the invention can be expressed in terms of the preparation of a medicament. Accordingly, the invention encompasses the use of the agents and compositions described herein in the preparation of a medicament. The compounds described herein are useful in therapeutic compositions and regimens or for the manufacture of a medicament for use in treatment of diseases or conditions as described herein.

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinicians. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a compound can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compounds can be administered once (or twice, three times, etc.) daily, weekly, monthly, or yearly.

An effective amount of any composition provided herein can be administered to an individual in need of treatment. An effective amount induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

The compositions may also be administered with another therapeutic agent, for example, an anti-retroviral agent, used in HAART. Exemplary antiretroviral agents include reverse transcriptase inhibitors (e.g., nucleoside/nucleotide reverse transcriptase inhibitors, zidovudine, emtricitabine, lamivudine and tenofovir; and non-nucleoside reverse transcriptase inhibitors such as efavirenz, nevirapine, rilpivirine); protease inhibitors, e.g., tipiravir, darunavir, indinavir; entry inhibitors, e.g., maraviroc; fusion inhibitors, e.g., enfuvirtide; or integrase inhibitors e.g., raltegravir, dolutegravir. Exemplary antiretroviral agents can also include multi-class combination agents for example, combinations of emtricitabine, efavirenz, and tenofovir; combinations of emtricitabine; rilpivirine, and tenofovir; or combinations of elvitegravir, cobicistat, emtricitabine and tenofovir.

Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks. The therapeutic agents may be administered under a metronomic regimen, e.g., continuous low-doses of a therapeutic agent.

Dosage, toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compositions lies preferably within a range of circulating concentrations that include the $ED_{50}$ with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range that includes the IC$_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As described, a therapeutically effective amount of a composition (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

The compositions described herein are suitable for use in a variety of drug delivery systems described above. Additionally, in order to enhance the in vivo serum half-life of the administered compound, the compositions may be encapsulated, introduced into the lumen of liposomes, prepared as a colloid, or other conventional techniques may be employed which provide an extended serum half-life of the compositions. A variety of methods are available for preparing liposomes, as described in, e.g., Szoka, et al., U.S. Pat. Nos. 4,235,871, 4,501,728 and 4,837,028 each of which is incorporated herein by reference. Furthermore, one may administer the drug in a targeted drug delivery system, for example, in a liposome coated with a tissue-specific antibody. The liposomes will be targeted to and taken up selectively by the organ.

Also provided, are methods of inactivating a retrovirus, for example, a lentivirus such as a human immunodeficiency virus, a simian immunodeficiency virus, a feline immunodeficiency virus, or a bovine immunodeficiency virus in a mammalian cell. The human immunodeficiency virus can be HIV-1 or HIV-2. The human immunodeficiency virus can be a chromosomally integrated provirus. The mammalian cell can be any cell type infected by HIV, including, but not limited to CD4$^+$ lymphocytes, macrophages, fibroblasts, monocytes, T lymphocytes, B lymphocytes, natural killer cells, dendritic cells such as Langerhans cells and follicular dendritic cells, hematopoietic stem cells, endothelial cells, brain microglial cells, and gastrointestinal epithelial cells. Such cell types include those cell types that are typically infected during a primary infection, for example, a CD4$^+$ lymphocyte, a macrophage, or a Langerhans cell, as well as those cell types that make up latent HIV reservoirs, i.e., a latently infected cell.

The methods can include administering to a subject a composition comprising an expression vector encoding a gene editing complex comprising a CRISPR-associated endonuclease and one or more guide RNAs wherein the guide RNA is complementary to a target nucleic acid sequence in the retrovirus. In a preferred embodiment, as previously described, the method of inactivating a proviral DNA integrated into the genome of a host cell latently infected with a retrovirus includes the steps of treating the host cell by administering to a subject, a composition comprising a CRISPR-associated endonuclease, and two or more different guide RNAs (gRNAs), wherein each of the at least two gRNAs is complementary to a different target nucleic acid sequence in the proviral DNA; and inactivating the proviral DNA. The at least two gRNAs can be configured as a single sequence or as a combination of one or more different sequences, e.g., a multiplex configuration. Multiplex configurations can include combinations of two, three, four, five, six, seven, eight, nine, ten, or more different gRNAs, for example any combination of sequences in U3, R, or U5. In some embodiments, combinations of LTR A, LTR B, LTR C and LTR D can be used. In experiments described in the Examples, the use of two different gRNAs caused the excision of the viral sequences between the cleavage sites recognized by the CRISPR endonuclease. The excised region can include the entire HIV-1 genome. The treating step can take place in vivo, that is, the compositions can be administered directly to a subject having HIV infection. The methods are not so limited however, and the treating step can take place ex vivo. For example, a cell or plurality of cells, or a tissue explant, can be removed from a subject having an HIV infection and placed in culture, and then treated with a composition comprising a CRISPR-associated endonuclease and a guide RNA wherein the guide RNA is complementary to the nucleic acid sequence in the human immunodeficiency virus. As described above, the composition can be a nucleic acid encoding a CRISPR-associated endonuclease and a guide RNA wherein the guide RNA is complementary to the nucleic acid sequence in the human immunodeficiency virus; an expression vector comprising the nucleic acid sequence; or a pharmaceutical composition comprising a nucleic acid encoding a CRISPR-associated endonuclease and a guide RNA wherein the guide RNA is complementary to the nucleic acid sequence in the human immunodeficiency virus; or an expression vector comprising the nucleic acid sequence. In some embodiments, the gene editing complex can comprise a CRISPR-associated endonuclease polypeptide and a guide RNA wherein the guide RNA is complementary to the nucleic acid sequence in the human immunodeficiency virus.

Regardless of whether compositions are administered as nucleic acids or polypeptides, they are formulated in such a way as to promote uptake by the mammalian cell. Useful vector systems and formulations are described above. In some embodiments the vector can deliver the compositions to a specific cell type. The invention is not so limited however, and other methods of DNA delivery such as chemical transfection, using, for example calcium phosphate, DEAE dextran, liposomes, lipoplexes, surfactants, and perfluoro chemical liquids are also contemplated, as are physical delivery methods, such as electroporation, micro injection, ballistic particles, and "gene gun" systems.

Standard methods, for example, immunoassays to detect the CRISPR-associated endonuclease, or nucleic acid-based assays such as PCR to detect the gRNA, can be used to confirm that the complex has been taken up and expressed by the cell into which it has been introduced. The engineered cells can then be reintroduced into the subject from whom they were derived as described below.

The gene editing complex comprises a CRISPR-associated nuclease, e.g., Cas9, or homologues thereof, and a guide RNA complementary to the retroviral target sequence, for example, an HIV target sequence. The gene editing complex can introduce various mutations into the proviral DNA. The mechanism by which such mutations inactivate the virus can vary, for example the mutation can affect proviral replication, viral gene expression or proviral excision. The mutations may be located in regulatory sequences or structural gene sequences and result in defective production of HIV. The mutation can comprise a deletion. The size of the deletion can vary from a single nucleotide base pair to about 10,000 base pairs. In some embodiments, the deletion can include all or substantially all of the proviral sequence. In some embodiments the deletion can include the entire proviral sequence. The mutation can comprise an insertion; that is the addition of one or more nucleotide base pairs to the pro-viral sequence. The size of the inserted sequence also may vary, for example from about one base pair to about 300 nucleotide base pairs. The mutation can comprise a point mutation, that is, the replacement of a single nucleotide with another nucleotide. Useful point mutations are those that have functional consequences, for example, mutations that result in the conversion of an amino acid codon into a termination codon or that result in the production of a nonfunctional protein.

In one embodiment, a method for inactivating proviral DNA integrated into the genome of a host cell, two different gRNA sequences are deployed, with each gRNA sequence targeting a different site in the proviral DNA. That is, the methods include the steps of exposing the host cell to a composition including an isolated nucleic acid, e.g. AAV$_9$ expression vector, encoding: a CRISPR-associated endonuclease; an isolated nucleic acid sequence encoding a first gRNA having a first spacer sequence that is complementary to a first target protospacer sequence in a proviral DNA; and an isolated nucleic acid encoding a second gRNA having a second spacer sequence that is complementary to a second target protospacer sequence in the proviral DNA; expressing in the host cell the CRISPR-associated endonuclease, the first gRNA, and the second gRNA; assembling, in the host cell, a first gene editing complex including the CRISPR-associated endonuclease and the first gRNA; and a second gene editing complex including the CRISPR-associated endonuclease and the second gRNA; directing the first gene editing complex to the first target protospacer sequence by complementary base pairing between the first spacer sequence and the first target protospacer sequence; directing the second gene editing complex to the second target protospacer sequence by complementary base pairing between the second spacer sequence and the second target protospacer sequence; cleaving the proviral DNA at the first target protospacer sequence with the CRISPR-associated endonuclease; cleaving the proviral DNA at the second target protospacer sequence with the CRISPR-associated endonuclease; and inducing at least one mutation in the proviral DNA. The same multiplex method is readily incorporated into methods for treating a subject having a human immunodeficiency virus, and for reducing the risk of a human immunodeficiency virus infection. It will be understood that the term "composition" can include not only a mixture of components, but also separate components that are not necessarily administered simultaneously. As a non-limiting example, a composition according to the present invention can include separate component preparations of nucleic acid sequences, e.g. AAV$_9$ expression vector encoding a Cas9 nuclease, a first gRNA, and a second gRNA, with each component being administered sequentially in an infusion, during a time frame that results in a host cell being exposed to all three components.

In other embodiments, the compositions comprise a cell which has been transformed or transfected with one or more Cas/gRNA vectors. In some embodiments, the methods of the invention can be applied ex vivo. That is, a subject's cells can be removed from the body and treated with the compositions in culture to excise HIV sequences and the treated cells returned to the subject's body. The cell can be the subject's cells or they can be haplotype matched or a cell line. The cells can be irradiated to prevent replication. In some embodiments, the cells are human leukocyte antigen (HLA)-matched, autologous, cell lines, or combinations thereof. In other embodiments the cells can be a stem cell. For example, an embryonic stem cell or an artificial pluripotent stem cell (induced pluripotent stem cell (iPS cell)). Embryonic stem cells (ES cells) and artificial pluripotent stem cells (induced pluripotent stem cell, iPS cells) have been established from many animal species, including humans. These types of pluripotent stem cells would be the most useful source of cells for regenerative medicine because these cells are capable of differentiation into almost all of the organs by appropriate induction of their differentiation, with retaining their ability of actively dividing while maintaining their pluripotency. iPS cells, in particular, can be established from self-derived somatic cells, and therefore are not likely to cause ethical and social issues, in comparison with ES cells which are produced by destruction of embryos. Further, iPS cells, which are self-derived cell, make it possible to avoid rejection reactions, which are the biggest obstacle to regenerative medicine or transplantation therapy.

The gRNA expression cassette can be easily delivered to a subject by methods known in the art, for example, methods which deliver siRNA. In some aspects, the Cas may be a fragment wherein the active domains of the Cas molecule are included, thereby cutting down on the size of the molecule. Thus, the, Cas9/gRNA molecules can be used clinically, similar to the approaches taken by current gene therapy. In particular, a Cas9/multiplex gRNA stable expression stem cell or iPS cells for cell transplantation therapy as well as HIV-1 vaccination will be developed for use in subjects.

Transduced cells are prepared for reinfusion according to established methods. After a period of about 2-4 weeks in culture, the cells may number between $1\times10^6$ and $1\times10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent. For administration, cells of the present invention can be administered at a rate determined by the $LD_{50}$ of the cell type, and the side effects of the cell type at various concentrations, as applied to the mass and overall health of the patient. Administration can be accomplished via single or divided doses. Adult stem cells may also be mobilized using exogenously administered factors that stimulate their production and egress from tissues or spaces that may include, but are not restricted to, bone marrow or adipose tissues.

Kits

The compositions described herein can be packaged in suitable containers labeled, for example, for use as a therapy to treat a subject having a retroviral infection, for example, an HIV infection or a subject at for contracting a retroviral infection, for example, an HIV infection. The containers can include a composition comprising a nucleic acid sequence, e.g. AAV$_9$ expression vector encoding a CRISPR-associated endonuclease, for example, a Cas9 endonuclease, and a guide RNA complementary to a target sequence in a human immunodeficiency virus, or a vector encoding that nucleic acid, and one or more of a suitable stabilizer, carrier molecule, flavoring, and/or the like, as appropriate for the intended use. Accordingly, packaged products (e.g., sterile containers containing one or more of the compositions described herein and packaged for storage, shipment, or sale at concentrated or ready-to-use concentrations) and kits, including at least one composition of the invention, e.g., a nucleic acid sequence encoding a CRISPR-associated endonuclease, for example, a Cas9 endonuclease, and a guide RNA complementary to a target sequence in a human immunodeficiency virus, or a vector encoding that nucleic acid and instructions for use, are also within the scope of the invention. A product can include a container (e.g., a vial, jar, bottle, bag, or the like) containing one or more compositions of the invention. In addition, an article of manufacture further may include, for example, packaging materials, instructions for use, syringes, delivery devices, buffers or other control reagents for treating or monitoring the condition for which prophylaxis or treatment is required.

In some embodiments, the kits can include one or more additional antiretroviral agents, for example, a reverse transcriptase inhibitor, a protease inhibitor or an entry inhibitor. The additional agents can be packaged together in the same container as a nucleic acid sequence encoding a CRISPR-associated endonuclease, for example, a Cas9 endonuclease, and a guide RNA complementary to a target sequence in a human immunodeficiency virus, or a vector encoding that nucleic acid or they can be packaged separately. The nucleic acid sequence encoding a CRISPR-associated endonuclease, for example, a Cas9 endonuclease, and a guide RNA complementary to a target sequence in a human immunodeficiency virus, or a vector encoding that nucleic acid and the additional agent may be combined just before use or administered separately.

The product may also include a legend (e.g., a printed label or insert or other medium describing the product's use (e.g., an audio- or videotape)). The legend can be associated with the container (e.g., affixed to the container) and can describe the manner in which the compositions therein should be administered (e.g., the frequency and route of administration), indications therefor, and other uses. The compositions can be ready for administration (e.g., present in dose-appropriate units), and may include one or more additional pharmaceutically acceptable adjuvants, carriers or other diluents and/or an additional therapeutic agent. Alternatively, the compositions can be provided in a concentrated form with a diluent and instructions for dilution.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention. Embodiments of inventive compositions and methods are illustrated in the following examples.

Examples

Example 1: Excision of HIV-I DNA by Gene Editing: In Vivo Study

A CRISPR/Cas9 gene editing strategy was developed to eliminate integrated HIV-1 DNA sequences from latently infected human cells and animal disease models. The efficiency of HIV-1 DNA elimination was investigated from murine tissues that harbored the viral genome.

Materials and Methods

Construction of the AA V9 delivery vector. The background plasmid for creating the AAV delivery system was px601-AAV-CMV::NLS-SaCas9-NLS-3×HA-bGHpA;U6::Bsa1-sgRNA, abbreviated as "pX601" (Ran F A, et al. *Nature* 2015; 520:186-191). Oligonucleotides encompassing the DNA sequences corresponding to the LTR and Gag targets were cloned in front of the U6 promoter at the Bsa1 site in pX601. gRNA sequences targeting LTR and Gag are shown in FIG. 1A and were as follows, with PAM sequences indicated in bold: gRNA LTR-1: GGA TCA GAT ATC CAC TGA CCT TTG GAT (SEQ ID NO: 77); gRNA Gag D: GGA TAG ATG TAA AAG ACA CCA AGG AGG (SEQ ID NO: 78). After confirmation by sequencing, 20 ng of pX601 saCas9 gRNA HIV-1 LTR1/GagD plasmid was provided to the Penn Vector Core, Gene Therapy Program (Perelman School of Medicine, University of Pennsylvania) for plasmid DNA production, DNA structure/sequence analysis, packaging in AAV serotype and high titer production.

Mouse embryo fibroblasts (MEFs). HIV-1 Tg26 Mouse embryo fibroblasts (MEFs) were prepared from 17 day gestation embryos by mechanical and enzymatic dissociation and maintained in DMEM supplemented with 10% fetal bovine serum. MEF cells were prepared as previously described (Behringer et al., Manipulating the mouse embryo: A laboratory manual, Fourth edition. Cold Spring Harbor Laboratory Press, 2014) and genotyped by PCR using primers specific for the HIV transgene (Kopp J B, et al. *Proc Natl Acad Sci USA* 1992; 89:1577-1581; Dickie P, et al. *Virology* 1991; 185:109-119).

In vitro transduction of Tg26MEF. Tg26 MEF cells were transduced with AAV-CRISPR/Cas9 at MOI $10^5$ and $10^6$. Viral inoculum was prepared in Opti-Mem, cells were incubated with the virus for 1 hour in minimal volume (0.5 ml/well in a 6 well plate) then 1 ml of growth medium was added and left overnight. The next day, inoculum was removed, cells were washed with PBS and fed fresh growth medium. Cells were harvested for DNA analysis one week after transduction.

In vivo rAAV9:saCas9 gRNA administration. One hundred µl of AAV9 CRISPR/Cas9 of 100 µl of PBS for control animals was injected via tail vein into mice at day 0 and day 5. At day 5, one pair (AAV and PBS) animals were subjected to a retro orbital bleed for a blood sample, euthanized and tissues harvested. The second pair of animals received a second tail vein injection of AAV-Cas9 or PBS, and were euthanized for harvest of tissue 7 days later after retro orbital bleed. Tissues harvested were brain, heart, lung, liver, kidney, spleen and peripheral blood for lymphocyte recovery.

DNA analysis. Genomic DNA was isolated from cells/tissues using NUCLEOSPIN Tissue kit (Macherey-Nagel) according to the manufacturer's protocol. 25 ng of genomic DNA was subjected to PCR using Terra PCR direct polymerase mix (Takara, Clontech) under the following PCR conditions: 98° C. for 3 minutes, 35 cycles (98° C. for 10 s, 68° C. for 1.30 minutes), 68° C. for 5 minutes and resolved in 1% agarose gel. Nested PCRs were performed under the same conditions using 5 µl of first PCR reaction. PCR products were purified, cloned into TA vector (Invitrogen) and sent for Sanger sequencing (Genewiz, South Plainfield, NJ, USA) and aligned in Clustal Omega (EMBL-EBI) software (Cambridgeshire, UK) using HIV-1 $NL_{4-3}$ sequence as a reference.

RNA analysis. Total RNA was prepared from tissues using TRIzol reagent (Ambion, Foster City, CA, USA) according to manufacturer's protocol followed by DNAse I treatment and RNA cleanup using RNeasy Mini Prep Kit (Qiagen, Hilden, Germany). Next 1 µg of RNA was used for M-MLV reverse transcription reactions (Invitrogen). cDNA was diluted and quantified using TaqMan qPCR specific for HIV-1 Gag and Env genes and cellular rat beta-actin gene as a reference (for primers see Table 1). qPCR conditions: 98° C. 5 min, 45 cycles (98° C. 5 min, 45 cycles (98° C. 15 s, 62° C. 30 s with acquisition, 72° C. 1 min). Reactions were carried out and data analyzed in a LightCycler480 (Roche, Basel, Switzerland) using relative quantification mode.

Results

As a testing platform HIV-1 Tg26 transgenic mice, which carry a transgene derived from the genome of HIV-1NL$_4$-3 with a deletion of a 3.1 kb spanning the C-terminal of the Gag and the N-terminal of the Pol genes (FIG. 1A), were used. While no productive HIV-1 replication is reported, expression of viral transcripts, at low levels, has been detected in various tissues prior to disease onset (Curreli S, et al. *Retrovirology* 2013; 10:92; Kopp J B, et al., *Proc Natl Acad Sci USA* 1992; 89:1577-1581; Santoro T J, et al., *Virology,* 1994; 201:147-151). Select clinical features of HIV-1 infection and AIDS including HIV-associated nephropathy (HIVAN) are seen (Barisoni L, et al. *Kidney Int* 2000; 58:173-181; Dickie P, et al. *Virology* 1991; 185:109-119). Due to the early lethality of the mice, Tg26 mice were crossed into the C57BL/6L background to create animals where secondary disease is limited and mice can survive to 12 months of age. For delivery of genes expressing Cas9 and gRNAs, an AAV$_9$ vector was selected. One of the major challenges associated with the use of AAV vectors relates to its genome accepting capacity. To alleviate this problem, a smaller Cas9 or homologue, saCas9 (3.3 kDa), was selected which is derived from *Staphylococcus aureus* that can edit the genome with efficiency similar to that of the original Cas9 from *Streptococcus pyrogens* (spCas9), while being more than 1 kb shorter (Ran F A, et al. *Nature* 2015; 520:186-191). The gene encoding saCas9 along with DNA sequences corresponding to the two gRNAs for targeting the HIV-1 LTR (gRNA LTR 1) and the Gag gene (gRNA Gag D) were cloned into the AAV$_9$ vector DNA. FIG. 1A illustrates the structural organization of the HIV-1 genome highlighting the region of the viral gene that was deleted for creating the transgene in Tg26 mice and the position of gRNA LTR 1 and gRNA Gag D. As a first step, ex vivo studies were performed by developing a culture of mouse embryo fibroblasts (MEFs) from Tg26 animals and used them to assess the ability of the recombinant AAV$_9$ (rAAV9) containing saCas9/gRNAs, rAAV9:saCas9/gRNAs, in excising portions of integrated HIV-1 DNA. FIG. 1B illustrates results from PCR gene amplification utilizing a pair of primers (P1 and P2) spanning −413/−391 for the LTR and +888/+910 for the Gag gene (FIG. 1A).

Figure 3B:
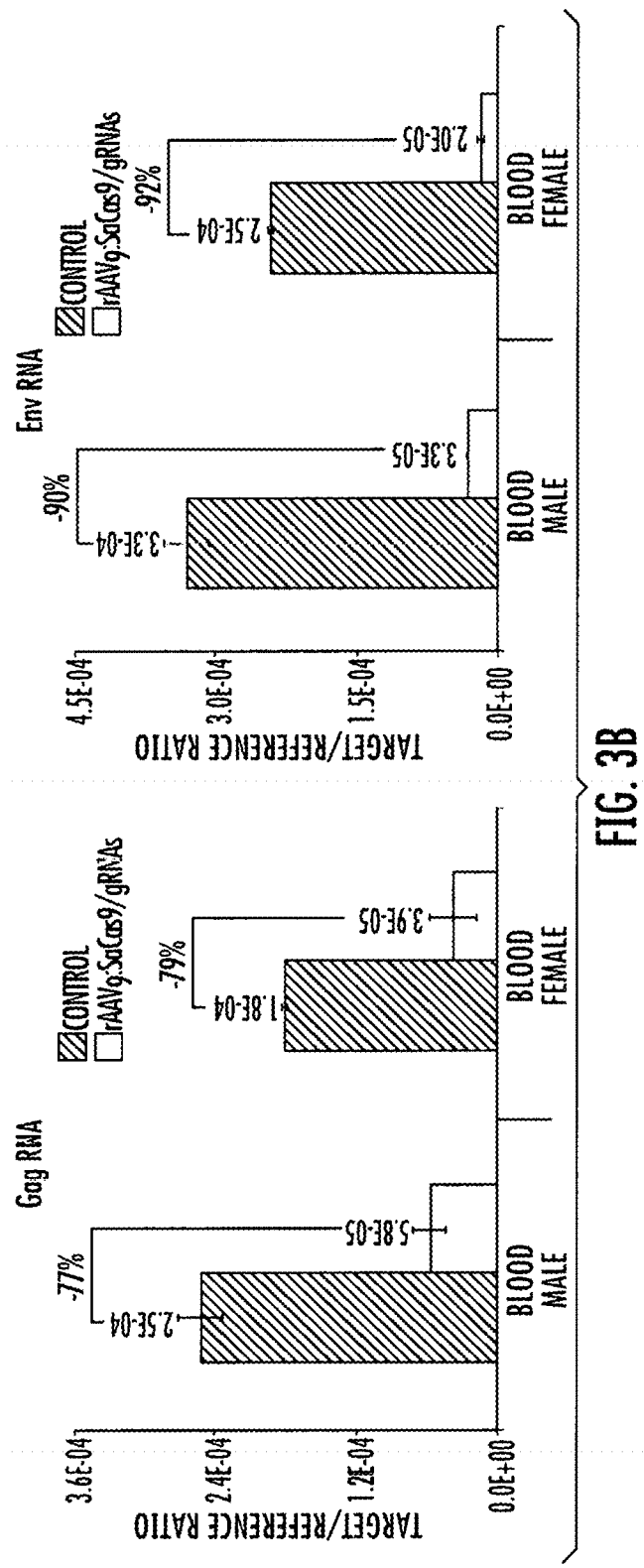

In addition to the expected full-length amplicon of 1323 bp, a smaller fragment of 345 bp was detected in rAAV9 treated cells. These were not seen in control untreated cells. Results from sequencing data verified excision of a 978 bp DNA fragment spanning between the two guide RNAs and re-joining the residual viral DNA after excision (as schematized in FIG. 1A). For in vivo studies two Tg26 animals and two age-matched (2 months) control mice were selected for tail vein injections of 10$^2$ functionally titered of rAAV9: saCas9/gRNA. After five days, the injections were repeated and 5 days later the animals were sacrificed and the liver, heart, spleen, lung, kidney, brain and blood lymphocytes were harvested (FIG. 2A). In a first pass experiment DNA from liver was analyzed by PCR amplification using P1 and P2 primers. Consistent with the results from MEF cell culture, results of gel analysis of PCR products showed a presence of a full-length (1323 bp) and a truncated (345 bp) DNA fragments after amplification from rAAV9:saCas9/ gRNA treated animals but not in age-matched control animals (FIG. 2B left). Extension of DNA amplification in the presence of a pair of nested primers, P1' (−375/−354) and P2' (+755/+763) (depicted in FIG. 1A) yielded an additional smaller DNA fragment of 160 bp (FIG. 2B, middle and right panels). Results from DNA sequencing of the 160 bp DNA verified excision of the 978 bp DNA sequence spanning between gRNA LTR 1 and gRNA Gag D (FIG. 2C). The effect of rAAV9:saCas9/gRNA on HIV-1 DNA in other tissues was assessed. As seen in FIG. 2D, a distinct 160 bp DNA fragment, indicative of excision of the HIV-1 DNA between the LTR and Gag genes by gRNAs LTR1 and gRNAs Gag D, as verified by DNA sequencing, was observed in all tissues of rAAV9:saCas9/gRNA treated animals (lane 2). These were not observed in control untreated animals (lane 1). The 160 bp amplicon produced upon treatment of MEFs with rAAV9 served as an additional control (Lane 3). In parallel studies the effect of the excision strategy was assessed in another small animal model, that is, rat, which encompasses the identical transgene used for the development of the mouse model. Here, a retroorbital route of inoculation of rAAV9.was employed. Thirty-day old rats injected twice with 2.73×10$^{12}$ of rAAV9:saCas9/gRNA at 5 day intervals led to the excision of segments of HIV-1 DNA spanning the 5'-LTR and the Gag gene from circulating lymphocytes, as examined by direct sequencing of the amplicon that was generated by target specific PCR. As illustrated in FIGS. 3A, 3B, a detailed analysis of the sequencing data from several PCR products of the excised fragments and their alignment with the reference HIV-1 DNA verified excision of the viral DNA with some variations in tissues from animals treated with rAAV9:saCas9/ gRNA. The level of viral gene expression was examined by measuring the levels of Gag and Env transcripts using quantitative RT-PCR. As seen in FIGS. 3A, 3B, the level of viral RNA was drastically decreased in circulating blood cells obtained from animals treated with rAAV9:Cas9/ gRNA, indicating that excision of the viral genome has a significant impact on the level of viral gene expression from the integrated copies of HIV-1 DNA. Examination of viral RNAs in lymph nodes also showed suppression of viral RNAs in the treated rats.

Table 1 shows the nucleotide sequences of PCR primers used. Table discloses SEQ ID NOS 79, 15 and 80-90, respectively, in order of appearance.

TABLE 1

Table 1 shows the nucleotide sequences of PCR primers used.
Nucleotide sequences of PCR primers

| Primer | Sequence |
| --- | --- |
| LTR-Gag PCR | |
| P1 (LTR F [−413/−391](T361)] | 5'-GATCTGTGGATCTACCACACAGA-3' |
| P2 [Gag R (+888 +910 (T45S)] | 5'-CCCACTGTGTTTAGCATGGTATT-3' |
| P1 [nested LTR F (−375/−354)] | 5'-TTGGCAGAACTACACACCAGGG-3 |
| P2 [nested Gag R (+744/+763)] | 5'-ACCATTTGCCCCTGGAGGTT-3 |
| Taqman qPCRs | |
| HIV-1 Env F | 5'-TCCTTGGGATGTTGATGATGT-3 |
| HIV-1 Env R | 5'-TGGCCCAAACATTATGTACC-3 |
| HIV-1 Env Probe | 5'-FAM-TGGTGGTTGGTTCTTTCCACACA-ZEN-IowaBlackFQ-3 |
| HIV-1 Gag F | 5'-AAGTAGTGTGTGCCCGTCTG-3 |
| HIV-1 Gag R | 5'-TCGAGAGATCTCCTCTGGCT-3 |
| HIV-1 Gag Probe | 5'-FAM-CTGTTCGGGCGCCACTGCTA-ZEN-IowaBlackFQ-3 |
| Rn b-actin F | 5'-AGCGCAAGTACTCTGTGTGG-3' |
| Rn b-actin R | 5'-AACAGTCGGCCTAGAAGCAT-3 |
| Rn b-actin probe | 5'-FAM-CCTCCATGGTGCACCGCAA-ZEN-IowaBlackFQ-3 |

Discussion

It has been demonstrated herein, that the AAV$_9$-based saCas9/gRNA gene editing delivery system can excise a segment of integrated copies of the HIV-1 genome in transgenic mice carrying HIV-1 DNA sequences. These results show a similar ability of rAAV9 in delivering saCas9/gRNA to edit HIV-1 DNA in HIV-1 infected humanized mice. Further, these results demonstrate suppression of viral RNA production in the animals that were treated with the therapeutic rAAV and exhibit excision in the designated segments of the viral genome by saCas9/gRNAs in blood and lymph nodes.

The work is a step forward towards the utilization of CRISPR/Cas9 platform technology as a robust HIV-1 gene elimination strategy. In principle, this technology can be further refined and used, in tandem with an antiretroviral regimen to enhance the efficacy of editing and as such lead to a similar favorable outcome in infected animals and inevitably in humans. The ease of AAV delivery for the CRISPR/Cas9 technology and the flexibility of CRISPR/Cas9 in developing new gRNAs for targeting DNA sequences of HIV-1 with minor nucleotide variations brings additional values to this therapeutic platform for personalizing the cure strategy, if deemed appropriate.

Example 2: In Vivo Eradication of HIV Provirus by SaCas9 and Multiplex sgRNAs in Preclinical Animal Models In this study, a combination of sgRNAs targeting conserved HIV-1 regulatory and structural regions that efficiently eradicate HIV-1 genome with the saCas9/sgRNA system, were optimized and tested for feasibility and efficiency of duplex versus quadruplex sgRNAs with saCas9 in excising HIV-1 proviruses in vivo in both HIV-1 Tg26 transgenic mice and EcoHIV-enhanced firefly luciferase (eLuc)-infected mice (Rabinovich, B. A. et al. (2008) Proc Natl Acad Sci USA 105, 14342-14346; Potash, M. J. et al. Proc Natl Acad Sci USA 102, 3760-3765, doi:10.1073/pnas.0500649102 (2005)). Furthermore, it was demonstrated that the multiplex sgRNA/saCas9 delivered by all-in-one AAV vector can be used as pre-exposure prophylaxis (PrEP) in vivo.

Materials and Methods

Bioinformatics Design of gRNAs with High Efficiency. The Broad Institute gRNA designer tool for highly effective gRNA design was used (broadinstitute.org) because this tool also provides the extended spacer sequence (NNNN[20nt] NGGNNN) for spCas9 system. The SaCas9 PAM sequence for optimal on-target cleaving is NNGRRT. Only NGGRRT was used because it contains NGG PAM and thus can be used with the well-established spCas9 system. To test this, 3 sgRNAs targeting HIV-1 LTR promoter region, 3 sgRNA targeting Gag and 1 sgRNA targeting Pol were selected. The oligonucleotides for these sgRNA targets were listed in Table 2.

Plasmids and Cloning of Multiplex gRNA Expression AAV Vectors. The pNL4-3-EcoHIV-eLuc reporter virus was constructed as previously described (Yin, C. et al. AIDS, doi:10.1097/QAD.0000000000001079 (2016); Zhang, Y. et al. Scientific reports 5, 16277, doi:10.1038/srep16277 (2015)). A pair of oligonucleotides for each targeting site with 5'-CACC and 3'-AAAC overhang (Table 2) was obtained from AlphaDNA (Montreal, Canada). The target seed sequence was cloned via BsaI sites into pX601—AAV-CMV::NLS-SaCas9-NLS-3×HA-bGHpA;U6::BsaI-sgRNA (Addgene #61591; Ran, F. A. et al. Nature 520, 186-191, doi:10.1038/nature14299 (2015)). The pX601 AAV was digested with BsaI, treated with Antarctic Phosphatase, and purified with a Quick nucleotide removal kit (Qiagen). Equal amounts of complementary oligonucleotide were mixed in T4 polynucleotide kinase (PNK) buffer for annealing. These annealed seed pairs were phosphorylated with T4 PNK and ligated into the BsaI-digested AAV using T7 DNA ligase. The ligation mixture was transformed into Stabl3 competent cells. Positive clones were identified by PCR screening and verified by Sanger sequencing. For multiplex sgRNA cloning, two approaches were established: Double digestion traditional cloning and In-Fusion seamless PCR cloning. In the double digestion strategy, the target AAV vector was first digested with KpnI and blunted, and then digested with EcoRI; while the transfer insert harboring the expected sgRNA expression cassette was first digested with NotI and blunted, and then digested with EcoRI. The insert and the vector were purified with QIAquick Gel Extraction Kit followed by standard overhang/blunt end cloning. The positive duplex sgRNA-expressing AAV clones were identified by double digestion with NotI and BamHI or EcoRI. In the In-Fusion PCR cloning strategy, the target AAV vector was linearized with EcoRI and KpnI. The insertion fragment was produced via PCR using a pair of primer T795/T796 (Table 2) with a mutation of 3'-end KpnI site (for further adding of new sgRNAs) and the transfer sgRNA AAV vector as template. After purification, the linearized vector and the insertion PCR product were ligated using In-Fusion HD Cloning Kit (Clontech). The positive duplex sgRNA-expressing AAV clones were identified by double digestion with NotI and BamHI or EcoRI. Using similar proof of principle for both cloning strategies, the duplex sgRNA/saCas9 vector can serve as a target vector for inserting additional 1-n sgRNA expression cassettes. Only one caution is to ensure the absence of these digestion sites (KpnI, NotI, EcoRI) in the seed sequence of the selected sgRNAs.

Cell Culture, Transfection and Firefly-Luciferase Reporter Assay. HTEK293 T cells were cultured in high-glucose DMEM containing 10% FBS and antibiotics (100 U/ml penicillin and 100 µg/ml streptomycin) in a humidified atmosphere with 5% $CO_2$ at 37° C. For the luciferase reporter assay, cells were cultured in a 96-well plate ($3 \times 10^4$ cells/well) and were transfected with indicated plasmids using the standard calcium phosphate precipitation protocol. After 48 hours, the cell was lysed and assayed with the ONE-GLO luciferase assay system (Promega) in a 2104 ENVISION® Multilabel Reader (PerkinElmer).

TERRA™ PCR Direct Genotyping and Nested PCR. To perform high throughput genotyping using PCR, cells were seeded in 96-well plate and transfected with indicated vectors. After 48 hours, the media was removed and the cells were treated with 45 µl of 50 mM NaOH per well and incubated for 10 min at 95° C. After neutralization with 5 µl of 1M Tris-HCl (pH 8.0), 0.5 µl of the DNA extract was used in a 10 µl PCR reaction using the TERRA™ PCR Direct Polymerase Mix (Clontech) and indicated primers. For genotyping the excised HIV proviral DNA from the isolated tissues and organs from the EcoHIV-eLuc inoculated mice, each tissue was triturated by each individual pair of scissors to avoid cross-contamination, and then digested with Proteinase K in a lysis buffer consisting of 1% SDS, 10 mM Tris (pH 8.0), 5 mM EDTA and 100 mM NaCl in a 55° C. water bath. Genomic DNA was then extracted from the tissue lysates conventional phenol/chloroform extraction methods. For extracting the genomic DNA, RNA, and protein from specific Tg26 mouse tissues, tissue samples were broken up mechanically with a pestle and mortar, then processed with the NUCLEOSPIN® Tissue kit and NUCLEOSPIN® RNA/Protein kit (CLONTECH) according to the manufacturer's protocols to extract genomic DNA, RNA and Protein. To perform PCR genotyping, DNA samples were denatured at 98° C. for 3 min followed by two steps of conventional PCR for 35 cycles with annealing/extension step at 68° C. for 1 min/kb. For nested PCR, the first round of reaction was run for 22-25 cycles with indicated primers and the second round of PCR was run for 35 cycles with the nested PCR primers.

Figures 18A, 18B, 18C:
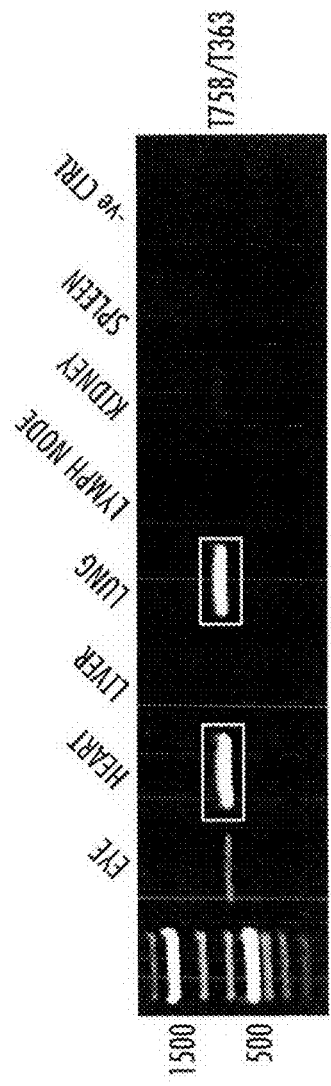
FIGS. 18A-18C show the excision of EcoHIV-eLuc by the quadruplex sgRNAs/saCas9 in the heart and lung tissues of NCr nude mice. The mice received an administration of EcoHIV-eLuc via retro-orbital injection at the right eye and then another injection of AAV-DJ8 carrying quadruplex sgRNA/saCas9 via the same injection route. Mice were sacrificed 2 weeks after the injection.

Quantitative reverse transcription-polymerase chain reaction (RT-qPCR). Total RNAs from indicated organs/tissues were extracted with an RNeasy Mini kit (Qiagen) as per manufacturer's instructions. The potentially residual genomic DNA was removed through on-column DNase digestion with an RNase-Free DNase Set (Qiagen). One µg of RNA for each sample was reversely transcribed into cDNAs using random hexanucleotide primers with a High Capacity cDNA Reverse Transcription Kit (Invitrogen, Grand Island, NY). Quantitative PCR (qPCR) analyses of cDNA or HIV genomic DNA were carried out in a Light-Cycler480 (Roche) using an SYBR® Green PCR Master Mix Kit (Applied Biosystems). The primer pairs for saCas9, Gag, Env, Tat were designed as shown in Table 2. The primers for human 32 microglobulin and mouse Ppia housekeeping genes were obtained from RealTimePrimers (Elkins Park, PA). The primers for HIV excision quantification were designed as shown in FIGS. 18A-18C. Each sample was tested in triplicate. Cycle threshold (Ct) values were obtained graphically for the target genes and house-keeping genes. The difference in Ct values between the housekeeping gene and target genes were represented as ΔCt values. The ΔΔCt values were obtained by subtracting the ΔCt values of control samples from those of experimental samples. Relative fold or percentage change in gene expression or HIV DNA excision was calculated as $2^{-\Delta\Delta C}t$. In some cases, the amplification curve and the melting peak curve were used for the comparative analysis.

AAV and EcoHIV-eLuc Packaging and Purification. Small and large scale preparation of AAV-DJ and AAV-DJ/8 were performed via AAV production service at ViGene Biosciences Inc. (Rockville, MD) following published protocols (Zolotukhin, S. et al. Gene Ther 6, 973-985 (1999)). Briefly, HEK293T cells were cotransfected with three vectors and the viral particles were harvested and purified by Iodixanol gradient ultracentrifugation. Viruses were concentrated and formulated in phosphate buffered saline. The virus titers were determined by the viral genome copy number in 1 ml sample (GC/ml) using real-time PCR with linearized genome plasmid as a standard.

Figures 22A, 22B:
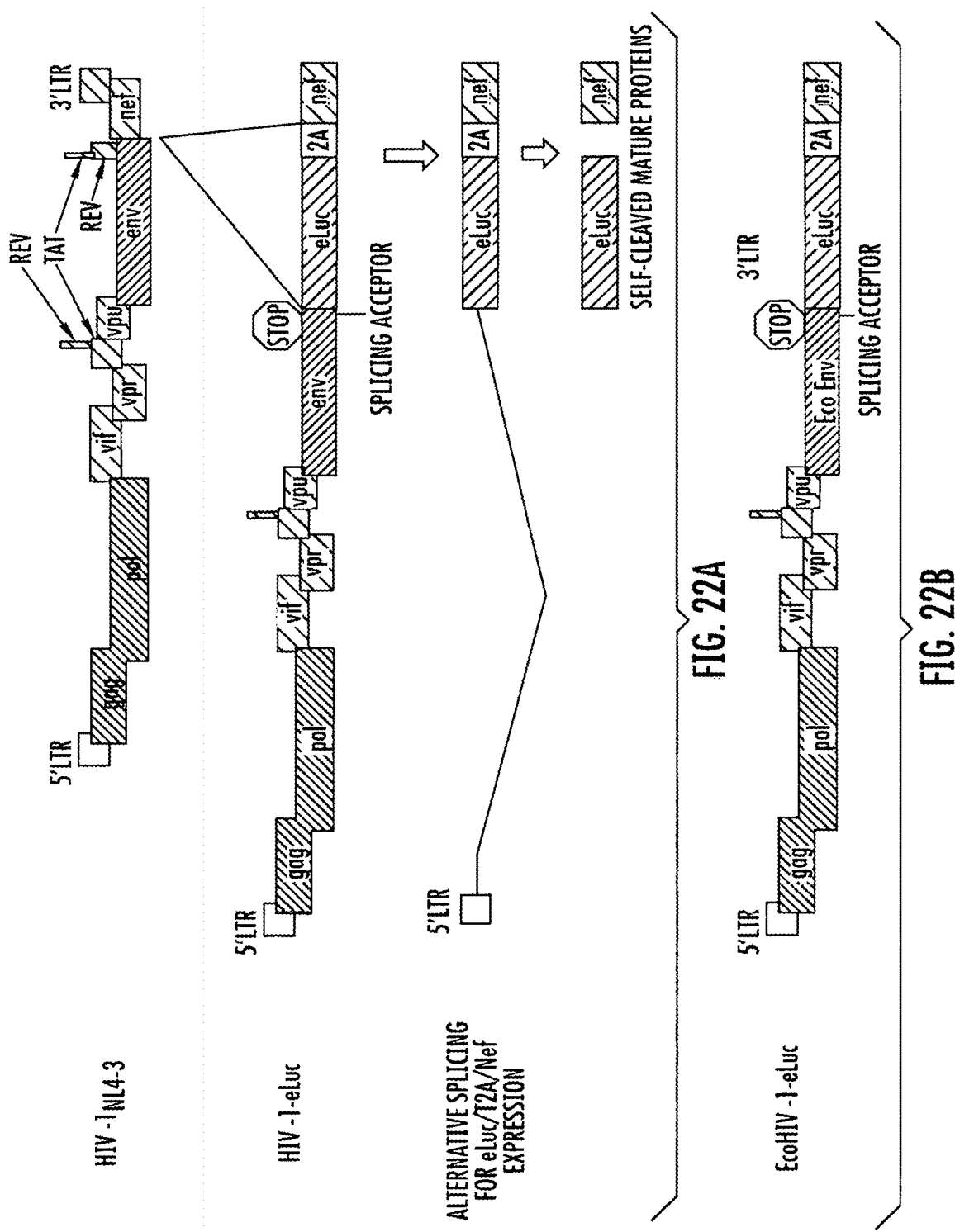
FIGS. 22A and 22B show schematics of $HIV_{NL-BaL}$-eLuc and EcoHIV-eLuc.

For packaging replication competent EcoHIV-eLuc and $HIV_{NL-BaL}$-eLuc, plasmid DNA encoding full length molecular clone of either EcoHIV or HIV-1 carrying BLI reporter (FIGS. 22A, 22B) was transferred into HEK293T cells (Invitrogen) using LIPOFECTAMINE 3000 (Invitrogen). At 24 h post transfection, media containing transfection reagent and DNA was aspirated and cells were washed twice with PBS. Fresh media was added. At 48 and 60 h post transfection, supernatants were collected and filtered through a 0.45 µm filter. The lentiviral supernatant was concentrated using the Lenti-X Concentrator (Clontech, CA, USA) following the manufacturer's instructions or using 20% sucrose density centrifugation at 20,000×g, 4° C., for 4 h. For EcoHIV-eLuc, the quantity of p24 was determined by ELISA (XpressBio, Frederick, MD) according to the manufacturer's protocol. The titer of $HIV_{NL-BaL}$-eLuc was determined on GHOST(3) X4/R5, for GFP expression analyzed by fluorescence-activated cell sorting (FACS) analysis.

Viral Inoculation of humanized BLT mice. All animal care and procedures were approved by the University of Pittsburgh or Temple University Institutional Animal Care and Use Committee (IACUC). Humanized BLT mice based on NSG® strain transplanted with human fetal liver, thymus and CD34+ cells isolated from the syngeneic liver were purchased from Jackson Lab (Bar Harbor, ME). For infection, mice were anesthetized via isoflurane inhalation (2-2.5% with a 2 L/min oxygen flow rate). Intravaginal inoculations (total $1\times10^6$ TCIU of $HIV_{NL-BaL}$-eLuc per mouse) were performed by slowly pipetting 20 μL of viral supernatant into the vaginal canal with a mid-size pipet tip. Intraperitoneal inoculations (total $1\times10^5$ TCIU of $HIV_{NL-BaL}$-eLuc per mouse) were performed by injecting 100 μL of indicated viral titer into the intraperitoneal cavity with a 29-gauge needle and insulin syringe. The HIV-infection in BLT mice were visualized using in vivo BLI to reveal longitudinal HIV dissemination. The chosen HIV-infected BLT mice were previously determined to show possible latency without detectable HIV-reporter activity in vivo for at least 70 days or longer prior to AAV-DJ/8/Cas9-sgRNA administration.

In vivo AAV Injection. For sgRNA/saCas9 gene delivery efficiency and functional assay in Tg26 transgenic mice, 100 μl unpurified AAV-DJ serotype or 5 μl purified AAV-DJ/8 serotype diluted in 1×DMEM without serum in a total volume of 100 μl were injected into animals via the tail vein. For mice injected with AAV-DJ, group 1 was sacrificed and group 2 was performed additional injection one week after the first injection. Group 2 was sacrificed one week after the second injection. Control mice were injected with AAV virus carrying an empty vector. For mice injected with AAV-DJ/8, the interval time between group 1 and group 2 was 2 weeks. Tissue samples of selected organs were broken up mechanically with pestle and mortar, then processed with NUCLEO-SPIN® Tissue kit and NUCLEOSPIN® RNA/Protein kit (CLONTECH) following the user manuals to extract genomic DNA, RNA and protein.

For in vivo injection of AAV-DJ/8 into NCr nude mice inoculated with EcoHIV-eLuc, total 10 μl of purified AAV-DJ/8 containing saCas9/sgRNA ($3.07\times10^{14}$ GC/ml) was first diluted in 90 μl of PBS for retro orbital injection into the blood sinus of the right eye of each mouse right after a retro orbital injection of a total 100 μl of EcoHIV-eLuc supernatant containing total 250 ng of p24 determined by ELISA (ZeptoMetrix) at the same injection site.

The quadruplex sgRNAs/saCas9 AAV-DJ/8 delivery in BLT mice was performed via intravaginal or intravenous or via both routes. The intravaginal inoculation was performed similar to the aforementioned HIV inoculation with a total 20 μl of PBS containing total $6.14\times10^{12}$ GC of AAV-DJ/8/saCas9-sgRNA per BLT mouse. The intravenous inoculation was administered using an insulin syringe with a 29-gauge needle via blood sinus of right eye (retro-orbital injection) with 100 μl of PBS containing total $6.14\times10^{12}$ GC of AAV-DJ/8/saCas9-sgRNA per BLT mouse.

Bioluminescence imaging (BLI). Imaging commenced at the indicated time points after viral inoculation. During all imaging, mice were anesthetized via isoflurane inhalation (2-2.5% with a 2 L/min oxygen flow rate). D-luciferin potassium salt (Gold BioTechnology, Olivette, MO) was dissolved in sterile PBS and injected intraperitoneally at a dose of 150 mg/kg body weight. Bioluminescence images were acquired for 2 min (Open light filter, binning 8×8, f/stop 1, field-of-view 100 mm) using an IVIS Lumina XR small animal optical imaging system (Perkin Elmer, Hopkinton, MA).

Image Analysis. All image analysis was performed using Living Image 4.3.1. Regions of interest (ROI) were drawn around the measured area or around the entire animal for comparison and average radiance values (units: $p/s/cm^2/str$) were used for all image evaluation. For display, images were windowed so that all light output above background levels adjacent to the mouse were seen. A maximum radiance value of 110,000 $p/s/cm^2/str$ was selected for the high end of the imaging scale and the background cutoff was set at 6,000 $p/s/cm^2/str$, which was the average light emission of the mice imaged at two different time points prior to viral inoculation.

Genomic DNA, RNA and protein extraction. Tissue samples of selected organs were broken up mechanically with pestle and mortar, then processed with NUCLEOSPIN® Tissue kit and NUCLEOSPIN® RNA/Protein kit (CLONTECH) following the user manuals to extract genomic DNA, RNA and Protein. Extracted tissues were minced with sterilized and contaminant-free scissors and resulting tissue was added to a lysis buffer (2.5 mM Tris-Base, 5 mM EDTA, 5 mM NaCl, pH 8.0) containing proteinase K and 1% SDS and incubated at 55° C. overnight. Following incubation, the resulting mixture was extracted with one volume of phenol:$CHCl_3$:isoamyl alcohol (25:24:1) via inversion for 10 minutes. The mixture was centrifuged at 12,000 RPM for 10 minutes and the aqueous layer was removed and subjected to extraction once more with one volume of $CHCl_3$:isoamyl alcohol (24:1) and separated via centrifugation. To precipitate the extracted DNA, one volume of isopropanol was added to the removed aqueous layer and the mixture was inverted for 15 minutes. The DNA was pelleted via centrifugation at 12,000 RPM for 15 minutes. The DNA pellet was then washed with 75% ethanol and air dried. Once nearly dry, TE buffer (pH 8.0) was added to the pellet and was resolved at 55° C. overnight.

TA cloning and Sanger sequencing. The bands of interest were gel-purified and directly cloned into the pCRII T-A vector (Invitrogen), and the nucleotide sequence of individual clones was determined by sequencing at Genewiz using universal T7 and/or SP6 primers.

Immunocytochemistry and immunohistochemistry.: Cells were fixed with 4% paraformaldehyde followed by standard immunocytochemistry with a monoclonal anti-HA antibody (1:200, Proteintech, Cat #66006-1-Ig). The ratio of saCas9-HA positive cells over Hoechst-positive nuclei was quantified in 6 random fields per well for 3 wells. For immunohistochemistry, the snap-frozen tissues/organs underwent cryostatic sectioning at 10 μm and fixed with 4% paraformaldehyde for 10 minutes. After washing, permeation with 0.5% Triton X-100 and blocking with 10% normal donkey serum, the sections were incubated with rabbit anti-HA polyclonal antibody (1:100, Proteintech, Cat #51064-2-AP) in PBS with 0.1% Triton X-100 overnight at 4° C. After washing three times each for 10 min, the sections were incubated with corresponding ALEXA FLUOR® conjugated donkey secondary antibody (1:500; Invitrogen, Grand Island, NY) and Phalloidin (100 nM; Cat. #PHDR1 cytoskeleton, Inc.) for 1 h at room temperature. Hoechst 33258 was used for nuclear counterstaining.

Statistical analysis. The quantitative data represented mean±standard deviation (SD) from 2-4 independent experiments, and were evaluated by Student's t-test. A p value that is <0.05 or 0.01 was considered as a statistically significant differences. For BLI data in EcoHIV infection mouse model, the student's t-test and linear-mixed effect models were used to compare total photon flux change over time between saCas9+EcoHIV vs EcoHIV only, which was measured by BLI from both dorsal and ventral side, respectively.

Results

The saCas9 sgRNA system efficiently excises HIV-1 proviral DNA. To determine the efficiency of the saCas9 system, three sgRNAs targeting HIV-1 LTR (FIG. 4A) were selected using the optimal PAM NNGRRN. The EcoHIV-eLuc reporter assay and Direct-PCR genotyping were performed as described (Yin, C. et al. *AIDS*, doi:10.1097/QAD.0000000000001079 (2016)). The sgRNA pairing method was employed because it is more reliable to identify successful excision of HIV-1 by functional reporter assay and PCR genotyping. As shown in FIG. 4B, all combinations between the selected three LTR sgRNAs in the presence of saCas9 almost completely eliminated the EcoHIV-eLuc activity (by 95-99%). Since the saCas9 PAM for these designed sgRNAs utilizes the same PAM (NGG) as spCas9 system, these seed sequences were cloned into a lentiviral (LV)-WG vector (Yin, C. et al. Functional screening of guide RNAs targeting the regulatory and structural HIV-1 viral genome for a cure of AIDS. AIDS, doi:10.1097/QAD.0000000000001079 (2016)) which harbors crRNA-loop-tracRNA (=sgRNA) sequence different from sequence of sgRNA for saCas9 (Ran, F A, et al. (2015). *Nature* 520: 186-191; Nishimasu, H, et al. (2015). *Cell* 162: 1113-1126) 2, 21, and compared the HIV-1 excision efficiency between saCas9/sgRNA and spCas9/sgRNA. Side-by-side transfection and EcoHIV-eLuc reporter studies showed that the spCas9 with these three pairing methods exhibited much less efficiency in reducing the luciferase activity (FIG. 4B). The outperformance of saCas9 over spCas9 is consistent with previous reports (Ran, F. A. et al. *Nature* 520, 186-191 (2015); Friedland, A. E. et al. *Genome Biol* 16, 257 (2015)). The higher efficiency of saCas9 compared to the spCas9 may be attributed to several factors: (1) The higher coexpression of sgRNA and saCas9 in the same cells because they are in a single vector; (2) Smaller size of saCas9 may have allowed for a higher gene delivery efficiency; and (3) The intrinsic nuclease of saCas9 may have better activity in making DSB (Ran, F. A. et al. *Nature* 520, 186-191 (2015); Nishimasu, H. et al. *Cell* 162, 1113-1126 (2015)). The effective eradication by the pairing of LTR sgRNA in both saCas9 and spCas9 was further validated by the PCR genotyping and Sanger sequencing (FIG. 4C).

Figure 4D:
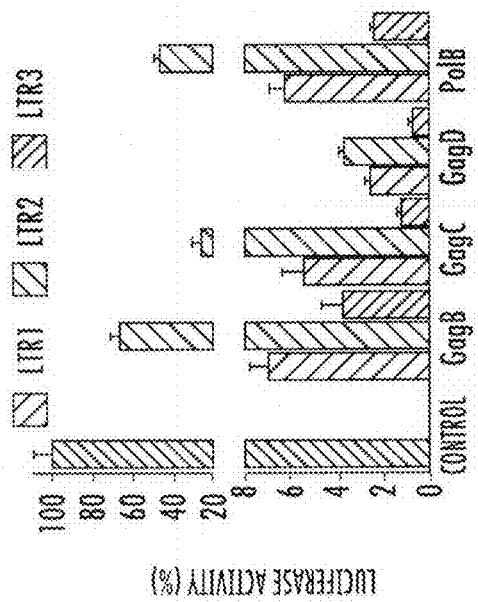
Figure 4E:
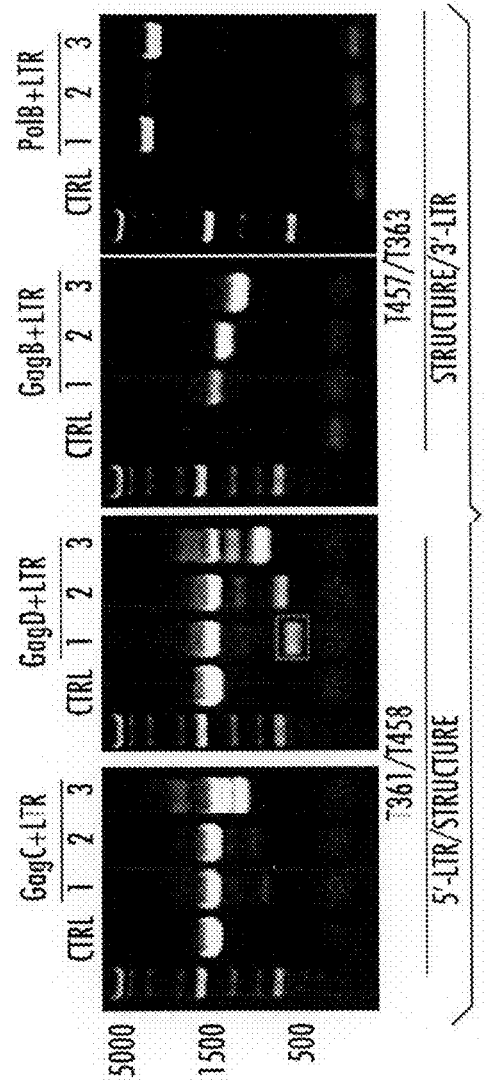
Figure 11A:
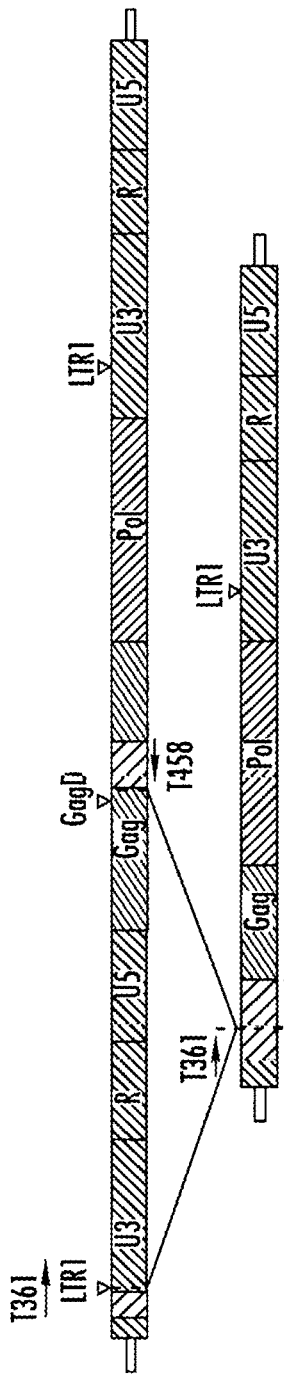
FIGS. 11A-11C show the validation of the expected fragmental deletion of EcoHIV-eLuc genome using TA-cloning and Sanger sequencing analysis.
Figure 11B:
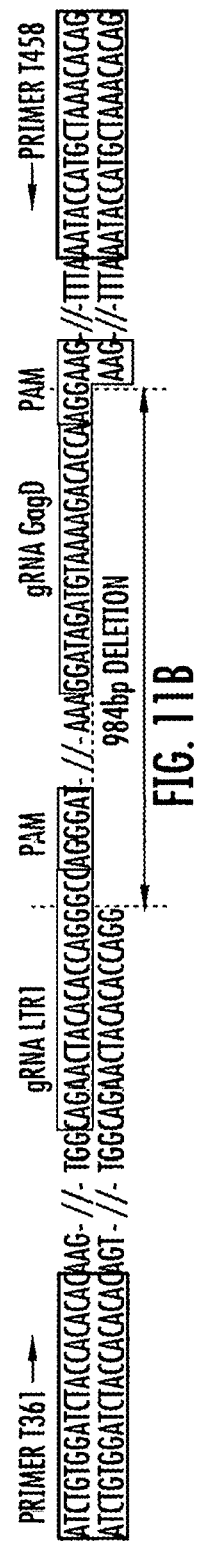
Figure 11C:
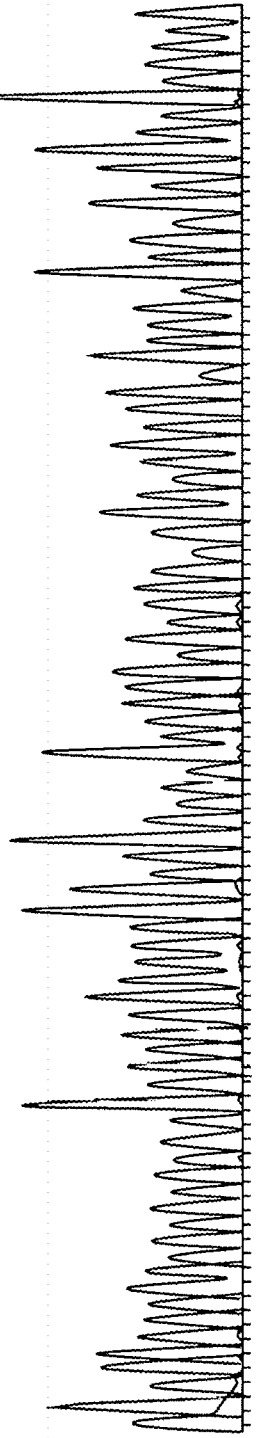

Combination of LTR sgRNAs with Gag or Pol sgRNA induced potent eradication. Using spCas9/sgRNA system, an easier PCR genotyping was demonstrated and a more efficient HIV-1 eradication through the LTR sgRNA pairing with viral structural genes, e.g. Gag, Pol. ((Yin, C. et al. AIDS, doi:10.1097/QAD.0000000000001079 (2016)). To test if this was also applicable to saCas9/sgRNA system, sgRNAs targeting Gag or Pol were paired with one of the three LTR sgRNAs. All combinations of LTR-1 or -3 with Gag or Pol sgRNA induced robust reduction in EcoHIV-eLuc activity in cell culture (FIG. 4D). The paring of LTR-2 and GagD also induced robust reduction but paring with GagB, GagC and PolB exhibited a lower efficiency in reducing the reporter activity (FIG. 4D). Direct-PCR genotyping with 5'-LTR or 3'-LTR pairs of primers validated the cleaving efficiency of all the sgRNA combinations (FIG. 4E). To further validate the fragmental deletion and provide a rational for quadruplex sgRNA (see below), combinations of LTR-1 and GagD were selected as representatives for TA-cloning and Sanger sequencing. The results showed the expected sequence of the fragments after two target site cleavages (FIGS. 11A-11C). These data evidence that all the sgRNAs selected for the saCas9 system are highly efficient in making DSBs at their predicted target sites and that paring of LTR sgRNAs with sgRNAs targeting viral structural regions induced various degrees of functional excision.

Multiplex sgRNAs in all-in-one AAV vector induced more potent eradication. For the pairing of two sgRNAs as described above, the two individual plasmids may not be delivered into the same cells during co-transfection. To ensure the maximal efficiency of HIV-1 eradication and suppression, the pair of LTR-1 and GagD were selected and the efficiency of reporter reduction was compared between co-transfection of two single sgRNA expressing vectors vs. transfection of one duplex sgRNA-expressing vector. The smaller size of saCas9 (3.159 kb) allows a single AAV vector to harbor two sgRNA-expressing cassettes and saCas9-expressing cassette for efficient AAV packaging and gene delivery (Friedland, A. E. et al. *Genome Biol* 16, 257 (2015)). As shown in FIG. 5A, transfection of the duplex sgRNA/saCas9 vector induced further reduction of luciferase reporter activity as compared with the co-transfection of two separate single sgRNA/saCas9 vectors. The cleavage of the reporter DNA was confirmed by PCR genotyping and the ratio of the cleaved fragmental band over the wild-type band exhibited stronger cleaving capability of duplex sgRNA/saCas9 vector than the two separate sgRNA/saCas9 vectors (FIG. 5B). The outperforming effect of the duplex sgRNA/saCas9 may result most likely from the co-expression of these three components in the same cells.

As demonstrated above, two LTR sgRNAs are capable of excising the entire HIV-1 genome in addition to the fragmental deletion of both LTRs, and a combination of LTR sgRNA with sgRNA targeting structural genes resulted in higher proviral cleavage efficiency and easier PCR genotyping. To combine these two features for the eradication efficiency optimization, a combination of LTR-1, LTR-3, GagD and PolB sgRNAs were selected and their expression cassettes were cloned into an all-in-one saCas9 AAV vector using a novel interchangeable Infusion cloning strategy. By transient transfection with equal amount of duplex or quadruplex sgRNA/saCas9-expressing single plasmid, it was found that the quadruplex sgRNA/saCas9 μplasmid was more efficacious at reducing the EcoHIV-eLuc reporter activity (FIG. 5C). This was validated by the PCR genotyping, showing a stronger reduction of the wild-type band generated by PCR primers across the 5'-LTR and Gag (FIGS. 5D, 5E). The primers T361/T458 (FIG. 4A) detected a fragmental deletion between LTR-1 and GagD and additional insertion in both duplex and quadruplex groups, while another fragment deletion expected between LTR-3 and GagD was observed in quadruplex group (FIG. 5D). The primer pair T710/T458 detected the predicted fragment after ligation between 5'-LTR-3 and GagD sites (FIG. 5E). Further PCR genotyping analysis covering the Gag/Pol and 3'-LTR showed that the quadruplex had a stronger potential for cleaving the entire HIV-1 genome. The primer T758/T363 detected two deletions between GagD and 3'-LTR-1 or -3 (FIG. 5F) while T689/T363 detected two deletions between PolB and LTR-1 or -3 (FIG. 5G). The primer T689/T711 detected one deletion as predicted (FIG. 5H). Comparative analysis of the band intensity for the fragment deletions showed that LTR-1 and GagD were most effective while LTR-3 was less efficient in the quadruplex sgRNAs/saCas9 system (FIGS. 5D, 5F, 5G). These cleaving patterns evidence that the quadruplex cocktail strategy is the most effective at eradicating HIV-1 entire genome due to multiplex fragmental deletions and multiple InDel mutations around the target sequence.

Quadruplex sgRNAs saCas9 can be packaged in a single AAV-DJ vector for more effective genome editing. The successful packaging of monoplex and duplex sgRNA/saCas9 AAV vector has been reported recently (Friedland, A. E. et al. *Genome Biol* 16, 257 (2015)). The duplex sgRNA/saCas9-expressing cassette (4.969 kb) is close to the packaging limit of AAV viruses ((generally 5-5.2 kb) Wu, Z., et al. *Mol Ther* 18, 80-86 (2010)). However, genome sizes ranging from 5.2 to 8.9 kb has been reported for efficient AAV packaging and gene delivery both in vitro and in vivo in some transgenes (Allocca, M. et al. *J Clin Invest* 118, 1955-1964 (2008); Grieger, J. C. & Samulski, R. J. *J Virol* 79, 9933-9944 (2005); Wu, J. et al. *Hum Gene Ther* 18, 171-182 (2007)). It was tested whether the quadruplex sgRNA/saCas9-expression cassettes (5.716 kb) could be packaged efficiently into an AAV virus. The AAV-DJ serotype was selected because: (1) It combines the features of 8 native AAV serotypes (AAV-2, AAV-4, AAV-5, AAV-8, AAV-9, avian AAV, bovine AAV, and caprine AAV) and achieves better transduction efficiency and broader range of targeting cells/tissues (Grimm, D. et al. *J Virol* 82, 5887-5911 (2008)); (2) It is capable of escaping from antibody neutralization (Bartel, M., et al. *Front Microbiol* 2, 204 (2011)); and (3) It provides the highest transduction efficiency to the liver for Cas9/sgRNA-mediated HIV-1 eradication in vivo. The liver enrichment is integral for demonstrating the proof-of-concept that the HIV-1 provirus can be excised in vivo. For the duplex sgRNA/saCas9, the virus titer in HEK293T cells was achieved as expected with genomic titer at $4.15$-$4.3 \times 10^{13}$ genomic copy (GC)/ml (unpurified crude lysate) determined by PCR and the functional titer of $4.4$-$9.7 \times 10^{8}$ transduction unit (TU)/ml by immunocytochemistry with an anti-HA antibody that detects the HA-tagged saCas9 protein. For the quadruplex sgRNA/saCas9, a similar genomic titer of $4.2 \times 10^{13}$ GC/ml was successfully achieved with only 1.8-3.9 fold less functional titer of $2.5 \times 10^{8}$ TU/ml compared with duplex sgRNA/saCas9 (FIGS. 11A, 11B). These data evidence that the quadruplex sgRNA/saCas9 AAV with 5.7 kb genome that was generated can be successfully packaged into AAV-DJ virus that can efficiently infect mammalian cells with functional expression of the saCas9 protein.

Figures 12A, 12B:
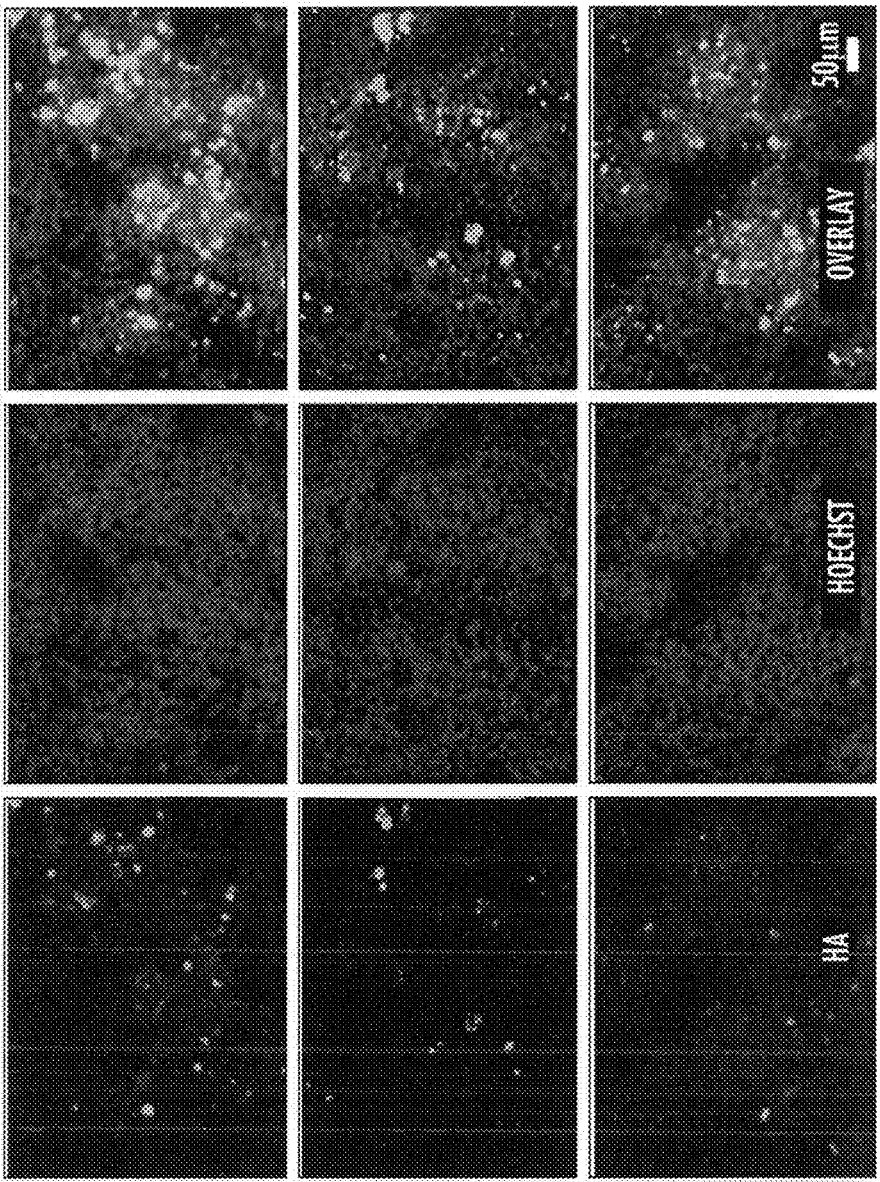
FIGS. 12A, 12B show the functional titer of AAV-DJ carrying multiplex sgRNAs and saCas9 in HEK293T cells.

AAV-Mediated Gene delivery of multiplex sgRNA saCas9 effectively eradicated HIV-1 proviral DNA in neural stem cells from HIV-1 Tg26 transgenic mice. The HIV-1 Tg26 transgenic mice was previously established to contain a loci integrated with more than 10 copies of the pNL4-3 proviral genome with a 3.1-kb deletion spanning the partial Gag and Pol genes to render the virus replication incompetent (Dickie, P. et al. *Virology* 185, 109-119 (1991)). The Tg26 mice develop a well-characterized kidney disease (Kopp, J. B. et al. *Proc Natl Acad Sci USA* 89, 1577-1581 (1992); Haque, S. et al. *Am J Pathol* 186, 347-358 (2016)), and potential un-characterized neurological and cardiovascular deficits (Cheung, J. Y. et al. *Clin Transl Sci* 8, 305-310 (2015)) and others. Before in vivo studies, the HIV-1 excision efficiency of multiplex sgRNAs/saCas9 was evaluated using neural stem/progenitor cells (NSCs/NPCs) isolated from Tg26 transgenic mice. The rationale to use NSCs/NPCs was the accumulating evidence for HIV infection/latency in NSCs/NPCs, which may relate to HIV-Associated Neurocognitive Disorders (HAND). Immunocytochemistry with an anti-HA antibody in mouse NSCs/NPCs after sgRNAs/saCas9 AAV-DJ infection showed that the monoplex sgRNA/saCas9 AAV-DJ infected 92.3% cells determined at 20 d post-inoculation with 10 functional MOI (fMOI), which equals to $1.8 \times 10^{5}$ gMOI, evidencing that the AAV-DJ virus is highly effective at infecting NSCs/NPCs. Equal fMOI of duplex (=$6.5 \times 10^{5}$ gMOI) or quadruplex (=$2.1 \times 10^{6}$ gMOI) sgRNAs/saCas9 AAV-DJ (FIGS. 12A, 12B) produced similar infection efficiencies of around 87.63% and 90.52%, respectively (FIGS. 6A-6C). Afterwards, the efficiency of both duplex and quadruplex sgRNAs/saCas9 in cleaving the integrated HIV-1 proviral DNA in cultured NSCs/NPCs was determined. The dose-dependent delivery of saCas9 and sgRNAs was validated by PCR analysis at 2 days post AAV-DJ infection (FIGS. 6D, 6E). Then, the HIV-1 excision efficacy was evaluated by PCR genotyping. Both duplex and quadruplex sgRNAs/saCas9 induced a dose-dependent deletion of the predicted DNA fragments at 2 days after AAV infection, while quadruplex sgRNAs/saCas9 induced a higher cleaving efficiency when equal fMOI was used (FIG. 6F). The cleavage efficiency was dramatically increased at 20 days post infection (FIG. 6G) because of the long-term AAV transduction leading to sustained expression of saCas9/sgRNAs and the cumulative genome editing. Again, the quadruplex induced a higher efficiency of HIV-1 excision (FIG. 6G) despite the similar infection efficiency (FIGS. 6B, 6C). These data evidence that AAV-mediated multiplex sgRNAs/saCas9 can effectively excise the integrated HIV-1 proviral genome in cultured NSCs/NPCs from HIV-1 Tg26 transgenic mice and the over-sized quadruplex sgRNAs/saCas9 AAV-DJ retains high efficiency of gene transduction and functional genome editing.

Multiplex sgRNA saCas9 effectively eradicated HIV-1 proviral DNA in various tissues organs of HIV-1 Tg26 transgenic mice. To test if Cas9/sgRNA is capable of eradicating the integrated HIV-1 proviral DNA in vivo, an AAV-DJ serotype was selected because it is capable of infecting broad range of tissues with highest infectivity in liver (Grimm, D. et al. *J Virol* 82, 5887-5911 (2008); Mao, Y. et al. *BMC Biotechnol* 16, 1 (2016)). As shown in FIG. 13A, one single dose of AAV-DJ virus ($4.15$-$4.20 \times 10^{12}$ GC) via tail vein injection could efficiently deliver sgRNAs- and saCas9-expressing cDNA into the liver and spleen in the first week alone. Histopathological and immunohistochemical examination of liver did not identify any AAV-related tissue toxicity. The observed high transduction efficiency and minimal tissue toxicity is consistent with a previous report using similar dosages in adult mice. However, one additional injection of the same dose 1 week after the first injection did show consistent pattern of gene delivery (FIG. 13B). The AAV-DJ carrying duplex or quadruplex sgRNA along with saCas9 results similar efficiency of gene delivery in most organs (FIGS. 13A, 13B), even though the insert of quadruplex sgRNA/saCas9 appears to be beyond the limit of the AAV packaging capacity. To determine the efficacy of the sgRNA/saCas9 in cleaving the integrated HIV-1 genome in animal tissues/organs, PCR genotyping was performed with a pair of primers that can amplify the fragmental deletion and ascertain the eradication event as was demonstrated above. For the 5'-LTR/Gag deletion, fragmental deletions were not observed 1 week after infection even using nested PCR amplification, which is likely due to a low expression level of Cas9 in the first week after in vivo AAV delivery. However, after conducting the nested PCR analysis (FIG. 13C), the fragmental deletion to various extents was observed in most organs/tissues, particularly in liver, bone marrow, and spleen (FIG. 13D). Additional AAV infection at 7 d after the first infection increased the cleaving efficiency in most organs/tissues (FIG. 13D). The size of the fragmental deletion varied with tissues/organs, implying potential difference in DNA repairing events between tissues/organs.

These fragmental deletions were verified by T-A cloning of representative bands and Sanger sequencing (FIG. 13E). Again, both duplex and quadruplex sgRNA/saCas9 AAV-DJ induced similar pattern of fragmental deletion mainly in liver, while other organs showed variable pattern of fragmental deletions (FIG. 13D).

Figure 7A:
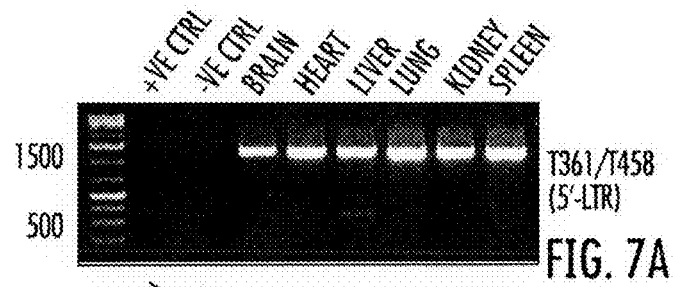
FIGS. 7A-7G show the quadruplex sgRNAs/saCas9 AAV-DJ/8 induced HIV-1 proviral DNA excision (FIGS. 7A-7C) and robust reduction in HIV-1 RNA transcription (d-g) in most organs/tissues of Tg26 transgenic mice.
Figure 7B:
Figure 7C:
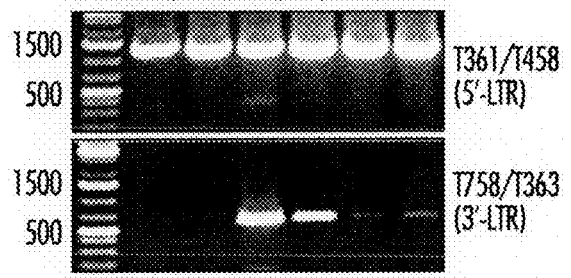
Figure 7D:
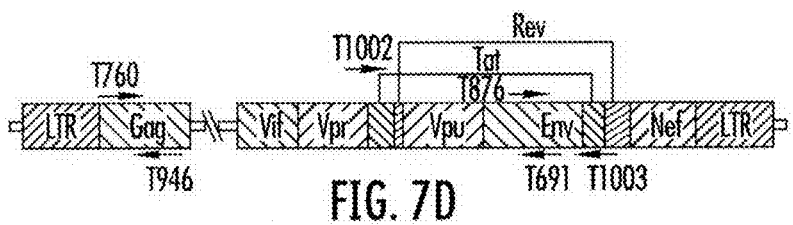
Figure 7E:
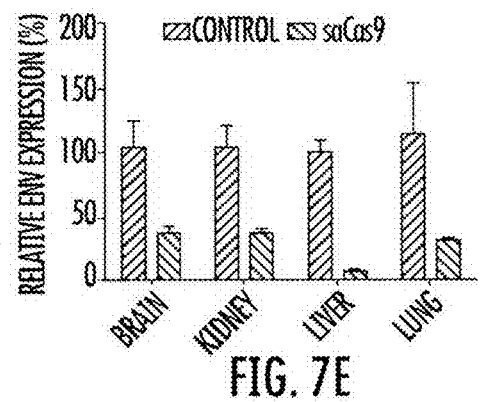
Figure 7F:
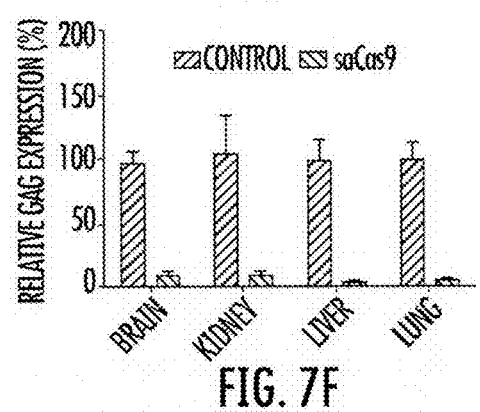
Figure 7G:
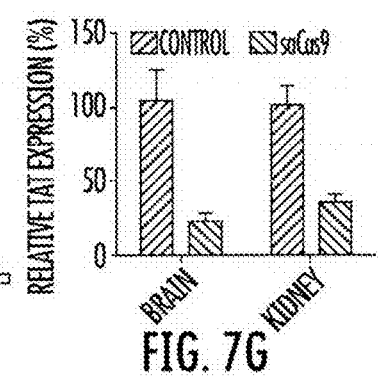
Figure 15A:
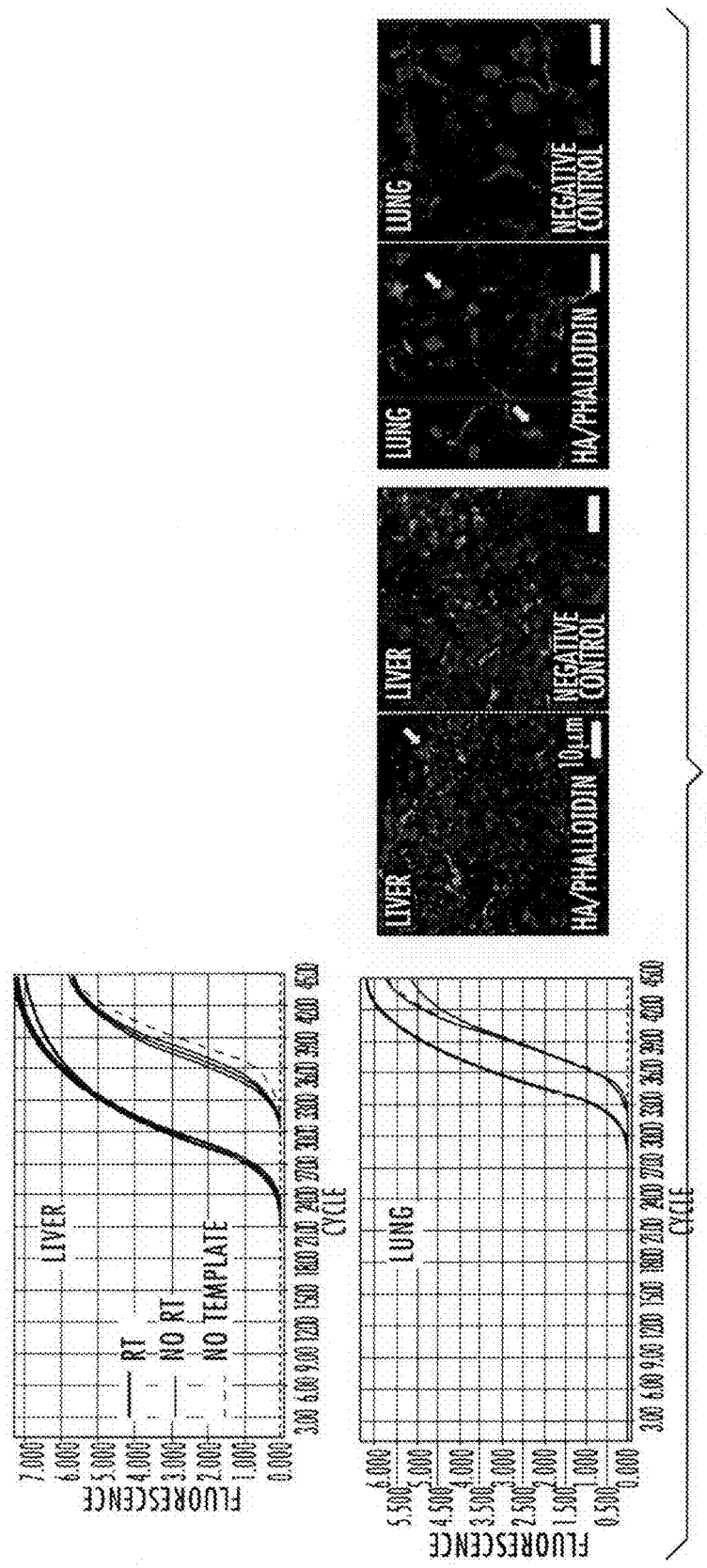
FIGS. 15A and 15B show the expression of saCas9 protein in the organs/tissues of Tg26 mice at 2 (FIG. 15A) and 4 (FIG. 15B) weeks after intravenous injection of quadruplex sgRNAs/saCas9 AAV-DJ/8. Total RNAs of the indicated organs/tissues were extracted with an RNeasy Mini kit and the residual genomic DNA was removed through an in-column DNase digestion with an RNase-Free DNase Set. Real-time PCR analysis of the cDNA reversely transcribed (RT) from total RNA was used to measure the expression of the transgene saCas9, which is mainly localized to the liver and lung. No RT was used as a negative control for genomic DNA contamination. No template was used as PCR control. Representative micrographs of the tissue frozen sections immunostained with rabbit anti-HA tag antibody (red) and treated with Phalloidin (green) showing the expression of saCas9 protein in liver and lung. Negative control only used secondary antibody. White arrows pointed the presence of saCas9-like immunoreactivity in nuclei. Scale bars=10 µm.
Figure 15B:
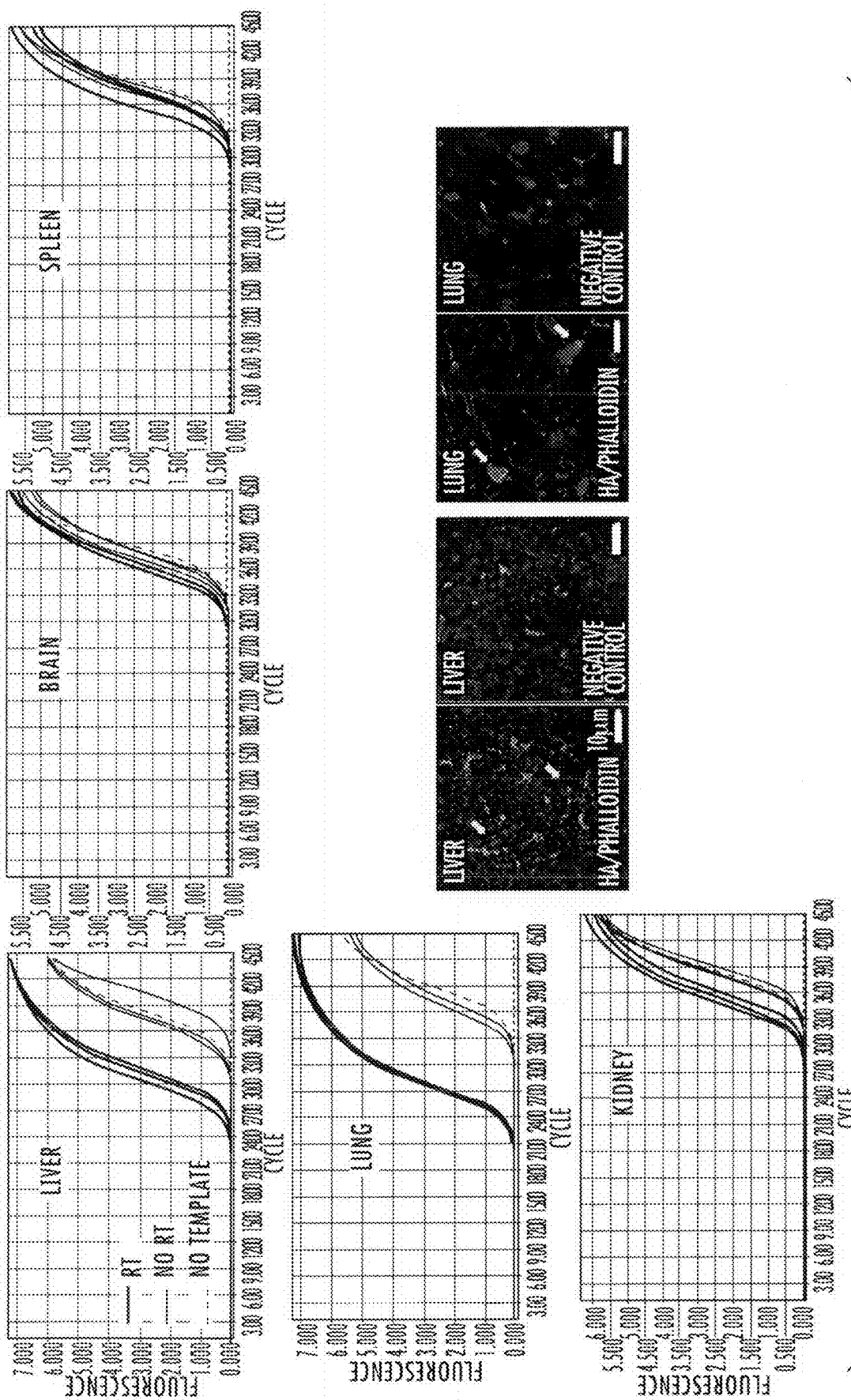
Figure 16A:
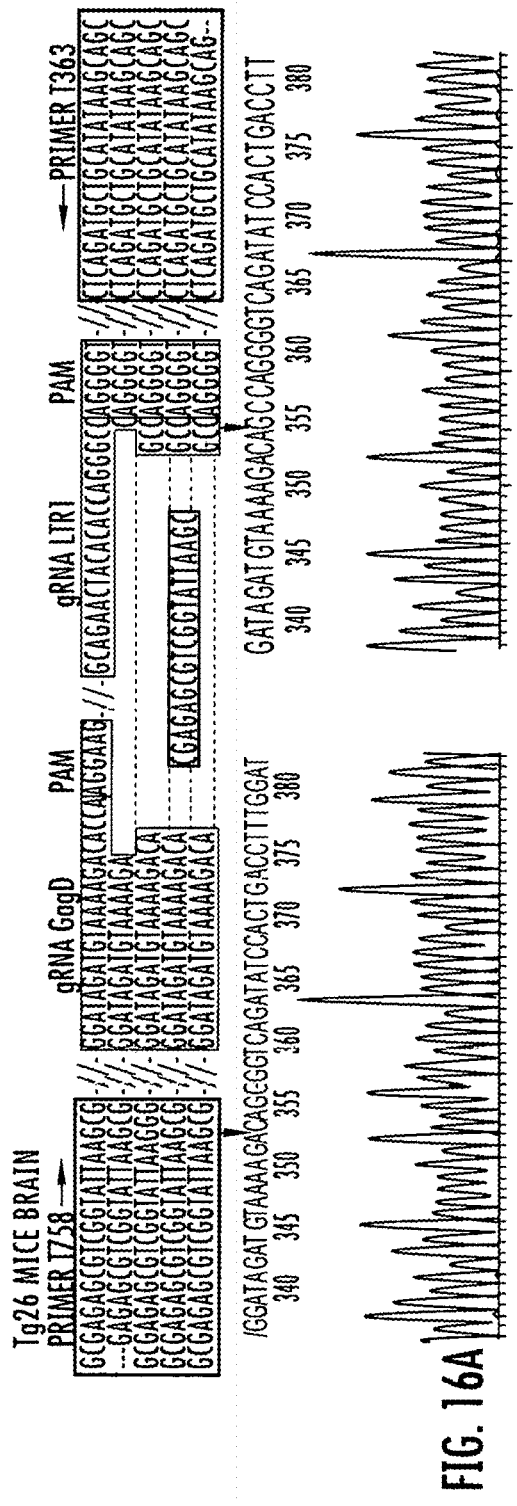
FIGS. 16A and 16B show the validation of the GagD to 3'-LTR1 fragmental deletion of HIV-1 genome in the brain (FIG. 16A) and liver (FIG. 16B) of Tg26 transgenic mice at 2 weeks after intravenous administration of the quadruplex sgRNAs/saCas9 AAV-DJ8. The predicted deletion of the 4992 bp fragment after cleavage at the third nucleotide from the PAM (highlighted red) was observed in most of the bacterial clones of PCR product in TA-cloning with a small insertion or deletion in a few clones. Representative Sanger sequence tracing was presented to show the cleaving/re-ligation site (red arrows) between GagD and 3'-LTR1.
Figure 16B:
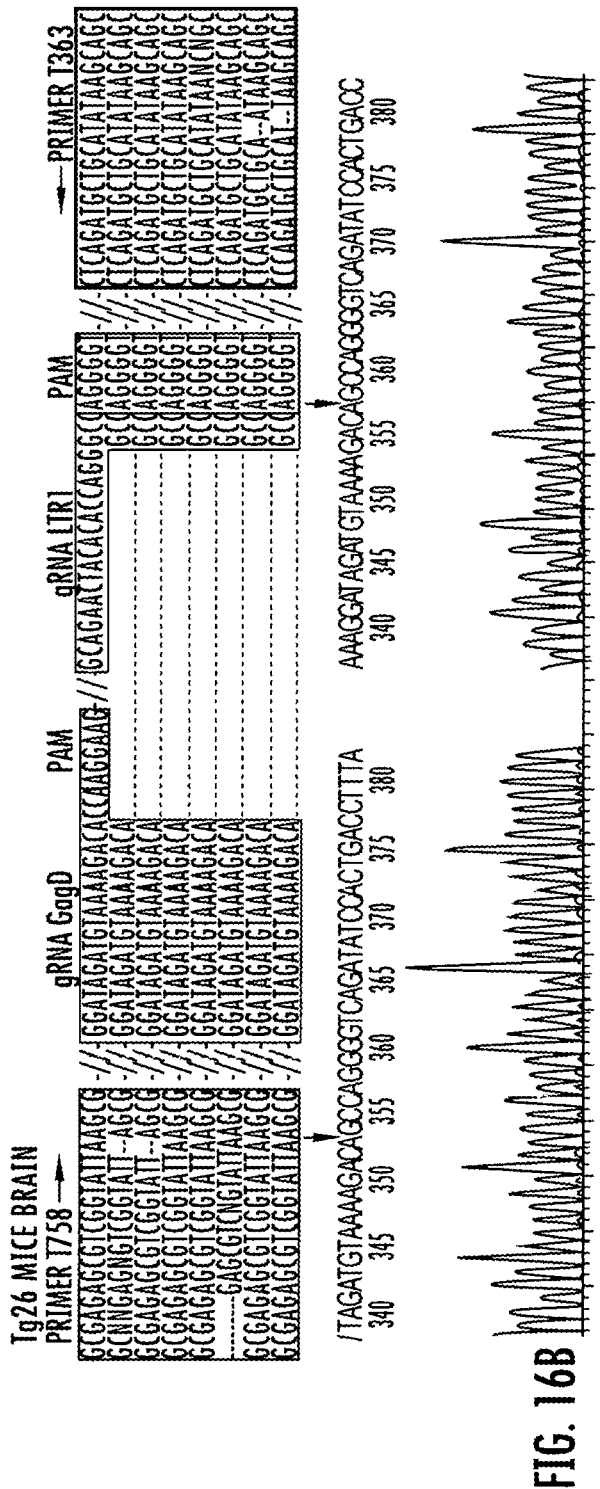

To expand the tissue ranges and potential cell types of HIV-1 eradication in Tg26 transgenic mice, the quadruplex sgRNAs/saCas9 all-in-one vector was packaged into AAV-DJ/8 viruses. To maximize in vivo transduction efficiency, the AAV-DJ/8 virus was purified and concentrated using large scale of preparation (Holehonnur, R. et al. (2014). *BMC Neurosci* 15: 28). The packaging efficiency for the over-sized quadruplex sgRNAs/saCas9 reached $3.07 \times 10^{14}$ GC/ml, which was close to the titer ($4.21 \times 10^{14}$ GC/ml) of the side-by-side packaging for a control AAV-Cre-rLuc vector that carries 3 kb of insert which was prepared at the same time. One single tail i.v. injection of the purified quadruplex sgRNA/saCas9 AAV-DJ/8 ($1.5 \times 10^{12}$ GC) induced efficient transduction of saCas9 gene in most organs/tissues collected (FIG. 14A). The expression of saCas9 mRNA and protein in transduced organs/tissues was validated by RT-qPCR with primers targeting saCas9 and immunohistochemistry with an anti-HA antibody. (FIG. 15A) For the 5'-LTR/Gag primer pair, visible fragmental deletions of the designed size were observed using conventional PCR conditions (FIG. 7A). Using the Gag/3'-LTR primer pair, the fragmental deletion in liver, lung and brain tissues was observed under the conventional PCR condition (FIG. 7B). TA cloning and Sanger sequencing validated the fragmental deletion of the designed size in both brain and liver (FIGS. 16A, 16B). One additional infection ($1.5 \times 10^{12}$ GC) 2 weeks after the first injection expanded the range of transduced tissues/organs and increased the gene transduction efficiency of saCas9 and sgRNAs 4 weeks after the first injection (FIGS. 14B, 15B). The excision efficiency as shown by the fragmental deletion with the Gag/3'-LTR primer pair was also increased in liver and lung and expanded to other organs such as kidney and spleen (FIG. 7C). RT-qPCR analysis revealed a significant reduction in the mRNA expression of structural viral proteins Gag and Env in the brain, kidney, liver and lung (FIGS. 7D-7F) as well as the regulatory protein Tat in brain and kidney (FIGS. 7G, 14C). Taken together, both AAV-DJ and AAV-DJ/8 viruses harboring either duplex or quadruplex sgRNA/saCas9 induced sufficient gene delivery infection in vivo and subsequent eradication of integrated HIV-1 genome in various organs/tissues of Tg26 transgenic mice.

Whole genome sequencing and off-target analysis (Ebina, H. et al., (2013). *Scientific reports* 3: 2510; Kaminski, R, et al. (2016). *Sci Rep* 6: 22555; Yin, C, et al. (2016). *AIDS* 30: 1163-1174) did not detect any apparent off-target effects of spCas9 with multiplex sgRNAs in cultured primary cells or cell lines. To examine any potential in vivo off-target effects in this study, a T7E1 assay was performed using genomic DNA from the tissues/organs of Tg26 mice treated with quadruplex sgRNAs/saCas9. Based on potential off-target sites predicted by bioinformatics analysis, 2-3 predicted sites were selected for each sgRNA target (LTR-1, LTR-3 and GagD) with highest score of specificity and performed high-fidelity PCR generating 500-800 bp product for T7E1 evaluation. As shown in FIGS. 17A-17F, no mutations were found in 7 predicted off-target sites within the mouse genome but a clear mutation was detected in the on-target PCR product.

Figure 8A:
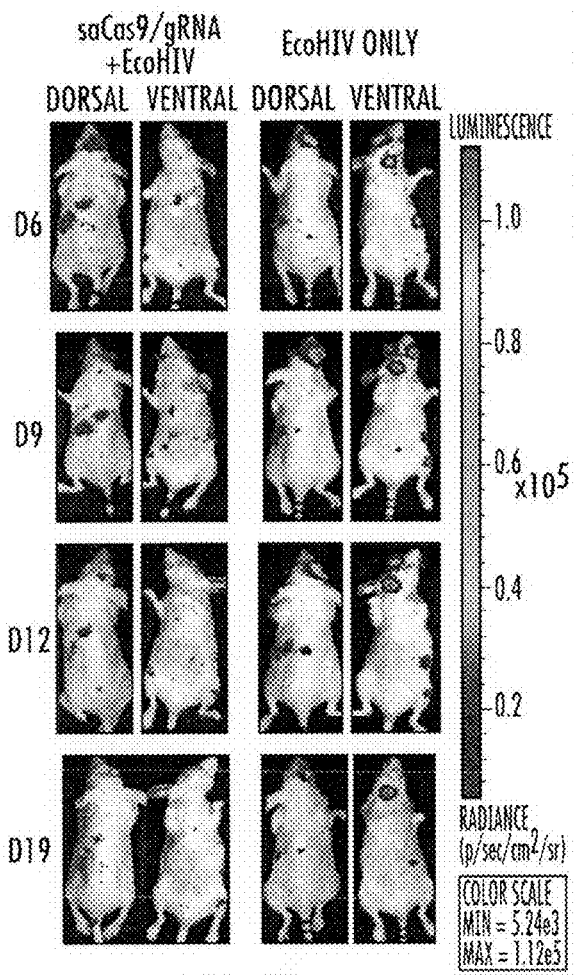
FIGS. 8A-8D is a bioluminescence imaging analysis showing that quadruplex sgRNAs/saCas9 AAV-DJ/8 induced excision of EcoHIV-eLuc in vivo.
Figure 8B:
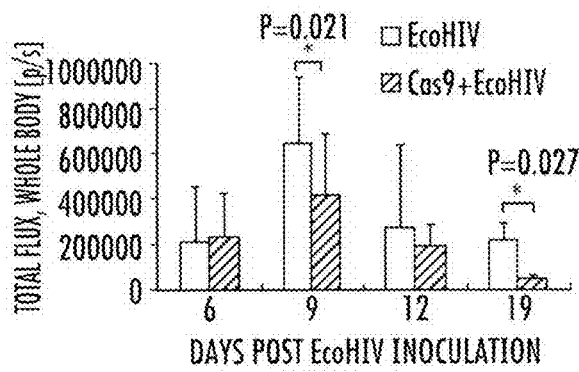
Figure 8C:
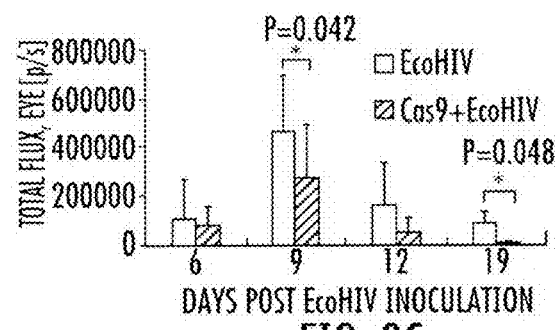
Figure 8D:
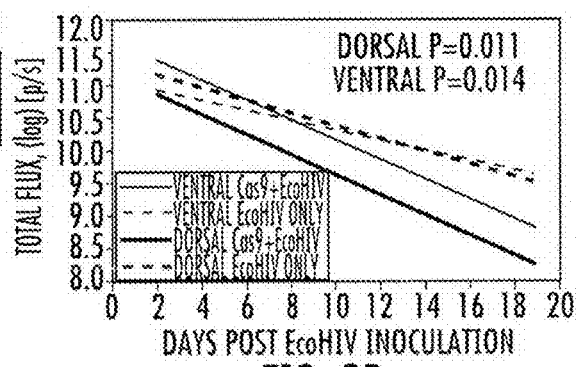

In vivo HIV-1 excision is visualized in an experimental mouse model inoculated with cell-free EcoHIV-eLuc reporter virus. As shown above in Tg26 mice, the quadruplex sgRNA cocktail can be efficiently packaged into an AAV virus and effectively excise the entire HIV-1 proviral DNA from the host genome both in vitro and in vivo. These results prompted the further testing for the feasibility and efficiency of systemic HIV infection via the AAV-sgRNA/saCas9 approach. However, this does not recapitulate the clinical HIV infection/latency in terms of HIV-1 proviral copies/loci, random integration, rare infected cell types and high rate mutation. To further test the feasibility and efficiency of HIV-1 excision after systemic HIV-1 infection via the AAV-sgRNA/saCas9 approach, an EcoHIV-eLuc reporter virus was utilized to infect conventional NCr strain of nude mouse model (Potash, M. J. et al. *Proc Natl Acad Sci USA* 102, 3760-3765 (2005); Kelschenbach, J. L. et al. *J Neuroimmune Pharmacol* 7, 380-387 (2012)). Right after EcoHIV-eLuc inoculation (total 250 ng of HIV p24/mouse, n=3) via retro orbital injection in the right eye, a single dose of AAV-DJ/8 ($3.07 \times 10^{12}$ GC/mouse) was injected into each mouse (n=3) via the same injection route immediately after EcoHIV inoculation. Another three NCr mice were injected with only EcoHIV-eLuc of the same dosage as a negative control group. A longitudinal bioluminescence imaging (BLI) of live animals was performed over 19 days after EcoHIV-eLuc inoculation starting on Day 6 post inoculation. (FIGS. 8A-8D). A significant reduction of EcoHIV-eLuc reporter activity was observed in the neck lymph nodes and the surrounding tissues of the right eye where the injection was taken place, as compared to the control group (n=3) without AAVDJ/8 infection (FIG. 8A). The reduction of EcoHIV-infected cell population in saCas9-treated mice is statistically significant (p<0.05) on both Days 9 and 19 via in vivo measurement of the imaging signal from the entire mouse or the right eye area (FIGS. 8B and 8C). Using a linear mixed-effects model for statistical significance, the efficacy of saCas9/gRNA treatment over the entire 19 days on HIV-1 excision was compared. Comparing with the negative control group, the reduction of EcoHIV-eLuc infection by AAV-sgRNAs/saCas9 treatment is statistically significant as measured by the bioluminescence output from the neck lymph node at the dorsal (p<0.011) and ventral side (p<0.014) during the entire course of the experiment (FIG. 8D).

Figure 19:
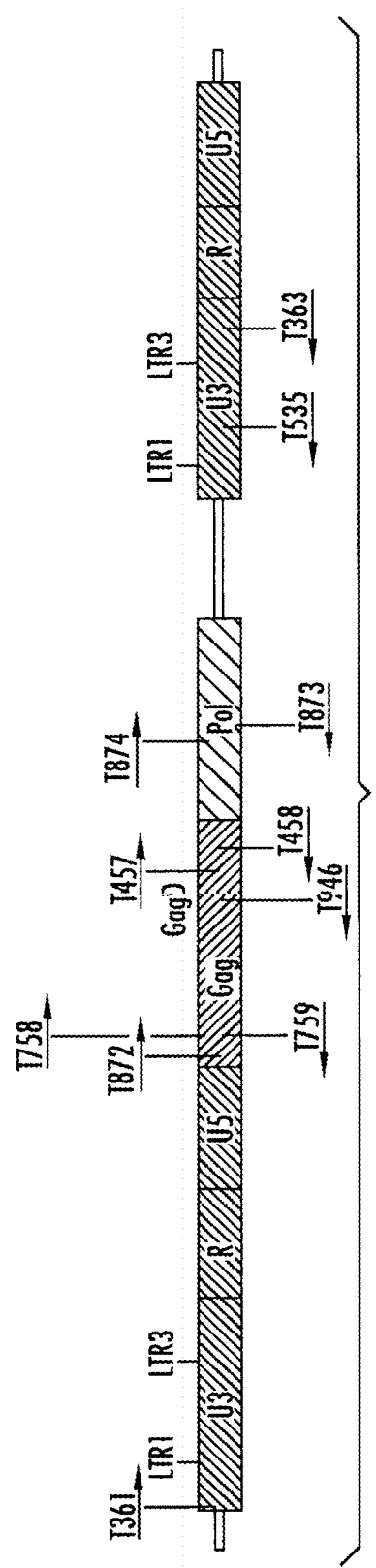
FIG. 19 shows a strategy of qPCR for detecting HIV excision efficiency. The table showing all qPCR primer pairs for indicating uncut, cut and internal EcoHIV DNA level, and the diagram showing all primers' location.

To validate the in vivo eradication efficiency, PCR genotyping was performed using the established PCR condition as aforementioned at the endpoint of experiments (19 days post AAV transduction of SaCas9/gRNA). The efficient transduction of saCas9, GagD and LTR1 transgenes by AAVDJ/8 was validated mainly in the liver, with slightly varied distributions in other organs and tissues (FIGS. 9A-9C). Using conventional PCR, an efficient and robust excision of the predicted fragment was observed in most tissues/organs with the highest efficacy in the injected right eye area, the heart, blood, liver, spleen and lymph node (FIGS. 9D-9F). The variability in edited tissues from different animals may result from the random cellular/tissue distribution of ecoHIV-eLuc infection, AAV-mediated gene delivery and Cas9-mediated excision. Again, some the fragmental deletions were validated by TA-cloning and Sanger sequencing (FIGS. 18A-18C). To quantify the excision efficiency of quadruplex sgRNAs/saCas9 in vivo, qPCR analysis of the excised fragments was performed using three different primer combinations (FIG. 19). The melting peak curve analysis clearly identified three types of proviral DNA excisions as designed: 5'-LTR1 to GagD, and GagD to 3'-LTR1 or 3'-LTR3. Using the uncut (non-targeting) region (flanking both target sites) as internal normalization, the excision efficiency was assessed in selected tissues/organs (FIGS. 9G-9I), although the individual number may underestimate the efficiency due to various combinations of excision. The results showed that the excision efficiency (FIGS. 9G-9I) was consistent with PCR genotyping (FIGS. 9D-9F). The excision types and efficiency varied with different organs/tissues (FIGS. 9G-9I). Interestingly, all three types of excision occurred with 96% efficiency for the GagD/3'-LTR in B1M3 mouse's liver (FIG. 9I). These data evidence that the quadruplex sgRNAs/saCas9 AAV-DJ/8 is highly effective at excising the HIV proviral genome even in newly infected cells during in vivo systematic HIV infection.

Figures 20A, 20B:
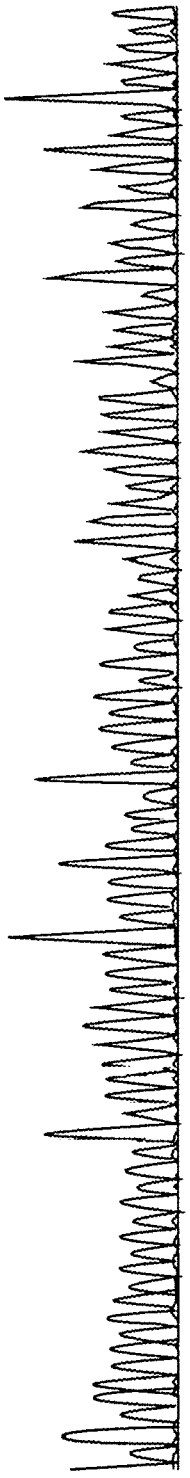
FIGS. 20A, 20B shows the validation of the fragmental deletion of HIV-1 proviral DNA between 5'-LTR1 and GagD sites in organs/tissues of humanized BLT mice after saCas9/sgRNA genome editing.
Figures 21A, 21B:
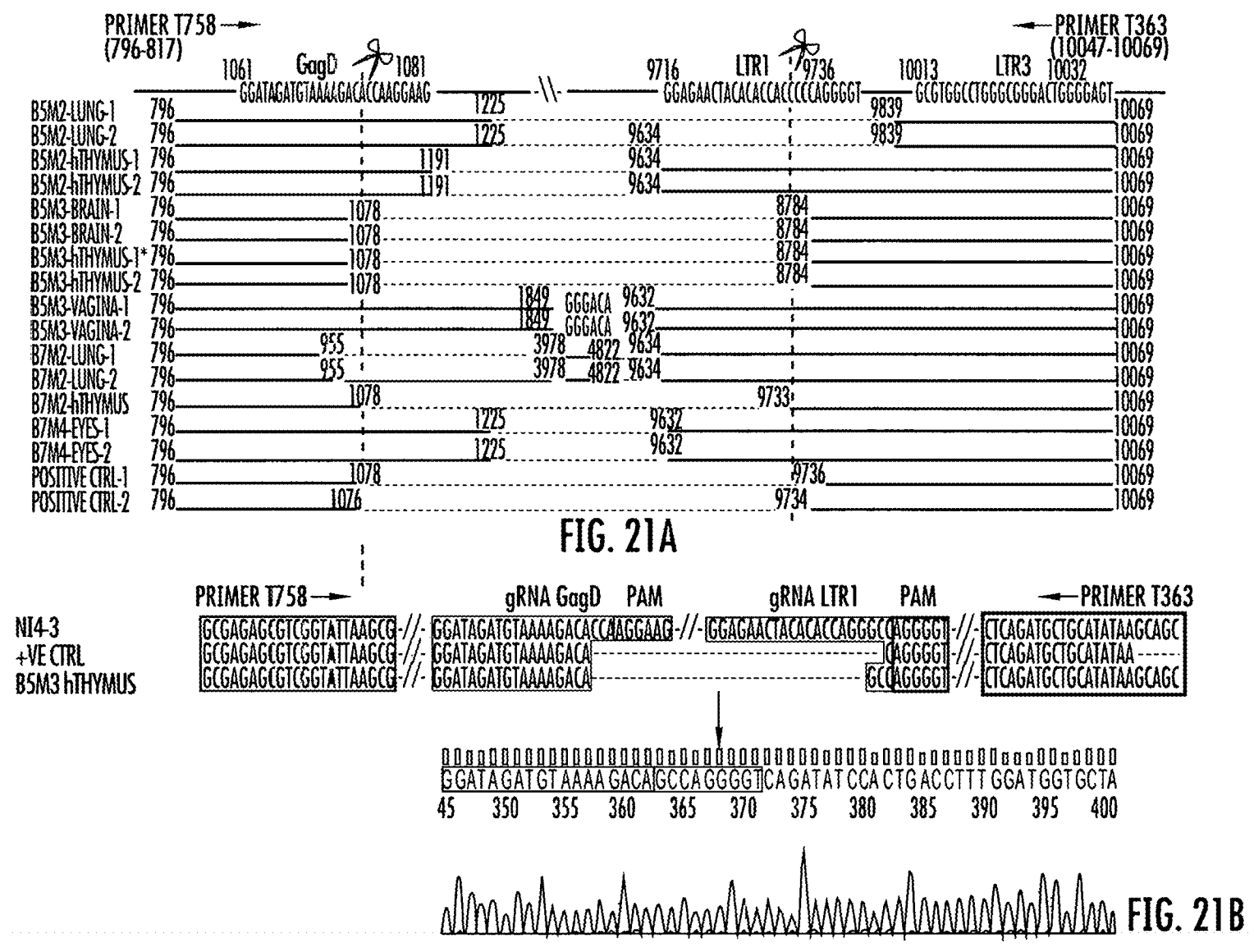

In vivo excision of HIV-1 provirus from latently-infected human cells is detected in humanized BLT mice. To demonstrate the feasibility of saCas9/sgRNA genome editing on excising HIV-1 provirus in a more clinically relevant animal model, AAV-DJ/8 carrying sgRNAs/saCas9 was administered to humanized BLT mice inoculated with a R5-, M-tropic $HIV_{NL-BaL}$-eLuc reporter virus via vaginal mucosal transmission (n=3, mouse ID=B5M2, B5M3 and B6M3) or intraperitoneal injection (n=3, mouse ID=B7M2, B7M4 and B10M4). The spatiotemporal dynamics of HIV-1 dissemination in these BLT mice were visualized and analyzed longitudinally via whole body BLI with a sensitivity of visualizing 5 single cells in a niche (Song, J, et al. (2015). *J Gen Virol* 96: 3131-3142). These BLT mice showed certain degree of either local or systemic HIV dissemination, but the infection diminished and completely ceased after the first 60 days without any visible infection determined by whole body BLI examination in the following 70 days or longer. This phenomenon could possibly be attributed to T cell depletion, HIV-1 latency or the possible silencing of eLuc reporter by mutations during HIV-1 replication. Since no HIV-1 genome was detected by nested PCR in some of the tissues (FIGS. 7A-7F), the contribution of mutation to the silenced reporter expression is less likely. The quadruplex sgRNAs/saCas9 AAV-DJ8 was administered via both intravenous and intravaginal routes into HIV-infected BLT mice, B5M2 and B5M3. Along with the negative control mouse B6M3, B5M2 and B5M3 were inoculated with HIV-1 via vaginal mucosa, or only intravenous injection of AAV-DJ8 into the HIV-infected BLT mice, B7M2 and B7M4. Along with the negative control mouse B10M4, B7M2 and B7M4 were inoculated with HIV-1 via intraperitoneal injection. At 2-4 weeks after AAV delivery, BLT mice were sacrificed and genomic DNA samples were extracted from major organs/tissues for PCR genotyping as described above. The presence of HIV-1 proviral DNA in the harvested organs/tissues was validated with nested PCR using the 5'-LTR/Gag primer pairs (T361/T458 then T361/T946) (FIGS. 7A-7F). Importantly, the fragmental deletion was observed with both 5'-LTR/Gag primer pair T361/T946 and Gag/3'-LTR primer pair T758/T363 (FIGS. 7A, 7B, 7D, 7E) in vagina, heart, lung, right eye (AAV injection site), colon, and the human thymic organoid under the left kidney capsule. In particular, much higher intensity of the band representing a fragmental deletion was observed over the one for the intact proviral DNA in the same tissue, e.g. the heart and vaginal tract of B5M3 mouse (FIG. 7B). This result clearly evidences an efficient excision of HIV-1 proviral DNA in latently infected human cells within a solid tissue via a single i.v. injection of quadruplex sgRNAs/saCas9 AAV-DJ/8. TA-cloning of these PCR products and Sanger sequencing validated the fragmental deletions (FIGS. 20A, 20B) for PCR products from 5'-nested PCR using primer pair T361/T946; FIGS. 21A and 21B for PCR products from 3'-nested PCR using primer pair T758/T363). Within the cleaved residual sequence at both 5'-LTR/Gag region (FIGS. 20A, 20B) and Gag/3'-LTR region (FIGS. 21A, 21B), various degrees of insertion or deletion were observed between the predicted cleaving sites at the third nucleotide from PAM of the targeting sgRNAs (FIGS. 20A, 21A). These sets of pre-clinical data demonstrate the proof-of-principle that quadruplex sgRNAs/saCas9 can be delivered by AAV-DJ8 into the resident HIV-1 latently infected human cells in major tissues and organs in a humanized mouse model to excise the integrated HIV-1 proviral DNA.

DISCUSSION

The salient finding in this study is the effective eradication of HIV-1 proviral DNA from the host genome in animal models using saCas9 and multiplex sgRNAs delivered by an all-in-one AAV-DJ or AAV-DJ/8 vector. These viruses induced effective gene delivery and HIV-1 proviral eradication both in vitro and in vivo in HIV-1 Tg26 transgenic mice and EcoHIV-eLuc acutely infected mice. Based on the clinical application of AAVs in gene therapy, this study provides a novel therapeutic to treat HIV-1/AIDS patients. Furthermore, the easy multiplex sgRNA cloning, rapid reporter screening, reliable Direct-PCR genotyping and high efficient AAV virus production provide a clinical application of saCas9/sgRNAs genome editing in personalized and precision medicine. Using multiplex sgRNAs to target multiple HIV proviral DNA simultaneously is beneficial to prevent the escape of HIV from high mutation rate during HIV-1 replication because the probability of double mutations in two different target sequence in the same HIV proviral genome is relatively low. Finally, it was demonstrated that quadruplex sgRNA/saCas9 strategy combining two LTR targeting sites (at both 5'- and 3'-ends) with two structural targeting sites (conserved in Gag and Pol) is a promising therapeutic candidate for HIV-1 eradication in personalized medicine due to maximizing the possibility of multiple InDel mutations and fragmental deletions among the entire HIV-1 genome despite of the high mutation rate in the clinical patients with HIV-1 infection. This quadruplex strategy also provides additional advantages: (a) largely reducing the potential of HIV-1 escape, (b) high possibility of HIV-1 excision despite of the continuous proviral mutation in the clinical HIV-1 patient population, (c) reliable loss-of-function achievement due to removing of a substantial portion of target gene or genome and (d) optimal efficiency of excision.

The genome editing efficiency in vivo and its clinical applications rely mainly on the effective gene delivery. For basic researches, transfection of regular plasmids and transduction of various viral vectors (specifically lentiviral, adenoviral and AAV vectors) have been widely used to deliver Cas9 and sgRNA separately or in a combination. Due to high transduction efficiency in most target cells, and long-term but reversible/inducible gene expression, lentivirus-mediated Cas9/gRNA delivery has been preferentially and extensively employed in most labs. However, the safety and immunogenicity of lentiviruses and adenoviruses are limiting their clinical feasibilities. The integrase-deficient lentivirus (IDLV) has been tested for ZFN delivery (Cecilia, A. P. et al. *Current Gene Therapy* 14, 365-376 (2014); Pelascini, L. P. et al. *Human Gene Therapy Methods* 24, 399-411 (2013); Lombardo, A. et al. *Nat Biotechnol* 25, 1298-1306 (2007)), and its application for Cas9 and TALEN delivery remains in question (Wang, X. et al. *Nat Biotechnol* 33, 175-178 (2015)). AAV-mediated gene therapy is becoming a very promising approach in clinical trial because of no mutagenesis, weak toxicity, low host immune response, and long-term efficacy (Hastie, E. & Samulski, R. J. *Hum Gene Ther* 26, 257-265 (2015); Mingozzi, F. & High, K. A. *Blood* 122, 23-36 (2013)). Several studies have tested the feasibility and efficiency of AAV-mediated Cas9 delivery both in vitro and in vivo. The widely-used spCas9(1368 aa) is 4.1 kb in size, leaving very small space for the cloning of AAV vector that can be efficiently packaged and effectively infect cells or tissues. Nevertheless, four labs using minimal promoter and poly-A sequence have reported the success in applying AAV-spCas9 in cultured cells and animal models (Swiech, L. et al. *Nat Biotechnol* 33, 102-106 (2015); Platt, R. J. et al. *Cell* 159, 440-455 (2014); Senis, E. et al. *Biotechnol J* 9, 1402-1412 (2014); Howes, R. & Schofield, C. *Methods Mol Biol* 1239, 75-103 (2015)). To improve the AAV delivery efficiency, splitting spCas9 into functional N-terminal and C-terminal parts has been reported recently (Wright, A. V. et al. *Proc Natl Acad Sci USA*, doi:10.1073/pnas.1501698112 (2015); Zetsche, B., et al. *Nat Biotechnol* 33, 139-142 (2015)), which provides a new way to deliver spCas9 more efficiently in preclinical animal models. The AAV-split-spCas9 nickase vector using the GyrA intein system has been also reported to increase the specificity of genome editing (Fine, E. J. et al. *Scientific reports* 5, 10777 (2015)). Several smaller Cas9 orthologs have been identified recently, among which, the saCas9 has been well characterized and exhibits highly promising for animal studies and clinical applications. These smaller Cas9s not only render AAV gene therapy feasible in clinical trial using all-in-one vector system but also increase the packaging and transduction efficiency in IDLV system that is also holding a wide attraction for clinical trial (Liu, K. C. et al. *Current gene therapy* 14, 352-364 (2014)). Several animal studies have demonstrated the high efficiency of AAV packaging and gene transduction using the saCas9 plus one or two sgRNA expressing cassettes in an all-in-one AAV vector. In this study, it was demonstrated that the duplex HIV-sgRNAs with saCas9 in all-in-one AAV-DJ vector is also capable of delivering transgenes and eradicating HIV-1 genome in cultured cells and particularly in various organs/tissues of Tg26 transgenic mice. Furthermore, it was demonstrated for the first time that the over-sized all-in-one AAV vector encoding quadruplex sgRNAs and saCas9 is similarly capable of achieving high titer packaging and inducing effective eradication of HIV-1 genome in cultured HIV-integrated NSCs/NPCs as well as in various organs/tissues of HIV-1 latent Tg26 transgenic mice and acutely-infected EcoHIV-eLuc mice. These novel and exciting findings pave a new way to develop a cocktail of multiplex sgRNAs targeting the HIV-1 LTR and structural protein regions for an optimal gene therapy in HIV-1 eradication in the preclinical and clinical settings.

Several approaches to place multiplex sgRNA-expressing cassettes in an all-in-one vector have been reported. Using the RNA processing property of the Csy4 protein or ribozymes, a single transcript under a Pol II promoter can be processed into multiple sgRNAs (Nissim, L., et al. *Mol Cell* 54, 698-710 (2014); Gao, Y. & Zhao, Y. *J Integr Plant Biol* 56, 343-349 (2014)). Multiplex vector with up to 7 sgRNAs under the same U6 promoter has been successfully constructed using the Golden Gate cloning method and its multiplex targeting efficiency has been tested for multiplex genome/epigenome editing, simultaneous activation/repression of multiple genes (Sakuma, T., et al. *Scientific reports* 4, 5400 (2014)). To reduce a potential risk of recombination due to repetitive DNA sequences and to maximize the expression efficiency of each sgRNA, multiplex sgRNAs driven by four independent Pol III promoters (human U6 promoter, mouse U6 promoter, 7SK and H1) have been tested using Golden Gate assembly method, which allows for robust and rapid cloning of up to four sgRNAs into a single lentiviral vector (Kabadi, A. M., et al. *Nucleic Acids Res* 42, e147 (2014)). Here a novel In-Fusion cloning strategy was developed with interrogated exchange of two restriction enzymes, rendering an easy and fast cloning of any numbers of multiplex sgRNAs into a single vector. This proof of concept is applicable to any multiplex sgRNAs under any Pol III promoters and various viral gene delivery systems. Although it was shown that 4 sgRNAs under 4 identical U6 promoter exhibited sufficient activity to induce target DNA cleavage, it was found that the sgRNA LTR1, GagD and PolB in the quadruplex sgRNA/saCas9 system are best but LTR-3 is weaker in cleaving HIV-1 provirus though it has high potency of cleaving in the duplex sgRNA system.

This study established the feasibility of using quadruplex sgRNAs/saCas9 AAV gene therapy in excising the integrated HIV-1 provirus in both Tg26 transgenic mice and humanized BLT mice, as well as possibly episomal HIV-1 DNA during acute infection in conventional mice inoculated with cell-free EcoHIV-eLuc reporter virus, in which sgRNAs/saCas9 can be considered as a pre-exposure prophylaxis (PrEP). The intravenous administration of AAV-DJ or AAV-DJ/8 achieved extensive gene transduction and HIV-1 eradication in most tissues/organs with the highest in liver, spleen, and lymph node. This current study demonstrates the clear excision of Gag/3'-LTR and 5'-LTR/Gag fragments in latently-infected human cells within mouse multiple organs/tissues by a single AAV-DJ/8 administration in HIV-infected humanized BLT mice. This finding also validates the vast extent of tissue reservoirs harboring HIV-1 viruses. The findings reported here provide the justifications for the further preclinical development of Cas9/sgRNA approach for HIV-1 eradication in preventing and improving HIV-1 diseases.

In conclusion, the small saCas9 protein size allows duplex or even quadruplex sgRNA-expressing cassettes to be harbored in all-in-one AAV vector for high titer packaging and robust gene transduction in cell cultures and animal models. The saCas9 with quadruplex sgRNAs targeting both 5' and 3' end LTR and structural Gag and Pol regions induces versatile patterns of small InDel mutations and large fragmental deletions and thus provides an optimal efficiency of HIV-1 genome eradication. The feasibility and efficiency of HIV-1 eradication in animals via AAV gene therapy paves the way towards preclinical studies and clinical trials in the near future.

TABLE 2

Oligonucleotides for sgRNAs targeting HIV-1 LTR, Gag and Pol and PCR primers.

| Target name | Direction | Sequence |
|---|---|---|
| sgRNA targeting oligonucleotides | | |
| LTR1 | T708: sense | caccGCAGAACTACACACCAGGGCC (SEQ ID NO: 1) |
|  | T709: antisense | aaacGGCCCTGGTGTGTAGTTCTGC (SEQ ID NO: 2) |
| LTR2 | T710: sense | caccGTTACACCCTATGAGCCAGCA (SEQ ID NO: 3) |
|  | T711: antisense | aaacTGCTGGCTCATAGGGTGTAAC (SEQ ID NO: 4) |
| LTR3 | T712: sense | caccGTGTGGCCTGGGCGGGACTG (SEQ ID NO: 5) |
|  | T713: antisense | aaacCAGTCCCGCCCAGGCCACAC (SEQ ID NO: 6) |
| Gag-B | T714: sense | caccGCCTTCCCACAAGGGAAGGCCA (SEQ ID NO: 7) |
|  | T715: antisense | aaacTGGCCTTCCCTTGTGGGAAGGC (SEQ ID NO: 8) |
| Gag-C | T758: sense | caccGCGAGAGCGTCGGTATTAAGCG (SEQ ID NO: 9) |
|  | T759: antisense | aaacCGCTTAATACCGACGCTCTCGC (SEQ ID NO: 10) |
| Gag-D | T760: sense | caccGGATAGATGTAAAAGACACCA (SEQ ID NO: 11) |
|  | T761: antisense | aaacTGGTGTCTTTTACATCTATCC (SEQ ID NO: 12) |
| Pol-B | T716: sense | caccGCATGGGTACCAGCACACAA (SEQ ID NO: 13) |
|  | T717: antisense | aaacTTGTGTGCTGGTACCCATGC (SEQ ID NO: 14) |
| Primers for conventional PCR | | |
| Gag | T458: antisense | CCCACTGTGTTTAGCATGGTATT (SEQ ID NO: 15) |
|  | T457: sense | AATGGTACATCAGGCCATATCAC (SEQ ID NO: 16) |
| GagC | T758: sense | CACCGCGAGAGCGTCGGTATTAAGCG (SEQ ID NO: 17) |
| GagD | T761: antisense | CACCTGGTGTCTTTTACATCTATCC (SEQ ID NO: 18) |
| PolA | T689: sense | CACCGCAGGATATGTAACTGACAG (SEQ ID NO: 19) |
| LTR1 | T709: antisense | AAACGGCCCTGGTGTGTAGTTCTGC (SEQ ID NO: 20) |
| LTR2 | T710: sense | CACCGTTACACCCTATGAGCCAGCA (SEQ ID NO: 21) |
|  | T711: antisense | AAACTGCTGGCTCATAGGGTGTAAC (SEQ ID NO: 22) |
| LTR-E | T361: sense | CACCGATCTGTGGATCTACCACACACA (SEQ ID NO: 23) |
| LTR-F | T363: antisense | CACCGCTGCTTATATGCAGCATCTGAG (SEQ ID NO: 24) |
| Cas-hU6 | T351: sense | CGCCTCGAGGATCCGAGGGCCTATTTCCCATGATTCC (SEQ ID NO: 25) |
| Tg26-3vector | T645: antisense | TGGAATGCAGTGGCGCGATCTTGGC (SEQ ID NO: 26) |

TABLE 2-continued

Oligonucleotides for sgRNAs targeting HIV-1 LTR, Gag and Pol and PCR primers.

| Target name | Direction | Sequence |
|---|---|---|
| SaCas9 | T955: sense | AACAGATTCAAGACCAGCGACTAC (SEQ ID NO: 27) |
|  | T956: antisense | TACCATTCTTTGATGTCCTTCCAG (SEQ ID NO: 28) |
| GAPDH | T623: antisense | GCTAAGCAGTTGGTGGTGCAGGA (SEQ ID NO: 29) |
|  | 40: sense | TCACCATCTTCCAGGAGCGA (SEQ ID NO: 30) |
| β-actin | sense | GGACTTCGAGCAAGAGATGG (SEQ ID NO: 31) |
|  | antisense | ACACTGTGTTGGCGTACAG (SEQ ID NO: 32) |
| Gag-Nest | T946: antisense | ACCTGGCTGTTGTTTCCTGTGTC (SEQ ID NO: 33) |
| HIV-U5a | T425: antisense | AAACGAGTCACACAACAGACGGGC (SEQ ID NO: 34) |
| LTR-1-Off-1 | T991: sense | TCAGCCATGAGGAAGAACTTGGA (SEQ ID NO: 35) |
|  | T992: antisense | TCTCCAGAGTGCTGGCAAGGTCC (SEQ ID NO: 36) |
| LTR-1-Off-2 | T993: sense | TCACCTGGTGCCAGTGTCTGCGG (SEQ ID NO: 37) |
|  | T994: antisense | TATGAATGAGTTTGGCGTGTATG (SEQ ID NO: 38) |
| LTR-1-Off-3 | T995: sense | ATCGATGAGGCTCTCAGCATCACC (SEQ ID NO: 39) |
|  | T996: antisense | TGGTGAGGCCTCTGGGCCACTTGAG (SEQ ID NO: 40) |
| LTR-3-Off-1 | T1013: sense | AGCCACACTCTGGCACTGAGACAAG (SEQ ID NO: 41) |
|  | T1014: antisense | AGTAAGCATAGGTATGGAGAGGC (SEQ ID NO: 42) |
| LTR-3-Off-3 | T1017: sense | ACAGCCACATGCAGGAGGTGACCAC (SEQ ID NO: 43) |
|  | T1018: antisense | ACATGTGCCTTGGCTTGTATGTGG (SEQ ID NO: 44) |
| Gag-D-Off-1 | T1019: sense | TTGAAGCAGAGTTAAGGAATCTTGG (SEQ ID NO: 45) |
|  | T1020: antisense | TGCCATGTTCCTTCTGTAATCATAG (SEQ ID NO: 46) |
| Gag-D-Off2 | T1021: sense | TCTCTATGTAGTCTTGGCTGTCCTG (SEQ ID NO: 47) |
|  | T1022: antisense | ACCATGCCATCTAGCTGTGCTGAC (SEQ ID NO: 48) |

Primer for Real-time PCR

| Gag | T760: sense | CACCGGATAGATGTAAAAGACACCA (SEQ ID NO: 49) |
|  | T946: antisense | ACCTGGCTGTTGTTTCCTGTGTC (SEQ ID NO: 50) |
| Env | T876: sense | CCGAAGGAATAGAAGAAGAAG (SEQ ID NO: 51) |
|  | T691: antisense | CACCGAGAGTAAGTCTCTCAAGCGG (SEQ ID NO: 52) |
| Tat | T1002: sense | TGGAAGCATCCAGGAAGTCAGCC (SEQ ID NO: 53) |
|  | T1003: antisense | TTCTTCTTCTATTCCTTCGGGCC (SEQ ID NO: 54) |
| Mouse Ppia | T979: sense | GCCCAGTATGCTTGGGTATC (SEQ ID NO: 55) |
|  | T980: antisense | TGCTGACTCCCAGAACAGA (SEQ ID NO: 56) |

TABLE 2-continued

Oligonucleotides for sgRNAs targeting HIV-1 LTR, Gag and Pol and PCR primers.

| Target name | Direction | Sequence |
|---|---|---|
| Human β2M | sense | TGCTGTCTCCATGTTTGATGTATCT (SEQ DD NO: 57) |
|  | antisense | TCTCTGCTCCCCACCTCTAAGT (SEQ ID NO: 58) |
| 5' LTR1 + gagD uncut | T872 | GGACTCGGCTTGCTGAAG (SEQ ID NO: 59) |
|  | T759 | aaacCGCTTAATACCGACGCTCTCGC (SEQ ID NO: 60) |
| 5' LTR1 + gagD cut | T361 | caccGATCTGTGGATCTACCACACACA (SEQ ID NO: 61) |
|  | T946 | ACCTGGCTGTTGTTTCCTGTGTC (SEQ ID NO: 62) |
| 5' LTR1 + gagD internal | T457 | AATGGTACATCAGGCCATATCAC (SEQ ID NO: 63) |
|  | T458 | CCCACTGTGTTTAGCATGGTATT (SEQ ID NO: 64) |
| gagD + 3'LTR1 uncut | T873 | ATCTCTGCTGTCCCTGTAA (SEQ ID NO: 65) |
|  | T874 | AATCCCCAAAGTCAAGGAGTAA (SEQ ID NO: 66) |
| gagD + 3'LTR1 cut | T758 | caccGCGAGAGCGTCGGTATTAAGCG (SEQ ID NO: 67) |
|  | T535 | AAACAAGGTCAGTGGATATCTGATC (SEQ ID NO: 68) |
| gagD + 3'LTR1 internal | T872 | GGACTCGGCTTGCTGAAG (SEQ ID NO: 69) |
|  | T759 | aaacCGCTTAATACCGACGCTCTCGC (SEQ ID NO: 70) |
| gagD + 3'LTR3 uncut | T873 | ATCTCTGCTGTCCCTGTAA (SEQ ID NO: 71) |
|  | T874 | AATCCCCAAAGTCAAGGAGTAA (SEQ ID NO: 72) |
| gagD + 3'LTR3 cut | T758 | caccGCGAGAGCGTCGGTATTAAGCG (SEQ ID NO: 73) |
|  | T363 | caccGCTGCTTATATGCAGCATCTGAG (SEQ ID NO: 74) |
| gagD + 3'LTR3 internal | T872 | GGACTCGGCTTGCTGAAG (SEQ ID NO: 75) |
|  | T759 | aaacCGCTTAATACCGACGCTCTCGC (SEQ ID NO: 76) |

What is claimed:

1. An adeno-associated viral vector serotype 9 (AAV$_9$) expression vector, comprising a nucleic acid sequence encoding:
   (a) a Clustered Regularly Interspaced Short Palindromic Repeat (CRISPR)-associated endonuclease;
   (b) a first guide RNA (gRNA), wherein the first gRNA targets a long terminal repeat (LTR) of a human immunodeficiency virus (HIV) sequence and the nucleic acid sequence encoding the first gRNA comprises any one of the rRNA encoding sequences of SEQ ID NOs: 1-6; and
   (c) a second gRNA, wherein the nucleic acid sequence encoding the second gRNA comprises any one of the gRNA encoding sequences of SEQ ID NOs: 11 and 12, wherein the CRISPR-associated endonuclease, the first gRNA, and the second gRNA are capable of excising intervening sequences between the first target sequence and the second target sequence.

2. The AAV$_9$ expression vector of claim 1, wherein the CRISPR-associated endonuclease is Cas9 or a homologue thereof.

3. The AAV$_9$ expression vector of claim 1, further comprising a nucleic acid sequence encoding a transactivating small RNA (tracrRNA).

4. The AAV$_9$ expression vector of claim 3, wherein the sequence encoding the (tracrRNA) is fused to a sequence encoding the first gRNA or the second gRNA.

5. The AAV$_9$ expression vector of claim 1, further comprising a nucleic acid sequence encoding a nuclear localization signal.

6. A method of treating a human immunodeficiency virus (HIV) infection in a subject in need thereof, the method comprising administering to the subject an adeno-associated viral vector serotype 9 (AAV$_9$) expression vector comprising a sequence encoding:
- (a) a Clustered Regularly Interspaced Short Palindromic Repeat (CRISPR)-associated endonuclease;
- (b) a first guide RNA (gRNA), wherein the first gRNA targets a long terminal repeat (LTR) of a human immunodeficiency virus (HIV) sequence and the nucleic acid sequence encoding the first gRNA comprises any one of the guide encoding sequences of SEQ ID NOs: 1-6; and
- (c) a second gRNA, wherein the nucleic acid sequence encoding the second gRNA comprises any one of the gRNA encoding sequences of SEQ ID NOs: 11 and 12,
- wherein the CRISPR-associated endonuclease, the first gRNA, and the second gRNA are capable of excising intervening sequences between the first target sequence and the second target sequence, thereby treating the HIV infection.

7. The method of claim 6, wherein the CRISPR-associated endonuclease is Cas9 or a homologue thereof.

8. The method of claim 6, wherein the target sequence within the LTR is within a U3, R, or U5 region of the LTR.

9. The method of claim 6, wherein the expression vector further comprises a nucleic acid sequence encoding a trans-activating small RNA (tracrRNA).

10. The method of claim 9, wherein the nucleic acid sequence encoding the tracrRNA is fused to a sequence encoding the first gRNA or the second gRNA.

11. The method of claim 6, wherein the expression vector further comprises a nucleic acid sequence encoding a nuclear localization signal.

\* \* \* \* \*

SEQUENCE LISTING

<160> NUMBER OF SEQ ID NOS: 236

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
caccgcagaa ctacacacca gggcc                                    25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 2

```
aaacggccct ggtgtgtagt tctgc                                           25
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
caccgttaca ccctatgagc cagca                                           25
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
aaactgctgg ctcatagggt gtaac                                           25
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
caccgtgtgg cctgggcggg actg                                            24
```

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
aaaccagtcc cgcccaggcc acac                                            24
```

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
caccgccttc ccacaaggga aggcca                                          26
```

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaactggcct tcccttgtgg gaaggc                                              26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caccgcgaga gcgtcggtat taagcg                                              26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaccgctta ataccgacgc tctcgc                                              26

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caccggatag atgtaaaaga cacca                                               25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaactggtgt cttttacatc tatcc                                               25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caccgcatgg gtaccagcac acaa                                                24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaacttgtgt gctggtaccc atgc                                                24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccactgtgt ttagcatggt att                                           23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aatggtacat caggccatat cac                                           23

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caccgcgaga gcgtcggtat taagcg                                        26

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cacctggtgt cttttacatc tatcc                                         25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caccgcagga tatgtaactg acag                                          24

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaacggccct ggtgtgtagt tctgc                                         25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caccgttaca ccctatgagc cagca                                          25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaactgctgg ctcatagggt gtaac                                          25

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caccgatctg tggatctacc acacaca                                        27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caccgctgct tatatgcagc atctgag                                        27

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgcctcgagg atccgagggc ctatttccca tgattcc                             37

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tggaatgcag tggcgcgatc ttggc                                          25

```
<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aacagattca agaccagcga ctac                                          24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
taccattctt tgatgtcctt ccag                                          24

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctaagcagt tggtggtgca gga                                           23

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcaccatctt ccaggagcga                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggacttcgag caagagatgg                                               20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acactgtgtt ggcgtacag                                                19

<210> SEQ ID NO 33
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acctggctgt tgtttcctgt gtc                                            23

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaacgagtca cacaacagac gggc                                           24

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcagccatga ggaagaactt gga                                            23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tctccagagt gctggcaagg tcc                                            23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcacctggtg ccagtgtctg cgg                                            23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tatgaatgag tttggcgtgt atg                                            23

<210> SEQ ID NO 39
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atcgatgagg ctctcagcat cacc                                            24

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tggtgaggcc tctgggccac ttgag                                           25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agccacactc tggcactgag acaag                                           25

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agtaagcata ggtatggaga ggc                                             23

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acagccacat gcaggaggtg accac                                           25

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acatgtgcct tggcttgtat gtgg                                            24

<210> SEQ ID NO 45
<211> LENGTH: 25
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 45
ttgaagcaga gttaaggaat cttgg                                            25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgccatgttc cttctgtaat catag                                            25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tctctatgta gtcttggctg tcctg                                            25

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
accatggcat ctagctgtgc tgac                                             24

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caccggatag atgtaaaaga cacca                                            25

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acctggctgt tgtttcctgt gtc                                              23

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccgaaggaat agaagaagaa g                                            21

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
caccgagagt aagtctctca agcgg                                        25

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tggaagcatc caggaagtca gcc                                          23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttcttcttct attccttcgg gcc                                          23

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcccagtatg cttgggtatc                                              20

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgctgactcc cagaacaga                                               19

<210> SEQ ID NO 57
<211> LENGTH: 25
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 57
tgctgtctcc atgtttgatg tatct                                        25

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tctctgctcc ccacctctaa gt                                           22

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggactcggct tgctgaag                                                18

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aaaccgctta ataccgacgc tctcgc                                       26

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
caccgatctg tggatctacc acacaca                                      27

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acctggctgt tgtttcctgt gtc                                          23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
              primer

<400> SEQUENCE: 63
aatggtacat caggccatat cac                                              23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cccactgtgt ttagcatggt att                                              23

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
atctctgctg tccctgtaa                                                   19

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aatcccaaaa gtcaaggagt aa                                               22

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caccgcgaga gcgtcggtat taagcg                                           26

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aaacaaggtc agtggatatc tgatc                                            25

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 69
ggactcggct tgctgaag                                                18

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaaccgctta ataccgacgc tctcgc                                       26

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
atctctgctg tccctgtaa                                               19

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aatccccaaa gtcaaggagt aa                                           22

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
caccgcgaga gcgtcggtat taagcg                                       26

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
caccgctgct tatatgcagc atctgag                                      27

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 75
ggactcggct tgctgaag                                                  18

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aaaccgctta ataccgacgc tctcgc                                         26

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggatcagata tccactgacc tttggat                                        27

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ggatagatgt aaaagacacc aaggagg                                        27

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gatctgtgga tctaccacac aca                                            23

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ttggcagaac tacacaccag gg                                             22

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
```
accatttgcc cctggaggtt                                              20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tccttgggat gttgatgatc t                                            21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tggcccaaac attatgtacc                                              20

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tggtggttgc ttctttccac aca                                          23

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
aagtagtgtg tgcccgtctg                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tcgagagatc tcctctggct                                              20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ctgttcgggc gccactgcta                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agcgcaagta ctctgtgtgg                                              20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aacagtccgc ctagaagcat                                              20

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cctccatcgt gcaccgcaa                                               19

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gcagaactac acaccagggc cagggat                                      27

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ggatagatgt aaaagacacc aaggaag                                      27

<210> SEQ ID NO 93
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ttagcagaac tacacaccag ggccagggat cagatatcca ctgacctttg gatgg       55

<210> SEQ ID NO 94
<211> LENGTH: 43
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 94
aaggatagat gtaaaagaca ccaaggaagc cttagataag ata                43

<210> SEQ ID NO 95
<211> LENGTH: 34
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 95
accctatagt gcagaacctc cagggcaaa tggt                          34

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 96
ttagcagaac tacacaccag gg                                      22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 97
ccaggaagcc ttagataaga ta                                      22

<210> SEQ ID NO 98
<211> LENGTH: 34
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 98
accctatagt gcagaacatc cagggcaaa tggt                          34

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 99
ttagcagaac tacacaccag gg                                      22

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ccagggatgc cttagataag ata                                                  23

<210> SEQ ID NO 101
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
accctatagt gcagaacatc caggggcaaa tggt                                      34

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ttagcagaac tacacaccag gg                                                   22

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ccaaggaagc cttagataag ata                                                  23

<210> SEQ ID NO 104
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
accctatagt gcagaacatc cagggcaaa tggt                                       34

<210> SEQ ID NO 105
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gtggatctac cacacacaag gctacttccc tgattggcag aactacacac cagggccagg          60
gatcagatat ccactgacct ttggatggt                                            89

<210> SEQ ID NO 106
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtggatctac cacacacaag gctacttccc tgattggcag aactacacac cagg         54

<210> SEQ ID NO 107
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gtggatctac cacacacaag gctacttccc tgattggcag aactacacac ca           52

<210> SEQ ID NO 108
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gtggatctac cacacacaag gctacttccc tgattggcag aactacacac cagggccagg   60
gat                                                                  63

<210> SEQ ID NO 109
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gtggatctac cacacacaag gctacttccc tgattggcag aactacacac cagg         54

<210> SEQ ID NO 110
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gtggatctac cacacacaag gctacttccc tgattggcag aactacacac ca           52

<210> SEQ ID NO 111
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gtggatctac cacacacaag gctacttccc tgattggcag aactacacac cagg    54

<210> SEQ ID NO 112
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gtggatctac cacacacaag gctacttccc tgattggcag aactacacac cagg    54

<210> SEQ ID NO 113
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gtggatctac cacacacaag gctacttccc tgattggcag aactacacac cagg    54

<210> SEQ ID NO 114
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
aaggatagat gtaaaagaca ccaaggaagc cttagataag ataga    45

<210> SEQ ID NO 115
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cagccaaaat taccctatag tgcagaacct ccagggcaa atggt    45

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ccaaggaagc cttagataag ataga    25

<210> SEQ ID NO 117
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cagccaaaat taccctatag tgcagaacat ccagggcaa atggt    45

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
aggaagcctt agataagata ga                                              22

<210> SEQ ID NO 119
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
caaccaaaat taccctatag tgcagaacat ccaggggcaa atggt                     45

<210> SEQ ID NO 120
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ccttagataa gacaga                                                     16

<210> SEQ ID NO 121
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cagccaaaat taccctatag tgcagaacat ccaggggcaa atggt                     45

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ccaaggaagc cttagataag ataga                                           25

<210> SEQ ID NO 123
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cagccaaaat taccctatag tgcagaacat ccaggggcaa atggt                     45

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
aggaagcctt agataagata ga                                              22

<210> SEQ ID NO 125
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cagccaaaat taccctatag tgcagaacat ccaggggcaa atggt                     45

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 126
ccaaggaagc cttanataag ataga                                           25

<210> SEQ ID NO 127
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cagccaaaat taccctatag tgcagaacat ccaggggcaa atggt                     45

<210> SEQ ID NO 128
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ccaaggaagc cttagataag ataga                                           25

<210> SEQ ID NO 129
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cagccaaaat taccctatag tgcagaacat ccaggggcaa atggt       45

<210> SEQ ID NO 130
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ccaaggaagc cttagataag ataga       25

<210> SEQ ID NO 131
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
cagccaaaat taccctatag tgcggaacat ccaggggcaa atggt       45

<210> SEQ ID NO 132
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gagggctcgc cactcccag agctgc       26

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cgctcccctg gtgtgtagtt ctgcc       25

<210> SEQ ID NO 134
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
agggctcgcc actcccagc ctggtgtgta gttctgccaa tcaggg       46

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
atctgtggat ctaccacaca caag                                          24

<210> SEQ ID NO 136
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tggcagaact acacaccagg gccagggat                                     29

<210> SEQ ID NO 137
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
aaaggataga tgtaaaagac accaaggaag                                    30

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
tttaaatacc atgctaaaca cag                                           23

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
atctgtggat ctaccacaca cagt                                          24

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tggcagaact acacaccagg aag                                           23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tttaaatacc atgctaaaca cag                                           23

<210> SEQ ID NO 142
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tggatctacc acacacagtg ctacttccct gattggcaga actacacacc aggaagcctt     60
agataagata gaggaagagc aaa                                             83

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gcgagagcgt cggtattaag cg                                              22

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ggatagatgt aaaagacacc aaggaag                                         27

<210> SEQ ID NO 145
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gcagaactac acaccagggc caggggt                                         27

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ctcagatgct gcatataagc agc                                             23

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gagagcgtcg gtattaagcg                                           20

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ggatagatgt aaaagacagg ggt                                       23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ctcagatgct gcatataagc agc                                       23

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gcgagagcgt cggtattaag gg                                        22

<210> SEQ ID NO 151
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggatagatgt aaaagacagc caggggt                                   27

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ctcagatgct gcatataagc agc                                       23

<210> SEQ ID NO 153
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcgagagcgt cggtattaag cg                                        22

```
<210> SEQ ID NO 154
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ggatagatgt aaaagacacg agagcgtcgg tattaagcgc caggggt            47

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ctcagatgct gcatataagc agc                                      23

<210> SEQ ID NO 156
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gcgagagcgt cggtattaag cg                                       22

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggatagatgt aaaagacagc caggggt                                  27

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ctcagatgct gcatataagc ag                                       22

<210> SEQ ID NO 159
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
aggatagatg taaaagacag gggtcagata tccactgacc tttggat            47
```

<210> SEQ ID NO 160
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gatagatgta aaagacagcc aggggtcaga tatccactga cctt                44

<210> SEQ ID NO 161
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gcgagagcgt cggtattaag cg                                        22

<210> SEQ ID NO 162
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ggatagatgt aaaagacacc aaggaag                                   27

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gcagaactac acaccagggc cagggt                                    27

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ctcagatgct gcatataagc agc                                       23

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base

```
<222> LOCATION: (8)..(8)
<223> OTHER INFORMATION: a, c, t, g, unknown or other

<400> SEQUENCE: 165
gcnngagngt cggtattagc g                                            21

<210> SEQ ID NO 166
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ggatagatgt aaaagacagc caggggt                                      27

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ctcagatgct gcatataagc agc                                          23

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gcgagagcgt cggtattagc g                                            21

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ggatagatgt aaaagacagc caggggt                                      27

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ctcagatgct gcatataagc agc                                          23

<210> SEQ ID NO 171
<211> LENGTH: 22
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 171
gcgagagcgt cggtattaag cg                                    22

<210> SEQ ID NO 172
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ggatagatgt aaaagacagc caggggt                               27

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ctcagatgct gcatataagc agc                                   23

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gcgagagcgt cggtattaag cg                                    22

<210> SEQ ID NO 175
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggatagatgt aaaagacagc caggggt                               27

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 176
ctcagatgct gcatataanc ngc                                   23

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 177
gagcgtcngt attaagcg                                                    18

<210> SEQ ID NO 178
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ggatagatgt aaaagacagc caggggt                                          27

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ctcagatgct gcatataagc agc                                              23

<210> SEQ ID NO 180
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gcgagagcgt cggtattaag cg                                               22

<210> SEQ ID NO 181
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ggatagatgt aaaagacagc caggggt                                          27

<210> SEQ ID NO 182
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ctcagatgct gcaataagca gc                                              22

<210> SEQ ID NO 183
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gcgagagcgt cggtattaag cg                                              22

<210> SEQ ID NO 184
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ggatagatgt aaaagacagc caggggt                                         27

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cccagatgct gcattaagca gc                                              22

<210> SEQ ID NO 186
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
atagatgtaa aagacagcca ggggtcagat atccactgac cttta                     45

<210> SEQ ID NO 187
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aaaggataga tgtaaaagac agccaggggt cagatatcca ctgacc                    46

<210> SEQ ID NO 188
<211> LENGTH: 712
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188

| | |
|---|---|
| tcagccatga ggaagaactt ggacagcagt gtggccccta agggagagaa aggagatgca | 60 |
| aatcagagag ccctgtccaa gtacagtttg gggtagggg cattgcagag gtttgagtga | 120 |
| tattcccact gctgctgaca tgataccctc atgactctga gattctgttt ctctctcgtc | 180 |
| atactaaagg ccctatagag atagaatatt ccagaacaaa cagccagtgc tgagcgtcca | 240 |
| gccgcataga gctcagctca gagctcacaa acagcttggt aaacatctgt tggtgtcccc | 300 |
| aggatgggtg tcttccctga gcattctctg tggctgtaag gcccagacag catgctctct | 360 |
| gtacacacca gggccaggaa aagatccagc ccgcactggg cttccagcat agctagctaa | 420 |
| gctgggacag agaaaggcag acttaggact tccctttggt gttttctca atgcctcaac | 480 |
| caaaacacac aaagggaagg tgtcttacac aggcaggagg aagcaggccc ctactcttga | 540 |
| caccacttaa cagtagggct ggcaatgcca gcccagagct tgtgtctcct cacagcagaa | 600 |
| gacagcaaag gcttctgcaa tccagctcac tggggaccag ggaagggtga ctttggttta | 660 |
| aagaagaccc tgactctcag gcctggcttg gaccttgcca gcactctgga ga | 712 |

<210> SEQ ID NO 189
<211> LENGTH: 590
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 189

| | |
|---|---|
| agccacactc tggcactgag acaagttgcc ggtaattacc ccgagtccca ctcctctctg | 60 |
| gggcagagca catccaccac agcttcctcc tgggaaagcg agagacagcc tcctgcggtt | 120 |
| cctcaaacca aagtctgccc tggagatgcc aacctttaac tcaaaatcga acatcgactt | 180 |
| taatctttgg ggttctttag aatgggagaa gccctttcta ctctcccatc tcctaccccc | 240 |
| accccagtcc cgcccagatg cctggttctg cctcctgttg ataccttgag cctcaccaat | 300 |
| cagcagctgg ggcttctggg ctcccactgg ggaccatgcc tcctgcccat cccacaactg | 360 |
| tttcttgcta taactgtatc actcccccatt tcacaggact gggaggtaaa gagaatctac | 420 |
| actagatgat aaaaggcttt tgctctgttg tggtgtggga atcaaatgca aggcctctta | 480 |
| caagccagga aaagaggggc tgtttctttt gcttttttg gagacatggt ttcactatgc | 540 |
| agacctttaa ctcatagaga tcccctgcc tctccatacc tatgcttact | 590 |

<210> SEQ ID NO 190
<211> LENGTH: 593
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 190

| | |
|---|---|
| ttgaagcaga gttaaggaat cttgggcttc tctctggccc ctttgtgcaa tgatctagcg | 60 |
| ttaatccact ccttcaggga cttacaactg ttataaaatg gtcaacattc aaatagaacc | 120 |
| tgtacaaagg aagcctaagg aagaaattgg aggggaagg ggccctagga ccctataaat | 180 |
| atccctcctg gccaggtcag agaaccaccc ttggagtccc tgtcattcca ttggtgggag | 240 |
| ctcattgtct cttctaatgg tttctcattt tcattcattt tccccatttc aatctgtaac | 300 |
| ttactgtcag ggtgaggcct ataagtgtta ctactatgta aaagacacca agggtctctg | 360 |
| aatgaactct gaattatctg tcacattggt ctctgactca cgtcagtaac tgttattgtt | 420 |

```
tgggatctcc atgatctaaa ctacttttat tgtcatgtgg atgatccttt catgccctct    480
atctcagttt agatcctgtt atttccttaa cttgccctcc aattgatact ttaatttctt    540
ctttgagtgg ttctttacac ccttctttct atgattacag aaggaacatg gca           593
```

<210> SEQ ID NO 191
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 191
gcgagagcgt cggtattaag cg                                              22

<210> SEQ ID NO 192
<211> LENGTH: 27
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 192
ggatagatgt aaaagacacc aaggaag                                         27

<210> SEQ ID NO 193
<211> LENGTH: 27
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 193
gcagaactac acaccagggc caggggt                                         27

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 194
ctcagatgct gcatataagc agc                                             23

<210> SEQ ID NO 195
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 195
gcgagagcgt cggtattaag cg                                              22

<210> SEQ ID NO 196
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 196
ggatagatgt aaaagacagc caggggt                                27

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ctcagatgct gcatataagc agc                                   23

<210> SEQ ID NO 198
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
tatataatac aatagcagtc ctctattgtg tgcatcaaag gatagatgta aaagacagcc     60
aggggtcaga tatccactga cctttagatg gtgctacaag cttgtaccag ttgagcc      117

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gcgagagcgt cggtattaag cg                                    22

<210> SEQ ID NO 200
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ggatagatgt aaaagacacc aaggaag                               27

<210> SEQ ID NO 201
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gcagaactac acaccagggc caggggtctc agatgctgca tataagcagc       50

<210> SEQ ID NO 202
<211> LENGTH: 22
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 202
gcgagagcgt cggtattaag cg                                              22

<210> SEQ ID NO 203
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ggatagatgt aaaagatagc cagggtctc agatgctgca tataagcagc                 50

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gcgagagcgt cggtattaag cg                                              22

<210> SEQ ID NO 205
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ggatagatgt aaaagacagc cagggtccc agatgctgca tataagcagc                 50

<210> SEQ ID NO 206
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
cattatataa tacaatagca gtcctctatt gtgtgcatca aggatagat gtaaaagata      60 gccaggggtc agatatccac tgacctttag atggtgctac aagctagtac cag            113

<210> SEQ ID NO 207
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gcagaactac acaccagggc cagggat                                         27

<210> SEQ ID NO 208
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 208
gtgtggcctg ggcgggactg gggagt                                          26

<210> SEQ ID NO 209
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ggatagatgt aaaagacacc aaggaag                                         27

<210> SEQ ID NO 210
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
tcttgattat tgccagttga gcagcatgat tcgtcactgc tgagct                    46

<210> SEQ ID NO 211
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tcttgattat tgccagttga gcagcatgat tcgtcactgc tgagct                    46

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gatctgtgga tctaccacac aca                                             23

<210> SEQ ID NO 213
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gcagaactac acaccagggc cagggat                                         27

<210> SEQ ID NO 214
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 214
ggatagatgt aaaagacacc aaggaag                                              27

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gacacaggaa acaacagcca gg                                                   22

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gatctgtgga tctaccacac aca                                                  23

<210> SEQ ID NO 217
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gcagaactac acaccaggcc aaggaag                                              27

<210> SEQ ID NO 218
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gacacaggaa acaacagcca gg                                                   22

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
gatctgtgga tctaccacac aca                                                  23

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 220
gcagaactac acaccaagga ag                                                22

<210> SEQ ID NO 221
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gacacaggaa acaacagcca gg                                                22

<210> SEQ ID NO 222
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gtggatctac cacacacaag gctacttccc tgtttggcag aactacacac caaggaagcc       60
ttagataaga tagaggaaga gcaaa                                             85

<210> SEQ ID NO 223
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ggatagatgt aaaagacacc aaggaag                                           27

<210> SEQ ID NO 224
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gcagaactac acaccagggc caggggt                                           27

<210> SEQ ID NO 225
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gcgtggcctg ggcgggactg gggagt                                            26

<210> SEQ ID NO 226
<211> LENGTH: 22
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 226
gcgagagcgt cggtattaag cg                                                   22

<210> SEQ ID NO 227
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ggatagatgt aaaagacacc aaggaag                                              27

<210> SEQ ID NO 228
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gcagaactac acaccagggc caggggt                                              27

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ctcagatgct gcatataagc agc                                                  23

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gcgagagcgt cggtattaag cg                                                   22

<210> SEQ ID NO 231
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggatagatgt aaaagacaca ggggt                                                25

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
```

```
        oligonucleotide

<400> SEQUENCE: 232
ctcagatgct gcatataa                                                     18

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 233
gcgagagcgt cggtattaag cg                                                22

<210> SEQ ID NO 234
<211> LENGTH: 27
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 234
ggatagatgt aaaagacagc caggggt                                           27

<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 235
ctcagatgct gcatataagc agc                                               23

<210> SEQ ID NO 236
<211> LENGTH: 56
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 236
ggatagatgt aaaagacagc caggggtcag atatccactg acctttggat ggtgct           56
```